US012631622B2

(12) United States Patent　　(10) Patent No.: US 12,631,622 B2
Birnbaum et al.　　(45) **Date of Patent: \*May 19, 2026**

(54) LIGAND DISCOVERY AND GENE DELIVERY VIA RETROVIRAL SURFACE DISPLAY

(71) Applicant: Massachusetts Institute of Technology, Cambridge, MA (US)

(72) Inventors: Michael Birnbaum, Arlington, MA (US); Connor Dobson, Takoma Park, MD (US)

(73) Assignee: Massachusetts Institute of Technology, Cambridge, MA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 19/350,928

(22) Filed: Oct. 6, 2025

(65) Prior Publication Data

US 2026/0029399 A1　　Jan. 29, 2026

Related U.S. Application Data

(63) Continuation of application No. 19/014,949, filed on Jan. 9, 2025, now Pat. No. 12,455,280, which is a continuation of application No. 18/458,657, filed on Aug. 30, 2023, now Pat. No. 12,222,347, which is a continuation of application No. 16/826,665, filed on Mar. 23, 2020, now Pat. No. 12,061,187.

(60) Provisional application No. 62/851,889, filed on May 23, 2019.

(51) Int. Cl.
*G01N 33/50* (2006.01)
*C07K 14/005* (2006.01)
*C07K 14/47* (2006.01)
*C07K 14/54* (2006.01)
*C07K 14/705* (2006.01)
*C07K 14/74* (2006.01)
*C07K 16/28* (2006.01)
*C12N 15/86* (2006.01)

(52) U.S. Cl.
CPC ......... *G01N 33/505* (2013.01); *C07K 14/005* (2013.01); *C07K 14/4748* (2013.01); *C07K 14/5437* (2013.01); *C07K 14/70532* (2013.01); *C07K 14/70539* (2013.01); *C07K 16/2803* (2013.01); *C12N 15/86* (2013.01); *C07K 2317/622* (2013.01); *C07K 2319/02* (2013.01); *C07K 2319/035* (2013.01); *C07K 2319/60* (2013.01); *C12N 2740/15045* (2013.01)

(58) Field of Classification Search
CPC ............. G01N 33/505; G01N 33/5047; G01N 33/5008; C07K 14/005; C07K 14/4748;
C07K 14/5437; C07K 14/70532; C07K 14/70539; C07K 16/2803; C07K 2317/622; C07K 2319/02; C07K 2319/035; C07K 2319/60; C07K 14/47; C12N 15/86; C12N 2740/15045; C12N 2740/16043; C12N 2740/16045; C12N 2810/85; C12N 2810/852; C12N 2810/855; C12N 2810/859; C40B 30/04
See application file for complete search history.

(56) References Cited

U.S. PATENT DOCUMENTS

| | | | |
|---|---|---|---|
| 7,901,671 | B2 | 3/2011 | Leboulch et al. |
| 9,994,867 | B2 | 6/2018 | Baltimore et al. |
| 12,061,187 | B2 | 8/2024 | Birnbaum et al. |
| 12,061,188 | B2 | 8/2024 | Birnbaum et al. |
| 12,222,347 | B2 | 2/2025 | Birnbaum et al. |
| 12,455,280 | B2 | 10/2025 | Birnbaum et al. |
| 2008/0241929 | A1 | 10/2008 | Naldini et al. |
| 2014/0017766 | A1 | 1/2014 | Chen et al. |
| 2015/0031651 | A1 | 1/2015 | Moller et al. |
| 2015/0182617 | A1 | 7/2015 | Bauche et al. |
| 2015/0316511 | A1 | 11/2015 | Guo |
| 2016/0333374 | A1 | 11/2016 | Anastasov et al. |
| 2017/0051252 | A1 | 2/2017 | Morgan et al. |
| 2017/0176435 | A1 | 6/2017 | Seidell, III et al. |
| 2017/0192011 | A1 | 7/2017 | Birnbaum et al. |
| 2017/0356010 | A1 | 12/2017 | Frost et al. |
| 2018/0201954 | A1 | 7/2018 | Buchholz et al. |
| 2018/0362966 | A1 | 12/2018 | Flechtner et al. |
| 2019/0144885 | A1 | 5/2019 | Costa Fejoz et al. |
| 2020/0216502 | A1 | 7/2020 | Albertini et al. |
| 2020/0371088 | A1 | 11/2020 | Birnbaum et al. |
| 2022/0204946 | A1 | 6/2022 | Tomas et al. |
| 2024/0044873 | A1 | 2/2024 | Birnbaum et al. |

FOREIGN PATENT DOCUMENTS

| | | |
|---|---|---|
| CN | 1643164 A | 7/2005 |
| EP | 1461079 B1 | 8/2011 |
| WO | WO 2008/037458 A2 | 4/2008 |

(Continued)

OTHER PUBLICATIONS

Singaporean Search Report dated Sep. 15, 2023, for Application No. 11202112344V.

(Continued)

*Primary Examiner* — Rachel B Gill
(74) *Attorney, Agent, or Firm* — Wolf, Greenfield & Sacks, P.C.

(57) ABSTRACT

Compositions of retroviruses and methods of using the same for gene delivery are disclosed, wherein the retroviruses comprise a viral envelope protein comprising at least one mutation that diminishes its native function, a non-viral membrane-bound protein comprising a membrane-bound domain and an extracellular targeting domain.

30 Claims, 26 Drawing Sheets

Specification includes a Sequence Listing.

(56)                    References Cited

FOREIGN PATENT DOCUMENTS

| WO | WO 2009/013324 A1 | 1/2009 |
| WO | WO 2012/088381 A2 | 6/2012 |
| WO | WO 2015/104376 A1 | 7/2015 |
| WO | WO 2015/112541 A2 | 7/2015 |
| WO | WO 2015/117027 A1 | 8/2015 |
| WO | WO 2017/182585 A1 | 12/2017 |
| WO | WO 2019/005601 A1 | 1/2019 |
| WO | WO 2019/056015 A2 | 3/2019 |
| WO | WO 2019/057974 A1 | 3/2019 |
| WO | WO 2020/236263 A1 | 11/2020 |

OTHER PUBLICATIONS

Invitation to Pay Additional Fees mailed Jul. 15, 2020, for Application No. PCT/US2020/024175.

International Search Report and Written Opinion mailed Sep. 14, 2020, for Application No. PCT/US2020/024175.

International Preliminary Report on Patentability mailed Dec. 2, 2021, for Application No. PCT/US2020/024175.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Bentzen et al., Evolution of MHC-based technologies used for detection of antigen-responsive T cells. Cancer Immunol Immunother. Mar. 17, 2017;66:657-66.

Bowie et al., Deciphering the message in protein sequences: tolerance to amino acid substitutions. Science. Mar. 16, 1990;247(4948):1306-10.

Buchholz et al., Retroviral display and high throughput screening. Comb Chem High Throughput Screen. Feb. 2008;11(2):99-110.

Chan et al., Conjugation of lentivirus to paramagnetic particles via nonviral proteins allows efficient concentration and infection of primary acute myeloid leukemia cells. J Virol. Oct. 2005;79(20):13190-4.

Chen et al., Human monoclonal antibodies targeting the haemagglutinin glycoprotein can neutralize H7N9 influenza virus. Nat Commun. Mar. 30, 2015;6:6714.

Ciré et al., Immunization of mice with lentiviral vectors targeted to MHC class II+ cells is due to preferential transduction of dendritic cells in vivo. PLoS One. Jul. 24, 2014;9(7):e101644.

Dobson et al., Antigen identification and high-throughput interaction mapping by reprogramming viral entry. Nat Methods. Apr. 2022;19(4):449-460. doi: 10.1038/s41592-022-01436-z. Epub Apr. 8, 2022.

Dreja et al., The effects of N-terminal insertion into VSV-G of an scFv peptide. Virol J. Sep. 2, 2006;3:69.

Frank et al., Surface-Engineered Lentiviral Vectors for Selective Gene Transfer into Subtypes of Lymphocytes. Mol Ther Methods Clin Dev. Oct. 17, 2018;12:19-31.

Froelich et al., Targeted gene delivery to CD117-expressing cells in vivo with lentiviral vectors co-displaying stem cell factor and a fusogenic molecule. Biotechnol Bioeng. Sep. 1, 2009;104(1):206-15. doi: 10.1002/bit.22378.

Funke et al., Targeted Cell Entry of Lentiviral Vectors. Mol Ther. Aug. 2008;16(8):1427-36.

Goyvaerts et al., Targeting of human antigen-presenting cell subsets. J Virol. Oct. 2013;87(20):11304-8. doi: 10.1128/JVI.01498-13. Epub Jul. 17, 2013.

Goyvaerts et al., Development of the Nanobody display technology to target lentiviral vectors to antigen-presenting cells. Gene Ther. Dec. 2012;19(12):1133-40. doi: 10.1038/gt.2011.206. Epub Jan. 12, 2012.

Grubaugh et al., Proteins as T cell antigens: methods for high-throughput identification. Vaccine. Aug. 20, 2013;31(37).

Guideng et al., T cell antigen discovery via trogocytosis. Nature Methods. Feb. 2019;16(2):183-90.

Hastie et al., Understanding and altering cell tropism of vesicular stomatitis virus. Virus Res. Sep. 2013;176(1-2):16-32. doi: 10.1016/j.virusres.2013.06.003. Epub Jun. 22, 2013.

Ho et al., Decoupling the Functional Pleiotropy of Stem Cell Factor by Tuning c-Kit Signaling. Cell. Mar. 9, 2017;168(6):1041-1052. e18. doi: 10.1016/j.cell.2017.02.011.

Höfig et al., Systematic improvement of lentivirus transduction protocols by antibody fragments fused to VSV-G as envelope glycoprotein. Biomaterials. Apr. 2014;35(13):4204-12. doi: 10.1016/j.biomaterials.2014.01.051. Epub Feb. 12, 2014.

Joglekar et al., T cell antigen discovery via signaling and antigen-presenting bifunctional receptors. Nature Methods. Sep. 23, 2019;16(2):191-8.

Kameyama et al., Antibody-dependent gene transduction using gammaretroviral and lentiviral vectors pseudotyped with chimeric vesicular stomatitis virus glycoprotein. J Virol Methods. Oct. 2008;153(1):49-54.

Karlin et al., Applications and statistics for multiple high-scoring segments in molecular sequences. Proc Natl Acad Sci U S A. Jun. 15, 1993;90(12):5873-7.

Karlin et al., Methods for assessing the statistical significance of molecular sequence features by using general scoring schemes. Proc Natl Acad Sci U S A. Mar. 1990;87(6):2264-8.

Knopp et al., Transient Retrovirus-Based CRISPR/Cas9 All-in-One Particles for Efficient, Targeted Gene Knockout. Mol Ther Nucleic Acids. Dec. 7, 2018;13:256-274. doi: 10.1016/j.omtn.2018.09.006. Epub Sep. 13, 2018.

Kussie et al., A single engineered amino acid substitution changes antibody fine specificity. J Immunol. Jan. 1, 1994;152(1):146-52.

Lombardo et al., Gene editing in human stem cells using zinc finger nucleases and integrase-defective lentiviral vector delivery. Nat Biotechnol. Nov. 2007;25(11):1298-306. doi: 10.1038/nbt1353. Epub Oct. 28, 2007.

Milani et al., Genome editing for scalable production of alloantigen-free lentiviral vectors for in vivo gene therapy. EMBO Mol Med. Nov. 2017;9(11):1558-1573.

Nikolic et al., Structural basis for the recognition of LDL-receptor family members by VSV glycoprotein. Nat Commun. Mar. 12, 2018;9(1):1029. doi: 10.1038/s41467-018-03432-4.

Ou et al., Specific targeting of human interleukin (IL)-13 receptor α2-positive cells with lentiviral vectors displaying IL-13. Hum Gene Ther Methods. Apr. 2012;23(2):137-47. doi: 10.1089/hgtb.2012.054. Epub May 21, 2012.

Peach et al., Both extracellular immunoglobin-like domains of CD80 contain residues critical for binding T cell surface receptors CTLA-4 and CD28. J Biol Chem. Sep. 8, 1995;270(36):21181-7.

Sela-Culang et al., The structural basis of antibody-antigen recognition. Front Immunol. Oct. 8, 2013;4:302.

Sevier et al., Efficient export of the vesicular stomatitis virus G protein from the endoplasmic reticulum requires a signal in the cytoplasmic tail that includes both tyrosine-based and di-acidic motifs. Mol Biol Cell. Jan. 2000;11(1):13-22.

Sirin et al., AB-Bind: Antibody binding mutational database for computational affinity predictions. Protein Sci. Feb. 2016;25(2):393-409. doi: 10.1002/pro.2829. Epub Nov. 6, 2015.

Taube et al., Lentivirus display: stable expression of human antibodies on the surface of human cells and virus particles. PLoS One. Sep. 11, 2008;3(9):e3181.

Urban et al., Retroviral display in gene therapy, protein engineering, and vaccine development. ACS Chem Biol. Jan. 21, 2011;6(1):61-74. doi: 10.1021/cb100285n. Epub Dec. 20, 2010.

Urban et al., Selection of functional human antibodies from retroviral display libraries. Nucleic Acids Res. Feb. 24, 2005;33(4):e35.

Winkler et al., Changing the antigen binding specificity by single point mutations of an anti-p24 (HIV-1) antibody. J Immunol. Oct. 15, 2000;165(8):4505-14.

Yang et al., Cell type-specific targeting with surface-engineered lentiviral vectors co-displaying OKT3 antibody and fusogenic molecule. Pharm Res. Jun. 2009;26(6):1432-45. doi: 10.1007/s11095-009-9853-y. Epub Mar. 4, 2009.

Yang et al., Targeting lentiviral vectors to specific cell types in vivo. PNAS. Aug. 1, 2006;103(31):11479-84.

(56)                 References Cited

OTHER PUBLICATIONS

Yu et al., Engineered cell entry links receptor biology with single-cell genomics. Cell. Dec. 22, 2022;185(26):4904-4920.e22. doi: 10.1016/j.cell.2022.11.016. Epub Dec. 13, 2022.

Zhang et al., Cell-specific targeting of lentiviral vectors mediated by fusion proteins derived from Sindbis virus, vesicular stomatitis virus, or avian sarcoma/leukosis virus. Retrovirology. Jan. 25, 2010;7:3.

Zhang et al., Leucine-rich repeat-containing G protein-coupled receptor 4 facilitates vesicular stomatitis virus infection by binding vesicular stomatitis virus glycoprotein. J Biol Chem. Oct. 6, 2017;292(40):16527-16538. doi: 10.1074/jbc.M117.802090. Epub Aug. 23, 2017.

Cell Entry (GFP Expression)

Cell Entry (GFP Expression)

FIG. 5A

T cell Activation

Cell Entry

Cell Entry (GFP Expression)

Cell Entry (GFP Expression)

Measles (MV)    Nipah (NIV)    VSV

αCD19
scFv

Raji (CD19⁺)    Jurkat (CD19⁻)

GFP Expression (infection reporter)

TCR-independent
infection

TCR-Targeted

MFI for CD69:          ~5,500          ~32,000

10uL GL9 Virus    10uL NYESO Virus

Primary T cells
Specific to GL9

26 pM 1G4 cell line
Specific to NYESO-1

GFP

H57                    C11                    VSVwt

GFP (Viral Entry)

Raji (B Cell)          Jurkat (T Cell)

VSVdead aCD19

Cocaldead aCD19

GFP (Viral Entry)

SEQUENCE LISTING

Sequence total quantity: 54
SEQ ID NO: 1              moltype = AA   length = 20
FEATURE                   Location/Qualifiers
REGION                    1..20
                          note = Synthetic Polypeptide
source                    1..20
                          mol_type = protein
                          organism = synthetic construct
SEQUENCE: 1
METDTLLLWV LLLWVPGSTG                                                20

SEQ ID NO: 2              moltype = AA   length = 20
FEATURE                   Location/Qualifiers
REGION                    1..20
                          note = Synthetic Polypeptide
source                    1..20
                          mol_type = protein
                          organism = synthetic construct
SEQUENCE: 2
MSRSVALAVL ALLSLSGLEA                                                20

SEQ ID NO: 3              moltype = AA   length = 19
FEATURE                   Location/Qualifiers
REGION                    1..19
                          note = Synthetic Polypeptide
source                    1..19
                          mol_type = protein
                          organism = synthetic construct
SEQUENCE: 3
AVGQDTQEVI VVPHSLPFK                                                 19

SEQ ID NO: 4              moltype = AA   length = 49
FEATURE                   Location/Qualifiers
REGION                    1..49
                          note = Synthetic Polypeptide
source                    1..49
                          mol_type = protein
                          organism = synthetic construct
SEQUENCE: 4
ASAKPTTTPA PRPPTPAPTI ASQPLSLRPE AARPAAGGAV HTRGLDFAK               49

SEQ ID NO: 5              moltype = AA   length = 6
FEATURE                   Location/Qualifiers
REGION                    1..6
                          note = Synthetic Polypeptide
source                    1..6
                          mol_type = protein
                          organism = synthetic construct
SEQUENCE: 5
GAPGAS                                                               6

SEQ ID NO: 6              moltype = AA   length = 17
FEATURE                   Location/Qualifiers
REGION                    1..17
                          note = Synthetic Polypeptide
source                    1..17
                          mol_type = protein
                          organism = synthetic construct
SEQUENCE: 6
GAPGSGGGGS GGGGSAS                                                   17

SEQ ID NO: 7              moltype = AA   length = 5
FEATURE                   Location/Qualifiers
REGION                    1..5
                          note = Synthetic Polypeptide
source                    1..5
                          mol_type = protein
                          organism = synthetic construct -continued

```
SEQUENCE: 7
GGGGS                                                                    5

SEQ ID NO: 8              moltype = AA  length = 33
FEATURE                  Location/Qualifiers
REGION                   1..33
                         note = Synthetic Polypeptide
source                   1..33
                         mol_type = protein
                         organism = synthetic construct
SEQUENCE: 8
ASESKYGPPC PPCPAVGQDT QEVIVVPHSL PFK                                     33

SEQ ID NO: 9              moltype = AA  length = 39
FEATURE                  Location/Qualifiers
REGION                   1..39
                         note = Synthetic Polypeptide
source                   1..39
                         mol_type = protein
                         organism = synthetic construct
SEQUENCE: 9
ASGGGGSGEL AAIKQELAAI KKELAAIKWE LAAIKQGAG                               39

SEQ ID NO: 10             moltype = AA  length = 14
FEATURE                  Location/Qualifiers
REGION                   1..14
                         note = Synthetic Polypeptide
source                   1..14
                         mol_type = protein
                         organism = synthetic construct
SEQUENCE: 10
ASESKYGPPC PPCP                                                          14

SEQ ID NO: 11             moltype = DNA  length = 1536
FEATURE                  Location/Qualifiers
misc_feature             1..1536
                         note = Synthetic Polynucleotide
source                   1..1536
                         mol_type = other DNA
                         organism = synthetic construct
SEQUENCE: 11
atgaagtgcc ttttgtactt agccttttta ttcattgggg tgaattgcaa gttcaccata      60
gtttttccac acaaccaaaa aggaaactgg aaaaatgttc cttctaatta ccattattgc     120
ccgtcaagct cagatttaaa ttggcataat gacttaatag gcacagccat acaagtcaaa     180
atgcccaaga gtcacaaggc tattcaagca gacggttgga tgtgtcatgc ttccaaatgg     240
gtcactactt gtgatttccg ctggtatgga ccgaagtata taacacagtc catccgatcc     300
ttcactccat ctgtagaaca atgcaaggaa agcattgaac aaacgaaaca aggaacttgg     360
ctgaatccag gcttccctcc tcaaagttgt ggatatgcaa ctgtgacgga tgccgaagca     420
gtgattgtcc aggtgactcc tcaccatgtg ctggttgatg aatacacagg agaatgggtt     480
gattcacagt tcatcaacgg aaaatgcagc aattacatat gccccactgt ccataactct     540
acaacctggc attctgacta taaggtcaaa gggctatgtg attctaacct catttccatg     600
gacatcacct tcttctcaga ggacggagag ctatcatccc tgggaaagga gggcacaggg     660
ttcagaagta actactttgc ttatgaaact ggaggcaagg cctgcaaaat gcaatactgc     720
aagcattggg gagtcagact cccatcaggt gtctggttcg agatggctga taaggatctc     780
tttgctgcag ccagattccc tgaatgccca gaagggtcaa gtatctctgc tccatctcag     840
acctcagtgg atgtaagtct aattcaggac gttgagagga tcttggatta ttccctctgc     900
caagaaacct ggagcaaaat cagagcgggt cttccaatct ctccagtgga tctcagctat     960
cttgctccta aaaacccagg aaccggtcct gctttcacca taatcaatgg taccctaaaa    1020
tactttgaga ccagatacat cagagtcgat attgctgctc caatcctctc aagaatggtc    1080
ggaatgatca gtggaactac cacagaaagg gaactgtggg atgactgggc accatatgaa    1140
gacgtggaaa ttggacccaa tggagttctg aggaccagtt caggatataa gtttcctttta   1200
tacatgattg gacatggtat gttggactcc gatcttcatc ttagctcaaa ggctcaggtg    1260
ttcgaacatc ctcacattca agacgctgct tcgcaacttc ctgatgatga gagtttattt    1320
tttggtgata ctgggctatc caaaaatcca atcgagcttg tagaaggttg gttcagtagt    1380
tggaaaagct ctattgcctc ttttttcttt atcatagggt taatcattgg actattcttg    1440
gttctccgag ttggtatcca tcttttgcatt aaattaaagc acaccaagaa aagacagatt   1500
tatacagaca tagagatgaa ccgacttgga aagtaa                                1536

SEQ ID NO: 12             moltype = AA  length = 511
FEATURE                  Location/Qualifiers
REGION                   1..511
                         note = Synthetic Polypeptide
source                   1..511
                         mol_type = protein
                         organism = synthetic construct
SEQUENCE: 12
MKCLLYLAFL FIGVNCKFTI VFPHNQKGNW KNVPSNYHYC PSSSDLNWHN DLIGTAIQVK       60
MPKSHKAIQA DGWMCHASKW VTTCDFRWYG PKYITQSIRS FTPSVEQCKE SIEQTKQGTW      120
LNPGFPPQSC GYATVTDAEA VIVQVTPHHV LVDEYTGEWV DSQFINGKCS NYICPTVHNS      180
```

-continued

```
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                 511
```

```
SEQ ID NO: 13              moltype = AA  length = 495
FEATURE                    Location/Qualifiers
REGION                     1..495
                           note = Synthetic Polypeptide
source                     1..495
                           mol_type = protein
                           organism = synthetic construct
SEQUENCE: 13
KFTIVFPHNQ KGNWKNVPSN YHYCPSSSDL NWHNDLIGTA IQVKMPKSHK AIQADGWMCH  60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495
```

```
SEQ ID NO: 14              moltype = DNA  length = 1536
FEATURE                    Location/Qualifiers
misc_feature               1..1536
                           note = Synthetic Polynucleotide
source                     1..1536
                           mol_type = other DNA
                           organism = synthetic construct
SEQUENCE: 14
atgaagtgcc ttttgtactt agccttttta ttcattgggg tgaattgcaa gttcaccata  60
gtttttccac acaaccaaaa aggaaactgg aaaaatgttc cttctaatta ccattattgc  120
ccgtcaagct cagatttaaa ttggcataat gacttaatag gcacagcctt acaagtcaaa  180
atgccccaga gtcacaaggc tattcaagca gacggttgga tgtgtcatgc ttccaaatgg  240
gtcactactt gtgatttccg ctggtatgga ccgaagtata taacacagtc catccgatcc  300
ttcactccat ctgtagaaca atgcaaggaa agcattgaac aaacgaaaca aggaacttgg  360
ctgaatccag gcttccctcc tcaaagttgt ggatatgcaa ctgtgacgga tgccgaagca  420
gtgattgtcc aggtgactcc tcaccatgtg ctggttgatg aatacacagg agaatgggtt  480
gattcacagt tcatcaacgg aaaatgcagc aattacatat gccccactgt ccataactct  540
acaacctggc attctgacta taaggtcaaa gggctatgtg attctaacct catttccatg  600
gacatcacct tcttctcaga ggacggagag ctatcatccc tgggaaagga gggcacaggg  660
ttcagaagta actactttgc ttatgaaact ggaggcaagg cctgcaaaat gcaatactgc  720
aagcattggg gagtcagact cccatcaggt gtctggttcg agatggctga taaggatctc  780
tttgctgcag ccagattccc tgaatgccca gaagggtcaa gtatctctgc tccatctcag  840
acctcagtgg atgtaagtct aattcaggac gttgagagga tcttggatta ttccctctgc  900
caagaaacct ggagcaaaat cagagcgggt cttccaatct ctccagtgga tctcagctat  960
cttgctccta aaaacccagg aaccggtcct gctttcacca taatcaatgg taccctaaaa  1020
tactttgaga ccagatacat cagagtcgat attgctgctc caatcctctc aagaatggtc  1080
ggaatgatca gtggaactac cacagaagcc gaactgtggg atgactgggc accatatgaa  1140
gacgtggaaa ttggacccaa tggagttctg aggaccagtt caggatataa gtttccttta  1200
tacatgattg acatggtat gttggactcc gatcttcatc ttagctcaaa ggctcaggtg  1260
ttcgaacatc ctcacattca agacgctgct cgcaacttct ctgatgatga gagtttattt  1320
tttggtgata ctgggctatc caaaaatcca atcgagcttg tagaaggttg gttcagtagt  1380
tggaaaagct ctattgcctc ttttttcttt atcatagggt taatcattgg actattcttg  1440
gttctccgag ttggtatcca tctttgcatt aaattaaagc acaccaagaa aagacagatt  1500
tatacagaca tagagatgaa ccgacttgga aagtaa                            1536
```

```
SEQ ID NO: 15              moltype = AA  length = 511
FEATURE                    Location/Qualifiers
REGION                     1..511
                           note = Synthetic Polypeptide
source                     1..511
                           mol_type = protein
                           organism = synthetic construct
SEQUENCE: 15
MKCLLYLAFL FIGVNCKFTI VFPHNQKGNW KNVPSNYHYC PSSSDLNWHN DLIGTALQVK  60
MPQSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTEA ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                 511
```

```
SEQ ID NO: 16              moltype = AA  length = 495
```

```
FEATURE               Location/Qualifiers
REGION                1..495
                      note = Synthetic Polypeptide
source                1..495
                      mol_type = protein
                      organism = synthetic construct
SEQUENCE: 16
KFTIVFPHNQ KGNWKNVPSN YHYCPSSSDL NWHNDLIGTA LQVKMPQSHK AIQADGWMCH   60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 17          moltype = AA  length = 495
FEATURE               Location/Qualifiers
REGION                1..495
                      note = Synthetic Polypeptide
source                1..495
                      mol_type = protein
                      organism = synthetic construct
SEQUENCE: 17
KFTIVFPHNQ KGNWKNVPSN YHYCPSSSDL NWHNDLIGTA IQVKMPQSHK AIQADGWMCH   60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 18          moltype = AA  length = 1818
FEATURE               Location/Qualifiers
REGION                1..1818
                      note = Synthetic Polypeptide
source                1..1818
                      mol_type = protein
                      organism = synthetic construct
SEQUENCE: 18
ATGGGCAGCC GGATCGTGAT CAACCGGGAG CACCTGATGA TCGACCGGCC CTACGTGCTG   60
CTGGCCGTGC TGTTCGTGAT GTTCCTGAGC CTGATCGGCT TGCTAGCCAT TGCTGGAATC  120
CGGCTGCACA GAGCCGCCAT CTACACCGCC GAGATCCACA AGAGCCTGAG CACCAACCTG  180
GACGTGACCA ACAGCATCGA GCATCAGGTC AAGGACGTGC TACCCCCCT GTTTAAGATC  240
ATCGGCGACG AAGTGGGCCT GCGGACCCCC CAGAGATTCA CCGACCTGGT CAAGTTCATC  300
AGCGACAAGA TCAAGTTCCT GAACCCCGAC CGGGAGTACG ACTTCCGGGA CCTGACCTGG  360
TGCATCAACC CCCCCGAGCG GATCAAGCTG GACTACGACC AGTACTGCGC CGATGTGGCC  420
GCCGAGGAAC TGATGAATGC ATTGGTGAAC TCAACTCTAC TGGAGACCAG AACAACCAAT  480
CAGTTCCTAG CTGTCTCAAA GGGAAACTGC TCAGGGCCCA CTACAATCAG AGGTCAATTC  540
TCAAACATGT CGCTGTCCCT GTTAGACTTG TATTTAGGTC GAGGTTACAA TGTGTCATCT  600
ATAGTCACTA TGACATCCCA GGGAATGTAT GGGGGAACTT ACCTAGTGGA AAAGCCTAAT  660
CTGAGCAGCA AAAGGTCAGA GTTGTCACAA CTGAGCATGT ACCGAGTGTT TGAAGTAGGT  720
GTTATCAGAA ATCCGGGTTT GGGGGCTCCG GTGTTCCATA TGACAAACTA TCTTGAGCAA  780
CCAGTCAGTA ATGATCTCAG CAACTGTATG GTGGCTTTGG GGGAGCTCAA ACTCGCAGCC  840
CTTTGTCACG GGGAAGATTC TATCACAATT CCCTATCAGG GATCAGGGAA AGGTGTCAGC  900
TTCCAGCTCG TCAAGCTAGG TGTCTGGAAA TCCCCAACCG ACATGCAATC CTGGGTCCCC  960
TTATCAACGG ATGATCCAGT GATAGACAGG CTTTACCTCT CATCTCACAG AGGTGTTATC 1020
GCTGACAACC AAGCAAAATG GGCTGTCCCG ACAACACGAA CAGATGACAA GTTGCGAATG 1080
GAGACATGCT TCCAACAGGC GTGTAAGGGT AAAATCCAAG CACTCTGCGA GAATCCCGAG 1140
TGGGCACCAT TGAAGGATAA CAGGATTCCT TCATACGGGG TCTTGTCTGT TGATCTGAGT 1200
CTGACAGTTG AGCTTAAAAT CAAAATTGCT TCGGGATTCG GGCCATTGAT CACACACGGT 1260
TCAGGGATGG ACCTATACAA ATCCAACCAC AACAATGTGT ATTGGCTGAC TATCCCGCCA 1320
ATGAAGAACC TAGCCTTAGG TGTAATCAAC ACATTGGAGT GGATACCGAG ATTCAAGGTT 1380
AGTCCCTATC TCTTCACAGT CCCAATTAAG GAAGCAGGCG AGACTGCCA TGCCCCAACA 1440
TACCTACCTG CGGAGGTGGA TGGTGATGTC AAACTCAGTT CCAATCTGGT GATTCTACCT 1500
GGTCAAGATC TCCAATATGT TTTGGCAACC TACGATACTT CCCGGGTTGA ACATGCTGTG 1560
GTTTATTACG TTTACAGCCC AAGCCGCTCA TTTTCTTACT TTATCCTTT TAGGTTGCCT 1620
ATAAAGGGGG TCCCCATCGA ATTACAAGTG GAATGCTTCA CATGGGACCA AAAACTCTGG 1680
TGCCGTCACT TCTGTGTGCT TGCGGACTCA GAATCTGGTG ACATATCAC TCACTCTGGG 1740
ATGGTGGGCA TGGGAGTCAG CTGCACAGTC ACCCGGGAAG ATGGAACCAA TGACTACAAA 1800
GACGATGACG ACAAGTGA                                               1818

SEQ ID NO: 19          moltype = AA  length = 605
FEATURE               Location/Qualifiers
REGION                1..605
                      note = Synthetic Polypeptide
```

```
source                    1..605
                          mol_type = protein
                          organism = synthetic construct
SEQUENCE: 19
MGSRIVINRE HLMIDRPYVL LAVLFVMFLS LIGLLAIAGI RLHRAAIYTA EIHKSLSTNL    60
DVTNSIEHQV KDVLTPLFKI IGDEVGLRTP QRFTDLVKFI SDKIKFLNPD REYDFRDLTW   120
CINPPERIKL DYDQYCADVA AEELMNALVN STLLETRTTN QFLAVSKGNC SGPTTIRGQF   180
SNMSLSLLDL YLGRGYNVSS IVTMTSQGMY GGTYLVEKPN LSSKRSELSQ LSMYRVFEVG   240
VIRNPGLGAP VFHMTNYLEQ PVSNDLSNCM VALGELKLAA LCHGEDSITI PYQGSGKGVS   300
FQLVKLGVWK SPTDMQSWVP LSTDDPVIDR LYLSSHRGVI ADNQAKWAVP TTRTDDKLRM   360
ETCFQQACKG KIQALCENPE WAPLKDNRIP SYGVLSVDLS LTVELKIKIA SGFGPLITHG   420
SGMDLYKSNH NNVYWLTIPP MKNLALGVIN TLEWIPRFKV SPYLFTVPIK EAGGDCHAPT   480
YLPAEVDGDV KLSSNLVILP GQDLQYVLAT YDTSRVEHAV VYVVYSPSRS FSYFYPFRLP   540
IKGVPIELQV ECFTWDQKLW CRHFCVLADS ESGGHITHSG MVGMGVSCTV TREDGTNDYK   600
DDDDK                                                              605

SEQ ID NO: 20             moltype = AA  length = 1818
FEATURE                   Location/Qualifiers
REGION                    1..1818
                          note = Synthetic Polypeptide
source                    1..1818
                          mol_type = protein
                          organism = synthetic construct
SEQUENCE: 20
ATGGGCAGCC GGATCGTGAT CAACCGGGAG CACCTGATGA TCGACCGGCC CTACGTGCTG    60
CTGGCCGTGC TGTTCGTGAT GTTCCTGAGC CTGATCGGCT TGCTAGCCAT TGCTGGAATC   120
CGGCTGCACA GAGCCGCCAT CTACACCGCC GAGATCCACA AGAGCCTGAG CACCAACCTG   180
GACGTGACCA ACAGCATCGA GCATCAGGTC AAGGACGTGC TGACCCCCCT GTTTAAGATC   240
ATCGGCACGG AAGTGGGCCT GCGGACCCCC CAGAGATTCA CCGACCTGGT CAAGTTCATC   300
AGCGACAAGA TCAAGTTCCT GAACCCCGAC CGGGAGTACG ACTTCCGGGA CCTGACCTGG   360
TGCATCAACC CCCCCGAGCG GATCAAGCTG GACTACGACC AGTACTGCGC CGATGTGGCC   420
GCCGAGGAAC TGATGAATGC ATTGGTGAAC TCAACTCTAC TGGAGACCAG AACAACCAAT   480
CAGTTCCTAG CTGTCTCAAA GGGAAACTGC TCAGGGCCCA CTACAATCAG AGGTCAATTC   540
TCAAACATGT CGCTGTCCCT GTTAGACTTG TATTTAGGTC GGGGTTACAA TGTGTCATCT   600
ATAGTCACTA TGACATCCCA GGGAATGTAT GGGGGAACTT ACCTAGTGGA AAAGCCTAAT   660
CTGAGCAGCA AAAGGTCAGA GTTGTCACAA CTGAGCATGT ACCGAGTGTT TGAAGTAGGT   720
GTTATCGAAA ATCCGGGTTT GGGGGCTCCG GTGTTCCATA TGACAAACTA TCTTGAGCAA   780
CCAGTCAGTA ATGATCTCAG CAACTGTATG GTGGCTTTGG GGGAGCTCAA ACTCGCAGCC   840
CTTTGTCACG GGGAAGATTC TATCACAATT CCCTATCAGG GATCAGGGAA AGGTGTCAGC   900
TTCCAGCTCG TCAAGCTAGG TGTCTGGAAA TCCCCAACCG ACATGCAATC CTGGGTCCCC   960
TTATCAACGG ATGATCCAGT GATAGACAGG CTTTACCTCT CATCTCACAG AGGTGTTATC  1020
GCTGACAACC AAGCAAAATG GGCTGTCCCG ACAACACGAA CAGATGACAA GTTGCGAATG  1080
GAGACATGCT TCCAACAGGC GTGTAAGGGT AAAATCCAAG CACTCTGCGA GAATCCCGAG  1140
TGGGCACCAT TGAAGGATAA CAGGATTCCT TCATACGGGG TCTTGTCTGT TGATCTGAGT  1200
CTGACAGTTG AGCTTAAAAT CAAAATTGCT TCGGGATTCG GGCCATTGAT CACACACGGT  1260
TCAGGGATGG ACCTATACAA ATCCAACCAC AACAATGTGT ATTGGCTGAC TATCCCGCCA  1320
ATGAAGAACC TAGCCTTAGG TGTAATCAAC ACATTGGAGT GGATACCGAG ATTCAAGGTT  1380
AGTCCCGCGC TCTTCAATGT CCCAATTAAG GAAGCAGGCG GAGACTGCCA TGCCCCAACA  1440
TACCTACCTG CGGAGGTGGA TGGTGATGTC AAACTCAGTT CCAATCTGGT GATTCTACCT  1500
GGTCAAGATC TCCAATATGT TTTGGCAACC TACGATACTT CCGCGGTTGA ACATGCTGTG  1560
GTTTATTACG TTTACAGCCC AAGCCGCTCA TTTTCTTACT TTTATCCTTT TAGGTTGCCT  1620
ATAAAGGGGG TCCCCATCGA ATTACAAGTG GAATGCTTCA CATGGGACCA AAAACTCTGG  1680
TGCCGTCACT TCTGTGTGCT TGCGGACTCA GAATCTGGTG GACATATCAC TCACTCTGGG  1740
ATGGTGGGCA TGGGAGTCAG CTGCACAGTC ACCCGGGAAG ATGGAACCAA TGACTACAAA  1800
GACGATGACG ACAAGTGA                                                1818

SEQ ID NO: 21             moltype = AA  length = 605
FEATURE                   Location/Qualifiers
REGION                    1..605
                          note = Synthetic Polypeptide
source                    1..605
                          mol_type = protein
                          organism = synthetic construct
SEQUENCE: 21
MGSRIVINRE HLMIDRPYVL LAVLFVMFLS LIGLLAIAGI RLHRAAIYTA EIHKSLSTNL    60
DVTNSIEHQV KDVLTPLFKI IGDEVGLRTP QRFTDLVKFI SDKIKFLNPD REYDFRDLTW   120
CINPPERIKL DYDQYCADVA AEELMNALVN STLLETRTTN QFLAVSKGNC SGPTTIRGQF   180
SNMSLSLLDL YLGRGYNVSS IVTMTSQGMY GGTYLVEKPN LSSKRSELSQ LSMYRVFEVG   240
VIRNPGLGAP VFHMTNYLEQ PVSNDLSNCM VALGELKLAA LCHGEDSITI PYQGSGKGVS   300
FQLVKLGVWK SPTDMQSWVP LSTDDPVIDR LYLSSHRGVI ADNQAKWAVP TTRTDDKLRM   360
ETCFQQACKG KIQALCENPE WAPLKDNRIP SYGVLSVDLS LTVELKIKIA SGFGPLITHG   420
SGMDLYKSNH NNVYWLTIPP MKNLALGVIN TLEWIPRFKV SPALFNVPIK EAGGDCHAPT   480
YLPAEVDGDV KLSSNLVILP GQDLQYVLAT YDTSAVEHAV VYVVYSPSRS FSYFYPFRLP   540
IKGVPIELQV ECFTWDQKLW CRHFCVLADS ESGGHITHSG MVGMGVSCTV TREDGTNDYK   600
DDDDK                                                              605

SEQ ID NO: 22             moltype = AA  length = 1785
FEATURE                   Location/Qualifiers
REGION                    1..1785
```

```
                              note = Synthetic Polypeptide
source                        1..1785
                              mol_type = protein
                              organism = synthetic construct
SEQUENCE: 22
ATGAAGAAGA TCAACGAGGG CCTGCTGGAC AGCAAGATCC TGAGCGCCTT CAACACCGTG   60
ATTGCCCTGC TGGGCTCTAT CGTGATCATC GTGATGAACA TCATGATCAT CCAGAACTAC   120
ACCCGGTCCA CCGACAACCA GGCCGTGATT AAGGATGCTC TGCAGGGAAT CCAGCAGCAG   180
ATCAAAGGCC TGGCCGACAA GATCGGCACA GAGATCGGCC CTAAGGTGTC CCTGATCGAC   240
ACCAGCAGCA CCATCACAAT CCCCGCCAAT ATCGGACTGC TGGGAAGCAA GATCAGCCAG   300
AGCACCGCCA GCATCAACGA GAACGTGAAC GAGAAGTGCA AGTTCACCCT GCCTCCACTG   360
AAGATCCACG AGTGCAACAT CAGCTGCCCC AATCCTCTGC CATTCAGAGA GTACAGACCC   420
CAGACAGAGG GCGTGTCCAA TCTCGTGGGC CTGCCTAACA ACATCTGCCT GCAGAAAACT   480
AGCAACCAGA TCCTGAAGCC TAAGCTGATC TCCTACACAC TGCCCGTCGT GGGCCAGAGC   540
GGCACCTGTA TTACAGATCC TCTGCTGGCC ATGGACGAGG GCTACTTTGC CTACAGCCAC   600
CTGGAAAGAA TCGGCAGCTG TAGCCGGGGA GTGTCCAAGC AGAGAATCAT CGGCGTGGGC   660
GAAGTGCTGG ATAGAGGCGA CGAAGTGCCC AGCCTGTTCA TGACCAATGT GTGGACCCCT   720
CCTAATCCTA ACACCGTGTA CCACTGCAGC GCCGTGTACA ACAACGAGTT CTACTACGTG   780
CTGTGCGCCG TGTCCACAGT GGGCGACCCT ATCCTGAACA GCACCTATTG GAGCGGCAGC   840
CTGATGATGA CCAGACTGGC CGTGAAGCCC AAGAGCAATG GCGGCGGATA CAACCAGCAT   900
CAGCTGGCCC TGCGGTCCAT CGAGAAGGGC AGATACGACA AAGTGATGCC TTACGGCCCC   960
AGCGGCATCA AGCAAGGCGA TACCCTGTAC TTTCCCGCCG TGGGATTTCT CGTGCGGACC   1020
GAGTTCAAGT ACAACGACAG CAACTGCCCC ATCACCAAGT GCCAGTACAG CAAGCCCGAG   1080
AACTGCAGAC TGAGCATGGG CATCAGACCC AACAGCCACT ACATCCTGAG AAGCGGCCTG   1140
CTGAAGTACA ACCTGAGCGA CGGCGAGAAC CCCAAGGTGG TGTTCATCGA GATCAGCGAC   1200
CAGCGGCTGT CTATCGGCAG CCCCTCCAAG ATCTACGACT CTCTGGGCCA GCCAGTGTTC   1260
TACCAGGCCA GCTTTAGCTG GGACACCATG ATCAAGTTCG GCGACGTGCT GACCGTGAAT   1320
CCCCTGGTGG TCAACTGGCG GAACAATACC GTGATCAGCC GGCCTGGCCA GTCTCAGTGC   1380
CCCAGATTCA ATACCTGTCC TGCCATTTGC GCCGAAGGCG TGTACAATGA CGCCTTCCTG   1440
ATCGATCGGA TCAACTGGAT CTCTGCCGGC GTGTTCCTGG ACTCTAATGC CACAGCCGCC   1500
AATCCTGTGT TCACCGTGTT CAAGGACAAT GAGATCCTGT ATCGGGCCCA GCTGGCCTCC   1560
GAGGACACAA ATGCCCAGAA AACAATCACC AACTGCTTTC TGCTCAAGAA CAAGATCTGG   1620
TGCATCAGCC TGGTGGAAAT CTACGACACC GGCGACAACG TGATCAGGCC CAAGCTGTTC   1680
GCCGTGAAGA TCCCTGAGCA GTGTACAGGC GGCGGAGGCT CTGGCGGAGG TGGAAGCGGA   1740
GGCGGTGGAT CTGCTAGCGA TTACAAGGAT GACGACGATA AGTGA               1785

SEQ ID NO: 23                 moltype = AA   length = 594
FEATURE                       Location/Qualifiers
REGION                        1..594
                              note = Synthetic Polypeptide
source                        1..594
                              mol_type = protein
                              organism = synthetic construct
SEQUENCE: 23
MKKINEGLLD SKILSAFNTV IALLGSIVII VMNIMIIQNY TRSTDNQAVI KDALQGIQQQ   60
IKGLADKIGT EIGPKVSLID TSSTITIPAN IGLLGSKISQ STASINENVN EKCKFTLPPL   120
KIHECNISCP NPLPFREYRP QTEGVSNLVG LPNNICLQKT SNQILKPKLI SYTLPVVGQS   180
GTCITDPLLA MDEGYFAYSH LERIGSCSRG VSKQRIIGVG EVLDRGDEVP SLFMTNVWTP   240
PNPNTVYHCS AVYNNEFYYV LCAVSTVGDP ILNSTYWSGS LMMTRLAVKP KSNGGGYNQH   300
QLALRSIEKG RYDKVMPYGP SGIKQGDTLY FPAVGFLVRT EFKYNDSNCP ITKCQYSKPE   360
NCRLSMGIRP NSHYILRSGL LKYNLSDGEN PKVVFIEISD QRLSIGSPSK IYDSLGQPVF   420
YQASFSWDTM IKFGDVLTVN PLVVNWRNNT VISRPGQSQC PRFNTCPAIC AEGVYNDAFL   480
IDRINWISAG VFLDSNATAA NPVFTVFKDN EILYRAQLAS EDTNAQKTIT NCFLLKNKIW   540
CISLVEIYDT GDNVIRPKLF AVKIPEQCTG GGGSGGGGSG GGGSASDYKD DDDK       594

SEQ ID NO: 24                 moltype = AA   length = 609
FEATURE                       Location/Qualifiers
REGION                        1..609
                              note = Synthetic Polypeptide
source                        1..609
                              mol_type = protein
                              organism = synthetic construct
SEQUENCE: 24
MSIGLLCCAA LSLLWAGPVN AGVTQTPKFQ VLKTGQSMTL QCAQDMNHEY MSWYRQDPGM   60
GLRLIHYSVG AGITDQGEVP NGYNVSRSTT EDFPLRLLSA APSQTSVYFC ASSYVGNTGE   120
LFFGEGSRLT VLEDLKNVFP PEVAVFEPSE AEISHTQKAT LVCLATGFYP DHVELSWWVN   180
GKEVHSGVST DPQPLKEQPA LNDSRYCLSS RLRVSATFWQ NPRNHFRCQV QFYGLSENDE   240
WTQDRAKPVT QIVSAEAWGR ADCGFTSESY QQGVLSATIL YEILLGKATL YAVLVSALVL   300
MAMVKRKDSR GGSATNFSLL KQAGDVEENP GPMETLLGLL ILWLQLQWVS SKQEVTQIPA   360
ALSVPEGENL VLNCSFTDSA IYNLQWFRQD PGKGLTSLLL IQSSQREQTS GRLNASLDKS   420
SGSSTLYIAA SQPGDSATYL CAVRPTSGGS YIPTFGRGTS LIVHPYIQNP DPAVYQLRDS   480
KSSDKSVCLF TDFDSQTNVS QSKDSDVYIT DKTVLDMRSM DFKSNSAVAW SNKSDFACAN   540
AFNNSIIPED TFFPSPESSC DVKLVEKSFE TDTNLNFQNL SVIGFRILLL KVAGFNLLMT   600
LRLWSSAAA                                                          609

SEQ ID NO: 25                 moltype = AA   length = 609
FEATURE                       Location/Qualifiers
REGION                        1..609
                              note = Synthetic Polypeptide
```

```
source                    1..609
                          mol_type = protein
                          organism = synthetic construct
SEQUENCE: 25
MSIGLLCCAA LSLLWAGPVN AGVTQTPKFQ VLKTGQSMTL QCAQDMNHEY MSWYRQDPGM   60
GLRLIHYSVG AQTTDQGEVP NGYNVSRSTI EDFPLRLLSA APSQTSVYFC ASSYLGNTGE  120
LFFGEGSRLT VLEDLKNVFP PEVAVFEPSE AEISHTQKAT LVCLATGFYP DHVELSWWVN  180
GKEVHSGVST DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSATNFSLL KQAGDVEENP GPMETLLGLL ILWLQLQWVS SKQEVTQIPA  360
ALSVPEGENL VLNCSFTDSA IYNLQWFRQD PGKGLTSLLL IQSSQREQTS GRLNASLDKS  420
SGSSTLYIAA SQPGDSATYL CAVRPMIGGT YIPTFGRGTS LIVHPYIQNP DPAVYQLRDS  480
KSSDKSVCLF TDFDSQTNVS QSKDSDVYIT DKTVLDMRSM DFKSNSAVAW SNKSDFACAN  540
AFNNSIIPED TFFPSPESSC DVKLVEKSFE TDTNLNFQNL SVIGFRILLL KVAGFNLLMT  600
LRLWSSAAA                                                          609

SEQ ID NO: 26          moltype = AA  length = 609
FEATURE                Location/Qualifiers
REGION                 1..609
                       note = Synthetic Polypeptide
source                 1..609
                       mol_type = protein
                       organism = synthetic construct
SEQUENCE: 26
MSIGLLCCAA LSLLWAGPVN AGVTQTPKFQ VLKTGQSMTL QCAQDMNHEY MSWYRQDPGM   60
GLRLIHYSVG AGTTDRGEVP NGYNVSRSTI EDFPLRLLSA APSQTSVYFC ASSYVGDTGE  120
LFFGEGSRLT VLEDLKNVFP PEVAVFEPSE AEISHTQKAT LVCLATGFYP DHVELSWWVN  180
GKEVHSGVST DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSATNFSLL KQAGDVEENP GPMETLLGLL ILWLQLQWVS SKQEVTQIPA  360
ALSVPEGENL VLNCSFTDSA IYNLQWFRQD PGKGLTSLLL IQSSQREQTS GRLNASLDKS  420
SGSSTLYIAA SQPGDSATYL CAVRPLLDGT YIPTFGRGTS LIVHPYIQNP DPAVYQLRDS  480
KSSDKSVCLF TDFDSQTNVS QSKDSDVYIT DKTVLDMRSM DFKSNSAVAW SNKSDFACAN  540
AFNNSIIPED TFFPSPESSC DVKLVEKSFE TDTNLNFQNL SVIGFRILLL KVAGFNLLMT  600
LRLWSSAAA                                                          609

SEQ ID NO: 27          moltype = AA  length = 609
FEATURE                Location/Qualifiers
REGION                 1..609
                       note = Synthetic Polypeptide
source                 1..609
                       mol_type = protein
                       organism = synthetic construct
SEQUENCE: 27
MSIGLLCCAA LSLLWAGPVN AGVTQTPKFQ VLKTGQSMTL QCAQDMNHEY MSWYRQDPGM   60
GLRLIHYSVA IQTTDQGEVP NGYNVSRSTI EDFPLRLLSA APSQTSVYFC ASSYLGNTGE  120
LFFGEGSRLT VLEDLKNVFP PEVAVFEPSE AEISHTQKAT LVCLATGFYP DHVELSWWVN  180
GKEVHSGVST DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR GGSATNFSLL KQAGDVEENP GPMETLLGLL ILWLQLQWVS SKQEVTQIPA  360
ALSVPEGENL VLNCSFTDSA IYNLQWFRQD PGKGLTSLLL ITPWQREQTS GRLNASLDKS  420
SGSSTLYIAA SQPGDSATYL CAVRPLLDGT YIPTFGRGTS LIVHPYIQNP DPAVYQLRDS  480
KSSDKSVCLF TDFDSQTNVS QSKDSDVYIT DKTVLDMRSM DFKSNSAVAW SNKSDFACAN  540
AFNNSIIPED TFFPSPESSC DVKLVEKSFE TDTNLNFQNL SVIGFRILLL KVAGFNLLMT  600
LRLWSSAAA                                                          609

SEQ ID NO: 28          moltype = AA  length = 30
FEATURE                Location/Qualifiers
REGION                 1..30
                       note = Synthetic Polypeptide
source                 1..30
                       mol_type = protein
                       organism = synthetic construct
SEQUENCE: 28
VVVISAILAL VVLTIISLII LIMLWQKKPR                                     30

SEQ ID NO: 29          moltype = AA  length = 60
FEATURE                Location/Qualifiers
REGION                 1..60
                       note = Synthetic Polypeptide
REGION                 7..60
                       note = MISC_FEATURE - may be absent
source                 1..60
                       mol_type = protein
                       organism = synthetic construct
SEQUENCE: 29
GAPGASGAPG ASGAPGASGA PGASGAPGAS GAPGASGAPG ASGAPGASGA PGASGAPGAS   60

SEQ ID NO: 30          moltype = AA  length = 50
```

-continued

```
FEATURE            Location/Qualifiers
REGION             1..50
                   note = Synthetic Polypeptide
REGION             6..50
                   note = MISC_FEATURE - may be absent
source             1..50
                   mol_type = protein
                   organism = synthetic construct
SEQUENCE: 30
GGGGSGGGGS GGGGSGGGGS GGGGSGGGGS GGGGSGGGGS GGGGSGGGGS            50

SEQ ID NO: 31       moltype = AA   length = 603
FEATURE            Location/Qualifiers
REGION             1..603
                   note = Synthetic Polypeptide
source             1..603
                   mol_type = protein
                   organism = synthetic construct
SEQUENCE: 31
MSIGLLCCAA LSLLWAGPVN ADAGVTQSPT HLIKTRGQQV TLRCSPKQGH DTVSWYQQAL    60
GQGPQFIFQY YEEEERQRGN FPDRFSGHQF PNYSSELNVN ALLLGDSALY LCASSDTVSY   120
EQYFGPGTRL TVTEDLKNVF PPEVAVFEPS EAEISHTQKA TLVCLATGFY PDHVELSWWV   180
NGKEVHSGVS TDPQPLKEQP ALNDSRYCLS SRLRVSATFW QDPRNHFRCQ VQFYGLSEND   240
EWTQDRAKPV TQIVSAEAWG RADCGFTSES YQQGVLSATI LYEILLGKAT LYAVLVSALV   300
LMAMVKRKDS RGGSATNFSL LKQAGDVEEN PGPMETLLGL LILWLQLQWV SSKEVEQNSG   360
PLSVPEGAIA SLNCTYSDRG SQSFFWYRQY SGKSPELIMF IYSNGDKEDG RFTAQLNKAS   420
QYISLLIRDS KLSDSATYLC AVRTNSGYAL NFGKGTSLLV TPHIQKPDPA VYQLRDSKSS   480
DKSVCLFTDF DSQTNVSQSK DSDVYITDKT VLDMRSMDFK SNSAVAWSNK SDFACANAFN   540
NSIIPEDTFF PSPESSCDVK LVEKSFETDT NLNFQNLSVI GFRILLLKVA GFNLLMTLRL   600
WSS                                                                603

SEQ ID NO: 32       moltype = DNA   length = 1812
FEATURE            Location/Qualifiers
misc_feature       1..1812
                   note = Synthetic Polynucleotide
source             1..1812
                   mol_type = other DNA
                   organism = synthetic construct
SEQUENCE: 32
atgtctatcg ggctgctgtg ttgcgccgct ctgtccctgc tgtgggccgg acctgtcaat    60
gctgatgctg gcgtaacgca gagcccgaca catctgataa aaacaagagg ccaacaagtt   120
actctgaggt gcagtccaaa gcaagggcac gatactgtgt cttggtacca acaggctctt   180
gggcagggac cacaattcat ctttcaatac tacgaggaag aagagcgcca acgaggaaac   240
tttcctgatc gcttcagcgg tcaccaattt cctaattaca gttccgaatt gaatgtaaat   300
gctctcctgc tcggcgatag cgctctgtac ctttgtgcct cctccgacac cgtaagctat   360
gaacaatact ttggtcctgg cactcgcctc accgtaaccg aagatctgaa gaacgttttt   420
ccgccagagg tcgccgtttt tgaaccaagc gaagcggaaa tcagtcacac acagaaggca   480
acactcgttt gtctggccac tggcttctac cccgatcacg tcgaactttc atggtgggtc   540
aatgaaaagg aagttcacag cggtgtaagt actgatccac agcctctcaa agagcagccc   600
gccttgaatg acagcagata ttgtttgagt tcacggttga gagtaagcgc taccttctgg   660
caagatcctc gcaatcactt ccgatgtcag gtgcagtttt atggactgtc agaaaatgat   720
gaatggacac aagataggc taaacccgtg acccaaatcg tgagcgctga ggcatggggt   780
cgagcagact gcggcttcac aagtgaatca taccagcagg gggtgctgag cgccactatc   840
ctgtacgaga ttctgctggg aaaggctacc ctgtatgcag tgctggtctc cgccctggtg   900
ctgatggcta tggtcaagcg aaaagacagc cggggcgggt ccgcaacaaa cttttccctg   960
ctgaaacagg ccggcgatgt ggaggaaaat cctgggccaa tggagactct gctgggactg  1020
ctgatcctgt ggctgcagct gcagtgggtg tcaagcaaag aagtagaaca aaactcaggc  1080
cccctgtccg taccagaggg agctatagcg tctctcaatt gtacgtacag cgaccggggc  1140
tcccaatcat tcttctggta tcggcagtac agcgggaaaa gtccggaatt gattatgttc  1200
atatattcta acggcgacaa agaggacggg cgatttacgg cacaactgaa caaagcgagc  1260
caatacatca gtcttcttat tcgagatagc aaattgtctg actccgctac atacctctgt  1320
gcagtccgga ctaactccgg ttacgccttg aactttggga aagggacgtc attgttggtc  1380
acgccgcaca tacagaagcc cgatcctgca gtttaccaac tccgggactc aaagtcttcc  1440
gataagagtg tctgtctttt caccgacttc gatagtcaaa cgaatgttag ccagtcaag   1500
gacagcgatg tttatatcac cgacaaaacc gtcctcgaca tgaggtctat ggacttcaag  1560
agcaacagcg cggtagcgtg gtcaaataag agcgactttg cttgcgcgaa cgctttcaat  1620
aattcaatca tacccgagga tactttcttc ccaagtccgg aatctagttg tgacgtgaag  1680
ctggtcgaga aaagtttcga aacagatact aacctgaatt ttcagaacct gtcagtgatc  1740
ggcttccgga ttctgctgct gaaggtcgcc gggttcaatc tgctgatgac cctgagactg  1800
tggtcaagct ga                                                     1812

SEQ ID NO: 33       moltype = AA   length = 609
FEATURE            Location/Qualifiers
REGION             1..609
                   note = Synthetic Polypeptide
source             1..609
                   mol_type = protein
                   organism = synthetic construct
SEQUENCE: 33
```

```
MGTRLLFWVA FCLLGADHTG AGVSQSPSNK VTEKGKDVEL RCDPISGHTA LYWYRQRLGQ    60
GLEFLIYFQG NSAPDKSGLP SDRFSAERTG ESVSTLTIQR TQQEDSAVYL CASSQTQLWE   120
TQYFGPGTRL LVLEDLKNVF PPEVAVFEPS EAEISHTQKA TLVCLATGFY PDHVELSWWV   180
NGKEVHSGVS TDPQPLKEQP ALNDSRYCLS SRLRVSATFW QNPRNHFRCQ VQFYGLSEND   240
EWTQDRAKPV TQIVSAEAWG RADCGFTSES YQQGVLSATI LYEILLGKAT LYAVLVSALV   300
LMAMVKRKDS RGGSATNFSL LKQAGDVEEN PGPMEKNPLA APLLILWFHL DCVSSILNVE   360
QSPQSLHVQE GDSTNFTCSF PSSNFYALHW YRWETAKSPE ALFVMTLNGD EKKKGRISAT   420
LNTKEGYSYL YIKGSQPEDS ATYLCAFITG NQFYFGTGTS LTVIPNIQNP DPAVYQLRDS   480
KSSDKSVCLF TDFDSQTNVS QSKDSDVYIT DKTVLDMRSM DFKSNSAVAW SNKSDFACAN   540
AFNNSIIPED TFFPSPESSC DVKLVEKSFE TDTNLNFQNL SVIGFRILLL KVAGFNLLMT   600
LRLWSSAAA                                                          609

SEQ ID NO: 34            moltype = DNA   length = 1830
FEATURE                  Location/Qualifiers
misc_feature             1..1830
                         note = Synthetic Polynucleotide
source                   1..1830
                         mol_type = other DNA
                         organism = synthetic construct
SEQUENCE: 34
atgggcacac ggttgctgtt ttgggttgct ttctgcctgc tcggcgcaga tcacacggga    60
gcgggggtta gtcagtcccc tagcaataaa gtgacggaaa aagggaaaga tgtcgagctg   120
aggtgtgatc caatttctgg acacactgcc ctctactggt atagacaacg ccttggtcag   180
gggctggagt tccttatcta tttccagggc aactccgcgc ccgacaaaag tggtctcccg   240
agcgaccggt tttcagcgga gcgcacgggt gaaagtgtta gcacactgac aatccaacgg   300
acgcagcagg aggatagtgc tgtttatctg tgtgcctcta gtcagactca actttgggaa   360
actcaatact tcggccctgg tacgcgcctg ctcgttcttg aagacctgaa gaatgtcttc   420
ccccctgagg tggccgtctt tgaaccttca gaggctgaaa ttagccacac tcagaaagct   480
accctggtgt gtctggcaac tggcttctat ccagatcacg tggagctgag ctggtgggtc   540
aacggaaagg aagtgcattc cggagtctct acagacccac agccctgaa agagcagccc    600
gccctgaatg attcccggta ttgcctgtct agtcggctga gagtgtctgc tacctttttgg   660
cagaaccta ggaatcattt ccgctgtcag gtgcagtttt acggcctgtc tgagaatgac    720
gaatggaccc aggatcgagc taagcctgtg acacagatcg tcagtgcaga ggcttgggga   780
cgagcagact gcggcttcac aagtgaatca taccagcagg gggtgctgag cgccactatc   840
ctgtacgaga ttctgctggg aaaaggctacc ctgtatgcag tgctggtctc cgccctggtg   900
ctgatggcta tggtcaagcg aaaagacagc cggggcgggt ccgcaacaaa cttttccctg   960
ctgaaacagg ccggcgatgt ggaggaaaat cctgggccaa tggaaaagaa tccattggct  1020
gcaccctgc ttatactctg gtttcacttg gactgcgtat cctcaatttt gaatgttgaa   1080
caatcacccc agagtctcca cgtccaagaa ggggactcaa caaactttac ctgtagtttc  1140
ccctcaagta acttctacgc tctccactgg tatcggtggg agactgccaa gagccccgaa  1200
gctctcttcg taatgaccct taatggagac gaaaaaaaga aggggagaat aagtgccact  1260
ctgaatacca aagagggcta ttcctatctc tacataaaag gaagtcaacc tgaggattcc  1320
gccacttacc tgtgcgcgtt catcactgga aaccagttct atttcgggac cggaacatct  1380
ctgactgtaa tcccaaatat tcagaacccc gatcctgccg tctatcagct gagggacagc  1440
aagagctccg ataaatccgt gtgtctgttc acagactttg attctcagac taatgtgagc  1500
cagtccaagg acagtgatgt gtacatcacc gacaaaacag tcctggatat gcgcagcatg  1560
gacttcaagt ctaacagtgc agtggcctgg agtaacaagt cggacttcgc ttgcgcaaac  1620
gcctttaaca attcaatcat tcccgaggat accttctttc caagccccga atctagttgt  1680
gacgtgaagc tggtcgagaa aagtttcgaa acagatacta acctgaattt tcagaacctg  1740
tcagtgatcg gcttccggat tctgctgctg aaggtcgccg ggttcaatct gctgatgacc  1800
ctgagactgt ggtcaagcgc ggccgcctga                                    1830

SEQ ID NO: 35            moltype = AA   length = 474
FEATURE                  Location/Qualifiers
REGION                   1..474
                         note = Synthetic Polypeptide
source                   1..474
                         mol_type = protein
                         organism = synthetic construct
SEQUENCE: 35
MSRSVALAVL ALLSLSGLEA SLYNTVATLG GGASGGGGSG GGGSIQRTPK IQVYSRHPAE    60
NGKSNFLNCY VSGFHPSDIE VDLLKNGERI EKVEHSDLSF SKDWSFYLLY YTEFTPTEKD   120
EYACRVNHVT LSQPKIVKWD RDMGGGGSGG GGSGGGGSGG GGSHSMRYFF TSVSRPGRGE   180
PRFIAVGYVD DTQFVRFDSD AASQRMEPRA PWIEQEGPEY WDGETRKVKA HSQTHRVDLG   240
TLRGAYNQSE AGSHTVQRMY GCDVGSDWRF LRGYHQYAYD GKDYIALKED LRSWTAADMA   300
AQTTKHKWEA AHVAEQLRAY LEGTCVEWLR RYLENGKETL QRTDAPKTHM THHAVSDHEA   360
TLRCWALSFY PAEITLTWQR DGEDQTQDTE LVETRPAGDG TFQKWAAVVV PSGQEQRYTC   420
HVQHEGLPKP LTLRWEPSSQ PTIPIVGIIA GLVLFGAVIT GAVVAAVMWR RKSS         474

SEQ ID NO: 36            moltype = DNA   length = 1425
FEATURE                  Location/Qualifiers
misc_feature             1..1425
                         note = Synthetic Polynucleotide
source                   1..1425
                         mol_type = other DNA
                         organism = synthetic construct
SEQUENCE: 36
atgagccgca gcgtggcgct ggcggtgctg gcgctgctga gcctgagcgg cctggaagcg    60
agcctttaca acacggtcgc gacactgggt ggaggagcta gcggaggtgg tggtagtggt   120
```

-continued

```
ggtggtggtt ccatacaaag aactccaaag atccaagttt acagtagaca tcctgctgaa      180
aacggtaaat ctaatttctt gaactgttac gtctccggtt tccacccaag tgatatagaa      240
gttgacttgt tgaaaaatgg tgaaagaatc gaaaaggttg aacattcaga tttgtctttt      300
tctaaggact ggtccttcta tttgttgtac tacacagagt tcactccaac tgaaaaggat      360
gaatacgctt gcagagttaa tcatgtaacc ttgtctcaac ctaaaatcgt taagtgggat      420
agagacatgg gtggtggcgg cagtggtggc gggggcagcg gtggtggggg cagcggtggt      480
ggtggttccc atagtatgag atatttcttt acttctgttt caagaccagg tagaggtgaa      540
cctagattca tcgcagtcgg ttacgttgat gacacacaat ttgtaagatt cgattccgac      600
gctgcaagtc aaagaatgga accaagagca ccttggattg aacaagaagg tccagaatat      660
tgggatggtg aaactagaaa agttaaggcc cattctcaaa ctcacagagt agatttgggt      720
acattaagag gtgcttataa tcaatctgaa gcaggttcac atacagtaca aagaatgtac      780
ggttgtgatg tcggttcaga ctggagattt ttgagaggtt atcaccaata tgcttacgat      840
ggtaaagact acattgcatt gaaggaagat ttgagatcct ggaccgccgc tgacatggca      900
gcccaaacta caaaacataa gtgggaagct gcacacgtag cagaacaatt gagagcctat      960
ttggaaggta catgtgtcga atggttgaga agatacttag aaaacggtaa agaaacattg     1020
caaagaaccg atgctccaaa gactcatatg acacatcacg ccgttagtga tcacgaagct     1080
actttgagat gctgggcatt atcttttac cctgccgaaa tcacattgac ctggcaaaga     1140
gatggtgaag accaaaccca agatactgaa ttagttgaaa ccagaccagc aggtgacggt     1200
actttccaaa aatgggccgc tgttgtagtc ccttcaggtc aagaacaaag atacacatgc     1260
catgtccaac acgaaggttt accaaagcca ttgacattga gatgggaacc atcctctcag     1320
cctacaatac caatagtcgg cataatcgct ggactggtcc tgttcgggc ggtaatcacg     1380
ggagctgtag tcgctgcggt gatgtggcgc agaaaaagct cctga                     1425
```

SEQ ID NO: 37          moltype = AA  length = 474
FEATURE                Location/Qualifiers
REGION                  1..474
                        note = Synthetic Polypeptide
source                  1..474
                        mol_type = protein
                        organism = synthetic construct
SEQUENCE: 37

```
MSRSVALAVL ALLSLSGLEA NLVPMVATVG ASGGSGGGSG GGGSIQRTPK IQVYSRHPAE       60
NGKSNFLNCY VSGFHPSDIE VDLLKNGERI EKVEHSDLSF SKDWSFYLLY YTEFTPTEKD      120
EYACRVNHVT LSQPKIVKWD RDMGGGGSGG GGSGGGGSGG GGSHSMRYFF TSVSRPGRGE      180
PRFIAVGYVD DTQFVRFDSD AASQRMEPRA PWIEQEGPEY WDGETRKVKA HSQTHRVDLG      240
TLRGAYNQSE AGSHTVQRMY GCDVGSDWRF LRGYHQYAYD GKDYIALKED LRSWTAADMA      300
AQTTKHKWEA AHVAEQLRAY LEGTCVEWLR RYLENGKETL QRTDAPKTHM THHAVSDHEA      360
TLRCWALSFY PAEITLTWQR DGEDQTQDTE LVETRPAGDG TFQKWAAVVV PSGQEQRYTC      420
HVQHEGLPKP LTLRWEPSSQ PTIPIVGIIA GLVLFGAVIT GAVVAAVMWR RKSS            474
```

SEQ ID NO: 38          moltype = DNA  length = 1425
FEATURE                Location/Qualifiers
misc_feature           1..1425
                        note = Synthetic Polynucleotide
source                  1..1425
                        mol_type = other DNA
                        organism = synthetic construct
SEQUENCE: 38

```
atgagccgca gcgtggcgct ggcggtgctg gcgctgctga gcctgagcgg cctggaagcg       60
aacttggttc cgatggtggc aaccgtaggt gctagcggag ggtccggcgg gggtagcggt      120
ggtggaggaa gcatacaaag aactccaaag atccaagttt acagtagaca tcctgctgaa      180
aacggtaaat ctaatttctt gaactgttac gtctccggtt tccacccaag tgatatagaa      240
gttgacttgt tgaaaaatgg tgaaagaatc gaaaaggttg aacattcaga tttgtctttt      300
tctaaggact ggtccttcta tttgttgtac tacacagagt tcactccaac tgaaaaggat      360
gaatacgctt gcagagttaa tcatgtaacc ttgtctcaac ctaaaatcgt taagtgggat      420
agagacatgg gtggtggcgg cagtggtggc gggggcagcg gtggtggggg cagcggtggt      480
ggtggttccc atagtatgag atatttcttt acttctgttt caagaccagg tagaggtgaa      540
cctagattca tcgcagtcgg ttacgttgat gacacacaat ttgtaagatt cgattccgac      600
gctgcaagtc aaagaatgga accaagagca ccttggattg aacaagaagg tccagaatat      660
tgggatggtg aaactagaaa agttaaggcc cattctcaaa ctcacagagt agatttgggt      720
acattaagag gtgcttataa tcaatctgaa gcaggttcac atacagtaca aagaatgtac      780
ggttgtgatg tcggttcaga ctggagattt ttgagaggtt atcaccaata tgcttacgat      840
ggtaaagact acattgcatt gaaggaagat ttgagatcct ggaccgccgc tgacatggca      900
gcccaaacta caaaacataa gtgggaagct gcacacgtag cagaacaatt gagagcctat      960
ttggaaggta catgtgtcga atggttgaga agatacttag aaaacggtaa agaaacattg     1020
caaagaaccg atgctccaaa gactcatatg acacatcacg ccgttagtga tcacgaagct     1080
actttgagat gctgggcatt atcttttac cctgccgaaa tcacattgac ctggcaaaga     1140
gatggtgaag accaaaccca agatactgaa ttagttgaaa ccagaccagc aggtgacggt     1200
actttccaaa aatgggccgc tgttgtagtc ccttcaggtc aagaacaaag atacacatgc     1260
catgtccaac acgaaggttt accaaagcca ttgacattga gatgggaacc atcctctcag     1320
cctacaatac caatagtcgg cataatcgct ggactggtcc tgttcgggc ggtaatcacg     1380
ggagctgtag tcgctgcggt gatgtggcgc agaaaaagct cctga                     1425
```

SEQ ID NO: 39          moltype = AA  length = 482
FEATURE                Location/Qualifiers
REGION                  1..482
                        note = Synthetic Polypeptide
source                  1..482
                        mol_type = protein

```
                              organism = synthetic construct
SEQUENCE: 39
MATGSRTSLL LAFGLLCLPW LQEGSAGILG FVFTLGCSGG SGGGSGGGGS IQRTPKIQVY   60
SRHPAENGKS NFLNCYVSGF HPSDIEVDLL KNGERIEKVE HSDLSFSKDW SFYLLYYTEF  120
TPTEKDEYAC RVNHVTLSQP KIVKWDRDMG GGGSGGGSGG SGSGGGGSGG SHSMRYFFTS  180
VSRPGRGEPR FIAVGYVDDT QFVRFDSDAA SQRMEPRAPW IEQEGPEYWD GETRKVKAHS  240
QTHRVDLGTL RGCYNQSEAG SHTVQRMYGC DVGSDWRFLR GYHQYAYDGK DYIALKEDLR  300
SWTAADMAAQ TTKHKWEAAH VAEQLRAYLE GTCVEWLRRY LENGKETLQR TDAPKTHMTH  360
HAVSDHEATL RCWALSFYPA EITLTWQRDG EDQTQDTELV ETRPAGDGTF QKWAAVVVPS  420
GQEQRYTCHV QHEGLPKPLT LRWEPSSQPT IPIVGIIAGL VLFGAVITGA VVAAVMWRRK  480
SS                                                                 482

SEQ ID NO: 40         moltype = DNA   length = 1449
FEATURE               Location/Qualifiers
misc_feature          1..1449
                      note = Synthetic Polynucleotide
source                1..1449
                      mol_type = other DNA
                      organism = synthetic construct SEQUENCE: 40
atggcgacgg gttcaagaac ttccctactt cttgcatttg gcctgctttg tttgccgtgg   60
ttacaggagg gatccgcagg tatcctcgga tttgtgttta cacttggatg cagcggaggg  120
tccggcgggg gtagcggtgg tggaggaagc atacaaagaa ctccaaagat ccaagtttac  180
agtagacatc ctgctgaaaa cggtaaatct aatttcttga actgttacgt ctccggtttc  240
cacccaagtg atatagaagt tgacttgttg aaaaatggtg aaagaatcga aaaggttgaa  300
cattcagatt tgtctttttc taaggactgg tccttctatt tgttgtacta cacagagttc  360
actccaactg aaaaggatga atacgcttgc agagttaatc atgtaacctt gtctcaacct  420
aaaatcgtta agtgggatag agacatggga ggcggcggct ctggtggcag cggctctgga  480
ggttctggaa gtggaggcgg ctctggaggc tcccatagta tgagatattt ctttacttct  540
gtttcaagac caggtagagg tgaacctaga ttcatcgcag tcggttacgt tgatgacaca  600
caatttgtaa gattcgattc cgacgctgca agtcaaagaa tggaaccaag agcaccttgg  660
attgaacaag aaggtccaga atattgggat ggtgaaacta gaaaagttaa ggcccattct  720
caaactcaca gagtagattt gggtacatta agaggttgtt ataatcaatc tgaagcaggt  780
tcacatacag tacaaagaat gtacggttgt gatgtcggtt cagactggag attttttgaga  840
ggttatcacc aatatgctta cgatggtaaa gactacattg cattgaagga agatttgaga  900
tcctggaccg ccgctgacat ggcagcccaa actacaaaac ataagtggga agctgcacac  960
gtagcagaac aattgagagc ctatttggaa ggtacatgtg tcgaatggtt gagaagatac 1020
ttagaaaacg gtaaagaaac attgcaaaga accgatgctc aaaagactca tatgacacat 1080
cacgccgtta gtgatcacga agctactttg agatgctggg cattatcttt ttaccctgcc 1140
gaaatcacat tgacctggca aagagatggt gaagaccaaa cccaagatac tgaattagtt 1200
gaaaccagac cagcaggtga cggtactttc caaaaatggg ccgctgttgt agtcccttca 1260
ggtcaagaac aaagatacac atgccatgtc caacacgaag gtttaccaaa gccattgaca 1320
ttgagatggg aaccatcctc tcagcctaca ataccaatag tcggcataat cgctggactg 1380
gtcctgttcg gggcggtaat cacgggagct gtagtcgctg cggtgatgtg gcgcagaaaa 1440
agctcctga                                                          1449

SEQ ID NO: 41         moltype = AA   length = 474
FEATURE               Location/Qualifiers
REGION                1..474
                      note = Synthetic Polypeptide
source                1..474
                      mol_type = protein
                      organism = synthetic construct
SEQUENCE: 41
MSRSVALAVL ALLSLSGLEA GILGFVFTLG GGASGGGGSG GGGSIQRTPK IQVYSRHPAE   60
NGKSNFLNCY VSGFHPSDIE VDLLKNGERI EKVEHSDLSF SKDWSFYLLY YTEFTPTEKD  120
EYACRVNHVT LSQPKIVKWD RDMGGGGSGG GGSGGGGSGG GGSHSMRYFF TSVSRPGRGE  180
PRFIAVGYVD DTQFVRFDSD AASQRMEPRA PWIEQEGPEY WDGETRKVKA HSQTHRVDLG  240
TLRGAYNQSE AGSHTVQRMY GCDVGSDWRF LRGYHQYAYD GKDYIALKED LRSWTAADMA  300
AQTTKHKWEA AHVAEQLRAY LEGTCVEWLR RYLENGKETL QRTDAPKTHM THHAVSDHEA  360
TLRCWALSFY PAEITLTWQR DGEDQTQDTE LVETRPAGDG TFQKWAAVVV PSGQEQRYTC  420
HVQHEGLPKP LTLRWEPSSQ PTIPIVGIIA GLVLFGAVIT GAVVAAVMWR RKSS         474

SEQ ID NO: 42         moltype = DNA   length = 1425
FEATURE               Location/Qualifiers
misc_feature          1..1425
                      note = Synthetic Polynucleotide
source                1..1425
                      mol_type = other DNA
                      organism = synthetic construct SEQUENCE: 42
atgagccgca gcgtggcgct ggcggtgctg gcgctgctga gcctgagcgg cctggaagcg   60
ggtatcctcg gatttgtgtt tacacttggt ggaggagcta gcggaggtgg tggtagtggt  120
ggtggttggt ccatacaaag aactccaaag atccaagttt acagtagaca tcctgctgaa  180
aacggtaaat ctaatttctt gaactgttac gtctccggtt tccacccaag tgatatagaa  240
gttgacttgt tgaaaaatgg tgaaagaatc gaaaaggttg aacattcaga tttgtctttt  300
tctaaggact ggtccttcta tttgttgtac tacacagagt tcactccaac tgaaaaggat  360
gaatacgctt gcagagttaa tcatgtaacc ttgtctcaac ctaaaatcgt taagtgggat  420
agagacatgg gtggtggcgg cagtggtggc ggggggcagcg gtggtggggg cagcggtggt  480
```

-continued

```
ggtggttccc atagtatgag atatttcttt acttctgttt caagaccagg tagaggtgaa      540
cctagattca tcgcagtcgg ttacgttgat gacacacaat ttgtaagatt cgattccgac      600
gctgcaagtc aaagaatgga accaagagca ccttggattg aacaagaagg tccagaatat      660
tgggatggtg aaactagaaa agttaaggcc cattctcaaa ctcacagagt agatttgggt      720
acattaagag gtgcttataa tcaatctgaa gcaggttcac atacagtaca aagaatgtac      780
ggttgtgatg tcggttcaga ctggagattt ttgagaggtt atcaccaata tgcttacgat      840
ggtaaagact acattgcatt gaaggaagat ttgagatcct ggaccgccgc tgacatggca      900
gcccaaacta caaaacataa gtgggaagct gcacacgtag cagaacaatt gagagcctat      960
ttggaagaca catgtgtcga atggttgaga agatacttag aaaacggtaa agaaacattg     1020
caaagaaccg atgctccaaa gactcatatg acacatcacg ccgttagtga tcacgaagct     1080
actttgagat gctgggcatt atctttttac cctgccgaaa tcacattgac ctggcaaaga     1140
gatggtgaag accaaaccca agatactgaa ttagttgaaa ccagaccagc aggtgacggt     1200
actttccaaa aatgggccgc tgttgtagtc ccttcaggtc aagaacaaag atacacatgc     1260
catgtccaac acgaaggttt accaaagcca ttgacattga gatgggaacc atcctctcag     1320
cctacaatac caatagtcgg cataatcgct ggactggtcc tgttcgggc ggtaatcacg      1380
ggagctgtag tcgctgcggt gatgtggcgc agaaaaagct cctga                     1425
```

SEQ ID NO: 43              moltype = AA   length = 273
FEATURE                    Location/Qualifiers
REGION                     1..273
                           note = Synthetic Polypeptide
source                     1..273
                           mol_type = protein
                           organism = synthetic construct
SEQUENCE: 43

```
MGHTRRQGTS PSKCPYLNFF QLLVLAGLSH FCSGVIHVTK EVKEVATLSC GHNVSVEELA      60
QTRIYWQKEK KMVLTMMSGD MNIWPEYKNR TIFDITNNLS IVILALRPSD EGTYECVVLK     120
YEKDAFKREH LAEVTLSVKA DFPTPSISDF EIPTSNIRRI ICSTSGGFPE PHLSWLENGE     180
ELNAINTTVS QDPETELYAV SSKLDFNMTT NHSFMCLIKY GHLRVNQTFN WNTTKQEHFP     240
DNLLPSWAIT LISVNGIFVI CCLTYCFAPR CRE                                  273
```

SEQ ID NO: 44              moltype = DNA   length = 822
FEATURE                    Location/Qualifiers
misc_feature               1..822
                           note = Synthetic Polynucleotide
source                     1..822
                           mol_type = other DNA
                           organism = synthetic construct
SEQUENCE: 44

```
atgggtcata cacgccgcca aggaacctca ccatctaagt gcccatatct gaatttcttt      60
caacttctcg tgctggcggg gctcagtcat ttctgcagtg gggtcattca cgttactaaa     120
gaggtcaagg aggtcgcaac attgagttgt ggccataacg tatcagttga agaactcgcg     180
cagacacgga tttactggca aaaggaaaag aagatggtgt tgacaatgat gagcggtgac     240
atgaacattt ggccagagta caaaaatcga acgatattcg atataaccaa taacttgtcc     300
atagtaatac ttgccttgcg accttctgac gagggaacgt atgaatgtgt agtgcttaag     360
tatgaaaaag atgcctttaa gcgggaacac ttggctgagg ttacactctc cgttaaggcg     420
gacttcccta cgccgtctat atccgacttc gagataccca cttctaacat tcgacgcatc     480
atttgctcaa cctcaggtgg tttcccagag cctcacttga gctggctgga gaatggcgaa     540
gaacttaacg caatcaatac cacggtgtcc caagacccgg agacagagct gtacgccgtg     600
tcatccaaac tggattttaa catgacgaca aatcatagtt tcatgtgtct gatcaaatat     660
gggcatctca gggtgaatca gactttttaat tggaacacta ccaaacaaga gcacttccca     720
gataatctgt tgccaagctg ggcgataact cttatctccg tcaacggtat cttcgtaatt     780
tgctgcctca cctattgttt cgcgcctcga tgccgagaat ga                        822
```

SEQ ID NO: 45              moltype = AA   length = 275
FEATURE                    Location/Qualifiers
REGION                     1..275
                           note = Synthetic Polypeptide
source                     1..275
                           mol_type = protein
                           organism = synthetic construct
SEQUENCE: 45

```
MDPQCTMGLS NILFVMAFLL SGAAPLKIQA YFNETADLPC QFANSQNQSL SELVVFWQDQ      60
ENLVLNEVYL GKEKFDSVHS KYMGRTSFDS DSWTLRLHNL QIKDKGLYQC IIHHKKPTGM     120
IRIHQMNSEL SVLANFSQPE IVPISNITEN VYINLTCSSI HGYPEPKKMS VLLRTKNSTI     180
EYDGVMQKSQ DNVTELYDVS ISLSVSFPDV TSNMTIFCIL ETDKTRLLSS PFSIELEDPQ     240
PPPDHIPWIT AVLPTVIICV MVFCLILWKW KKKKR                                275
```

SEQ ID NO: 46              moltype = DNA   length = 828
FEATURE                    Location/Qualifiers
misc_feature               1..828
                           note = Synthetic Polynucleotide
source                     1..828
                           mol_type = other DNA
                           organism = synthetic construct
SEQUENCE: 46

```
atggatccgc aatgcacaat ggggcttagc aacattctct ttgtaatggc ttttctcctg      60
tccggtgcag cgcccctcaa gattcaggca tatttttaacg aaaccgcgga cctccccttgt     120
cagttcgcaa atagtcagaa tcaaagtctc agtgagttgg tcgtattttg gcaggatcaa      180
```

```
gagaatctcg tcctgaacga ggtttacctg ggcaaagaga agtttgattc cgtgcatagt   240
aagtacatgg gtcgcacgtc ctttgactcc gacagctgga cacttaggct gcacaacctc   300
cagatcaaag ataagggtct ttaccagtgc attatacacc ataaaaaacc tactgggatg   360
atcaggattc accagatgaa cagcgagttg tcagtgttgg caaatttctc acaaccagaa   420
atagtaccta tctcaaacat caccgaaaac gtatatatta acctcacctg ttctagtatc   480
catggttatc cagagccaaa gaaaatgtcc gtgttgctga aacaaagaa ctctacaata   540
gagtacgacg gagtgatgca aaaatcccag gacaacgtaa cagaactgta cgatgttagc   600
atctctcttt ctgtgagctt tcctgatgtg acatccaaca tgaccatttt ttgcatactc   660
gaaacagaca aaacgcgact tttgtcctcc ccctttttcaa tcgagttgga ggatccccaa   720
cctcccccg accatatccc gtggatcacc gctgttcttc ctaccgtaat catctgtgtc   780
atggtattct gccttattct ctggaaatgg aagaaaaaga agcgatga                828
```

```
SEQ ID NO: 47              moltype = AA  length = 551
FEATURE                    Location/Qualifiers
REGION                     1..551
                           note = Synthetic Polypeptide
source                     1..551
                           mol_type = protein
                           organism = synthetic construct
SEQUENCE: 47
METDTLLLWV LLLWVPGSTG ADYKDDDDKD IQMTQSPSSL PASLGDRVTI NCQASQDISN   60
YLNWYQQKPG KAPKLLIYYT NKLADGVPSR FSGSGSGRDS SFTISSLESE DIGSYYCQQY  120
YNYPWTFGPG TKLEIKRADA KPTVSIFPPS SEQLGTGSAT LVCFVNNFYP KDINVKWKVD  180
GSEKRDGVLQ SVTDQDSKDS TYSLSSTLSL TKADYERHNL YTCEVTHKTS TAAIVKTLNR  240
NECGSGATNF SLLKQAGDVE ENPGPMVPCT LLLLLAAALA PTQTRAEVQL VESGGGLVQP  300
GKSLKLSCEA SGFTFSGYGM HWVRQAPGRG LESVAYITSS SINIKYADAV KGRFTVSRDN  360
AKNLLFLQMN ILKSEDTAMY YCARFDWDKN YWGQGTMVTV SSAKTTAPSV YPLAPACDST  420
TSTTNTVTLG CLVKGYFPEP VTVIWNSGAL TSGVHTFPSV LHSGLYSLSS SVTVPSSTWP  480
SQTVTCNVAH PASSTTVDLK IEAVGQDTQE VIVVPHSLPF KVVVISAILA LVVLTIISLI  540
ILIMLWQKKP R                                                       551
```

```
SEQ ID NO: 48              moltype = DNA  length = 1656
FEATURE                    Location/Qualifiers
misc_feature               1..1656
                           note = Synthetic Polynucleotide
source                     1..1656
                           mol_type = other DNA
                           organism = synthetic construct
SEQUENCE: 48
atggaaaccg acaccttgct cctgtgggtt ctcctgttgt gggtgccggg atcaacggga   60
gctgattaca aggatgacga cgataaggac attcaaatga cccagtctcc ttccagcctg  120
ccagcgagcc tggggacag agtgaccatt aactgtcagg cttcacagga tattagcaat  180
tacctcaact ggtatcaaca gaagccaggc aaggccccca aactgctcat ttattacacg  240
aacaaactgg cggacggtgt tccttccaga tttagcggct ccggttccgg gcgggacagt  300
agctttacta taagcagttt ggaatccgag gacataggtt cctattactg ccagcagtat  360
tacaattacc cttggacatt tggtccgggt actaagctcg agataaagcg ggccgatgcc  420
aagcccaccg tatcaatctt cccgccatcc agtgagcagc tcggtacagg aagcgcgact  480
ctggtttgtt tcgttaacaa tttttatcct aaggacataa acgttaagtg gaaggtagac  540
ggaagcgaga aacgagatgg tgtattgcag agtgtcacag accaggattc caaagactcc  600
acatactccc tctcctcaac tcttagtctt acgaaggctg attacgaaag gcacaacctg  660
tatacgtgtg aggtcactca taaaaccagt actgcggcga ttgtaaaaac gctgaacagg  720
aacgaatgtg gaagtggtgc tacgaacttc tcactgctta agcaagctgg agatgttgag  780
gaaaaccctg gaccaatggt gccgtgcacc ctccttttgc ttttggccgc tgcgttggct  840
ccaacccaga ctagggcaga agtacagctt gtggaaagcg gcggagggct tgtgcagcct  900
ggcaaatccc tcaaactcag ttgtgaggct agtggcttca catttagcgg gtacggtatg  960
cactgggtcc gacaggcacc tgggcgcgga ttggaaagcg tcgcatacat tacaagctca 1020
agcataaata taaaatatgc ggatgctgtc aagggagat tcaccgtttc tagggataac 1080
gcgaagaacc ttttgttcct gcaaatgaac attctcaaga gcgaggacac ggctatgtac 1140
tattgtgcta ggttcgactg ggacaagaat tattgggac aaggtactat ggttacagta 1200
agtagtgcta aaactactgc tccgtcagta tatcccctcg caccagcctg cgattctact 1260
accagcacta ctaatacagt aacactcggg tgcctcgtga aggggtattt ccctgaacca 1320
gttacggtca tctggaatag tggggccttg actagtggtg tacatacgtt cccatccgtc 1380
cttcactcag gactctacag cctcagctca agtgttaccg taccctcttc aacatggccg 1440
tctcagacag ttacgtgcaa cgtcgctcat cctgcaagtt ccacgactgt ggaccttaaa 1500
attgaagccg tcggccagga cacccaggag gtaattgttg tcccacattc acttccattc 1560
aaggtggtcg tgatctctgc gatcctcgcg ctcgtcgttt tgacgatcat tagcctcatc 1620
atcctcatca tgttgtggca gaaaaagccc cggtaa                           1656
```

```
SEQ ID NO: 49              moltype = AA  length = 555
FEATURE                    Location/Qualifiers
REGION                     1..555
                           note = Synthetic Polypeptide
source                     1..555
                           mol_type = protein
                           organism = synthetic construct
SEQUENCE: 49
METDTLLLWV LLLWVPGSTG ADYKDDDDKY ELIQPSSASV TVGETVKITC SGDQLPKNFA   60
YWFQQKSDKN ILLLIYMDNK RPSGIPERFS GSTSGTTATL TISGAQPEDE AAYYCLSSYG  120
DNNDLVFGSG TQLTVLRGPK SSPKVTVFPP SPEELRTNKA TLVCLVNDFY PGSATVTWKA  180
```

```
NGATINDGVK TTKPSKQGQN YMTSSYLSLT ADQWKSHNRV SCQVTHEGET VEKSLSPAEC   240
LGSGATNFSL LKQAGDVEEN PGPMVPCTLL LLLAAALAPT QTRAEVYLVE SGGDLVQPGS   300
SLKVSCAASG FTFSDFWMYW VRQAPGKGLE WVGRIKNIPN NYATEYADSV RGRFTISRDD   360
SRNSIYLQMN RLRVDDTAIY YCTRAGRFDH FDYWGQGTMV TVSSATTTAP SVYPLAPACD   420
STTSTTDTVT LGCLVKGYFP EPVTVSWNSG ALTSGVHTFP SVLHSGLYSL SSSVTVPSST   480
WPKQPITCNV AHPASSTKVD KKIEPRAVGQ DTQEVIVVPH SLPFKVVVIS AILALVVLTI   540
ISLIILIMLW QKKPR                                                     555

SEQ ID NO: 50           moltype = DNA   length = 1668
FEATURE                 Location/Qualifiers
misc_feature            1..1668
                        note = Synthetic Polynucleotide
source                  1..1668
                        mol_type = other DNA
                        organism = synthetic construct
SEQUENCE: 50
atggaaaccg acaccttgct cctgtgggtt ctcctgttgt gggtgccggg atcaacggga   60
gctgattaca aggatgacga cgataagtat gaattgatcc aaccctccag tgcgagtgtc   120
actgtcggtg agaccgttaa aataacttgt agcggcgacc aacttccgaa gaactttgct   180
tactggtttc aacaaaagtc agacaagaat atattgcttt tgatatatat ggacaataag   240
agacccagtg ggattccaga gagattttcc ggctcaacct ctggaacaac agccacactt   300
acgatatcag gggcccagcc tgaagacgag gcagcgtact ctgcctttc  ctcctacgga   360
gataataacg atcttgtgtt cggctccgga acacagctta ccgttctgcg gggaccaaag   420
agcagtccca aagtaaccgt ctttcccca  agccccgagg agcttaggac taataaagcg   480
acgctggtct gtcttgtcaa tgacttttac cctggctcag ccacagtgac atggaaggca   540
aatggggcca ctattaacga cggtgtcaag actacgaagc caagcaaaca ggggcaaaac   600
tacatgacaa gcagctactt gagtttgact gcggaccagt ggaagtctca caatagagtt   660
agctgtcaag tcacacatga aggcgagact gttgaaaaat cactctcccc tgcggaatgc   720
ttgggaagtg gtgctacgaa cttctcactg cttaagcaag ctggagatgt tgaggaaaac   780
cctggaccaa tggtgccgtg caccctcctt ttgcttttgg ccgctgcgtt ggctccaacc   840
cagactaggg cagaggttta tcttgttgag tccggaggtg acttggtgca gcctggctct   900
tcccttaagg tctcatgcgc cgcatccggc tttacattct ctgatttttg gatgtattgg   960
gttcgccagg ctcctggtaa agggctggaa tgggtgggca gaatcaagaa catccccaat  1020
aactacgcta cagaatatgc cgactcagtg agggggcgct tcactatatc acgagacgat  1080
tcacggaact ctatttatct gcagatgaac cggttgaggg ttgatgacac gcgatatat   1140
tattgcacca gagctggcag gtttgaccac tttgactact ggggacaggg tacgatggtg  1200
actgtgagta gcgcaacgac aaccgcacct tcagtgtacc cactcgctcc tgcttgcgac  1260
tccaccacta gcacgacaga caccgtcact ctcggatgtt tggtaaaagg atattttcca  1320
gaacctgtca ccgtttcttg gaatagtggc gcattgacct caggtgtcca tacgttccct  1380
tccgtcttgc acagtggact gtactcattg tcatctagtg ttacagtacc gtcctccaca  1440
tggccgaagc agccgataac ttgtaatgtc gcccatccag cctcctccac taaggtggac  1500
aagaaaatag agcctagagc cgtcggccag gacacccagg aggtaattgt tgtcccacat  1560
tcacttccat tcaaggtggt cgtgatctct gcgatcctcg cgctcgtcgt tttgacgatc  1620
attagcctca tcatcctcat catggttgtgg cagaaaaagc cccggtaa            1668

SEQ ID NO: 51           moltype = AA   length = 512
FEATURE                 Location/Qualifiers
REGION                  1..512
                        note = Synthetic Polypeptide
source                  1..512
                        mol_type = protein
                        organism = synthetic construct
SEQUENCE: 51
MNFLLLTFIV LPLCSHAKFS IVFPQSQKGN WKNVPSSYHY CPSSSDQNWH NDLLGITMKV   60
KMPKTHKAIQ ADGWMCHAAK WITTCDFRWY GPKYITHSIH SIQPTSEQCK ESIKQTKQGT   120
WMSPGFPPQN CGYATVTDSV AVVVQATPHH VLVDEYTGEW IDSQFPNGKC ETEECETVHN   180
STVWYSDYKV TGLCDATLVD TEITFFSEDG KKESIGKPNT GYRSNYFAYE KGDKVCKMNY   240
CKHAGVRLPS GVWFEFVDQD VYAAAKLPEC PVGATISAPT QTSVDVSLIL DVERILDYSL   300
CQETWSKIRS KQPVSPVDLS YLAPKNPGTG PAFTIINGTL KYFETRYIRI DIDNPIISKM   360
VGKISGSQTE RELWTEWFPY EGVEIGPNGI LKTPTGYKFP LFMIGHGMLD SDLHKTSQAE   420
VFEHPHLAEA PKQLPEEETL FFGDTGISKN PVELIEGWFS SWKSTVVTFF FAIGVFILLY   480
VVARIVIAVR YRYQGSNNKR IYNDIEMSRF RK                                  512

SEQ ID NO: 52           moltype = DNA   length = 1539
FEATURE                 Location/Qualifiers
misc_feature            1..1539
                        note = Synthetic Polynucleotide
source                  1..1539
                        mol_type = other DNA
                        organism = synthetic construct
SEQUENCE: 52
atgaacttc  tgctgctcac gtttatcgta ctcccgttgt gctctcatgc gaaattttca   60
atagtctttc ctcagtccca gaaagggaat tggaaaaatg ttccctccag ttaccactat  120
tgtccctcct cctctgacca aaactggcac aatgacttgc tcgggattac aatgaaagta  180
aagatgccga aaacccataa agccatacag gcggatgggt ggatgtgtca cgctgcgaag  240
tggatcacta catgcgattt ccggtggtat ggccctaagt acattacaca ctctatccat  300
agcatacagc cgacatcaga gcaatgcaaa gagagtatta aacagaccaa acaagggaca  360
tggatgagcc ctggctttcc acctcagaat tgtgggtacg cgaccgtcac ggatagtgtc  420
gctgttgtgt gcaggccac  gccacatcac gtactcgtag atgaatatac tggtgaatgg  480
```

-continued

```
atcgactccc aattcccgaa tgggaaatgt gagacggaag agtgcgaaac agtgcataac    540
tcaaccgttt ggtattccga ttacaaggtt actggtcttt gcgacgccac cctcgtggat    600
accgagatca cgtttttag tgaggatggc aagaaagagt caataggcaa acctaatact    660
ggctaccgga gtaactattt cgcttacgag aagggtgaca aggtatgtaa aatgaactat    720
tgcaagcatg cgggagtgcg actccccagt ggggtatggt tcgaatttgt tgaccaagac    780
gtatacgccg ctgcgaagtt gccagaatgc cccgtaggcg cgaccatttc agcacctacc    840
caaacgtccg ttgacgtctc cttgatactg gatgtagagc gaatcctgga ctacagtctc    900
tgccaggaaa cgtggtcaaa aataagaagt aagcagccag tttcacccgt ggatctgtct    960
tatctggcgc caaaaaaccc gggcacgggc cctgctttta ccataattaa cggaacgctt    1020
aaatacttcg aaacccgcta cattagaatc gatatagaca atcctattat cagcaagatg    1080
gtagggaaga tatctgggtc tcaaacggag cgagaattgg gacggagtg gttcccttat    1140
gagggagtgg aaattgggcc caacgggatc ctcaagaccc caacgggtta caagttccct    1200
ctgtttatga tcggccatgg catgttggac agtgacttgc acaaaacatc tcaggcagag    1260
gttttcgaac atccacattt ggcggaggcg cccaagcaac ttccagaaga agaaactctc    1320
ttctttggag atacaggcat ttcaaaaaat cctgtagaac tgatagaagg gtggttctct    1380
tcctggaaat caacggttgt cacgtttttc tttgcaatag gcgtatttat actcctgtac    1440
gtcgtagccc gcattgtgat cgcagtacga tacagatacc agggcagtaa caataaacgc    1500
atatataatg acatcgaaat gtcaaggttc cgaaagtga                          1539
```

SEQ ID NO: 53             moltype = AA   length = 512
FEATURE                   Location/Qualifiers
REGION                    1..512
                          note = Synthetic Polypeptide
source                    1..512
                          mol_type = protein
                          organism = synthetic construct
SEQUENCE: 53
```
MNFLLLTFIV LPLCSHAKFS IVFPQSQKGN WKNVPSSYHY CPSSSDQNWH NDLLGITMKV    60
KMPQTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
STVWYSDYKV TGLCDATLVD TEITFFSEDG KKESIGKPNT GYRSNYFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE AELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                  512
```

SEQ ID NO: 54             moltype = DNA   length = 1539
FEATURE                   Location/Qualifiers
misc_feature              1..1539
                          note = Synthetic Polynucleotide
source                    1..1539
                          mol_type = other DNA
                          organism = synthetic construct
SEQUENCE: 54
```
atgaactttc tgctgctcac gtttatcgta ctcccgttgt gctctcatgc gaaattttca    60
atagtctttc ctcagtccca gaaagggaat tggaaaaatg ttccctccag ttaccactat    120
tgtccctcct cctctgacca aaactggcac aatgacttgc tcgggattac aatgaaagta    180
aagatgccgc agacccataa agccatacag gcggatgggt ggatgtgtca cgctgcgaag    240
tggatcacta catgcgattt ccggtggtat ggccctaagt acattacaca ctctatccat    300
agcatacagc cgacatcaga gcaatgcaaa gagagtatta aacagaccaa acaagggaca    360
tggatgagcc ctggctttcc acctcagaat tgtgggtacg cgaccgtcac ggatagtgtc    420
gctgttgtgg tgcaggccac gccacatcac gtactcgtag atgaatatac tggtgaatgg    480
atcgactccc aattcccgaa tgggaaatgt gagacggaag agtgcgaaac agtgcataac    540
tcaaccgttt ggtattccga ttacaaggtt actggtcttt gcgacgccac cctcgtggat    600
accgagatca cgtttttag tgaggatggc aagaaagagt caataggcaa acctaatact    660
ggctaccgga gtaactattt cgcttacgag aagggtgaca aggtatgtaa aatgaactat    720
tgcaagcatg cgggagtgcg actccccagt ggggtatggt tcgaatttgt tgaccaagac    780
gtatacgccg ctgcgaagtt gccagaatgc cccgtaggcg cgaccatttc agcacctacc    840
caaacgtccg ttgacgtctc cttgatactg gatgtagagc gaatcctgga ctacagtctc    900
tgccaggaaa cgtggtcaaa aataagaagt aagcagccag tttcacccgt ggatctgtct    960
tatctggcgc caaaaaaccc gggcacgggc cctgctttta ccataattaa cggaacgctt    1020
aaatacttcg aaacccgcta cattagaatc gatatagaca atcctattat cagcaagatg    1080
gtagggaaga tatctgggtc tcaaacggag gccgaattgt ggacggagtg gttcccttat    1140
gagggagtgg aaattgggcc caacgggatc ctcaagaccc caacgggtta caagttccct    1200
ctgtttatga tcggccatgg catgttggac agtgacttgc acaaaacatc tcaggcagag    1260
gttttcgaac atccacattt ggcggaggcg cccaagcaac ttccagaaga agaaactctc    1320
ttctttggag atacaggcat ttcaaaaaat cctgtagaac tgatagaagg gtggttctct    1380
tcctggaaat caacggttgt cacgtttttc tttgcaatag gcgtatttat actcctgtac    1440
gtcgtagccc gcattgtgat cgcagtacga tacagatacc agggcagtaa caataaacgc    1500
atatataatg acatcgaaat gtcaaggttc cgaaagtga                          1539
```

LIGAND DISCOVERY AND GENE DELIVERY VIA RETROVIRAL SURFACE DISPLAY

RELATED APPLICATIONS

This application is a continuation of U.S. application Ser. No. 19/014,949, filed Jan. 9, 2025, entitled "LIGAND DISCOVERY AND GENE DELIVERY VIA RETROVI-RAL SURFACE DISPLAY," which is a continuation of U.S. application Ser. No. 18/458,657, filed Aug. 30, 2023, entitled "LIGAND DISCOVERY AND GENE DELIVERY VIA RETROVIRAL SURFACE DISPLAY," which is a continuation of U.S. application Ser. No. 16/826,665, filed Mar. 23, 2020, entitled "LIGAND DISCOVERY AND GENE DELIVERY VIA RETROVIAL SURFACE DIS-PLAY," which claims the benefit under 35 U.S.C. § 119(e) of the filing date of U.S. Provisional Application Ser. No. 62/851,889, entitled "LIGAND DISCOVERY AND GENE DELIVERY VIA RETROVIRAL SURFACE DISPLAY" and filed on May 23, 2019, the entire contents of each of which are incorporated herein by reference.

GOVERNMENT SUPPORT

This invention was made with government support under CA014051 awarded by the National Institutes of Health, and W81XWH-18-1-0208 awarded by the Defense Health Agency, Medical Research and Development Branch. The government has certain rights in the invention.

REFERENCE TO AN ELECTRONIC SEQUENCE LISTING

The contents of the electronic sequence listing (M065670463US06-SEQ-HCL.xml; Size: 107,755 bytes; and Date of Creation: Oct. 3, 2025) are herein incorporated by reference in their entirety.

BACKGROUND

It has been well established that retroviruses (e.g., lenti-viruses) can have their natural tropism redirected to targets of interest via pseudotyping a virus to express the envelope protein of a different virus. This is most commonly accom-plished via pseudotyping with the VSV glycoprotein, which targets the LDL receptor and therefore enables viral entry into a wide range of cells. Recently, groups have shown that if lentiviruses are pseudotyped with envelope proteins from paramyxoviruses such as measles virus or nipah virus, and if mutations are created that abolish native tropism, C-ter-minal fusions to these viruses allow receptor-mediated entry to the target cell of choice.

SUMMARY

Herein, the inventors have surprisingly demonstrated that a combination of mutations to abolish native function (e.g., tropism) and overexpression of a second membrane protein allows for that second protein to function as the basis for viral entry. These discoveries, as described herein, enable new and innovative methodologies, for example, to screen of cells that are notoriously challenging to screen for specific antigens and function (e.g., T cells), and to deliver nucleic acids to target cells in a target-specific manner.

Some aspects of the disclosure provide compositions of a retrovirus (e.g., a lentivirus) comprising (i) a nucleic acid comprising a non-viral membrane-bound protein comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter; and (ii) a mutated viral envelope protein compris-ing at least one mutation that diminishes its native function.

Some aspects of the disclosure provide compositions of a retrovirus (e.g., a lentivirus), comprising (i) a CD80 protein domain; and (ii) a mutated viral envelope protein comprising at least one mutation that diminishes its native function. The CD80 protein domain may be an extracellular domain. In some embodiments, the CD80 extracellular domain binds to a receptor on a target cell.

Some aspects of the disclosure provide methods of screening a population of cells, the method comprising (i) providing a retrovirus (e.g., a lentivirus) comprising a viral envelope protein comprising at least one mutation that diminishes its native function, a non-viral membrane-bound protein comprising a membrane-bound domain and an extra-cellular targeting domain, and a nucleic acid encoding a reporter; (ii) combining the retrovirus with a population of cells; and (iii) sorting the population of cells based on the presence or absence of the reporter. In some embodiments, the retrovirus (e.g., a lentivirus) comprises a nucleic acid comprising a non-viral membrane-bound protein comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter.

In some embodiments, the cells are somatic cells (e.g., antigen-specific cells, e.g., T cells or B cells). In some embodiments, the cells are isolated from a subject (e.g., a human subject). In some embodiments, the cells are isolated from the blood or a tumor of a subject. In some embodi-ments, the cells are maintained in liquid culture prior to being combined with the retrovirus.

In some embodiments, the viral envelope protein is a VSV-G envelope protein, a measles virus envelope protein, a nipah virus envelope protein, or a cocal virus G protein. A VSV-G envelope protein may be a mutated at one or more of any one of H8, K47, Y209, and/or R354. A measles virus envelope protein may be a mutated at one or more of any one of Y481, R533, S548, and/or F549. A nipah virus envelope protein may be a mutated at one or more of any one of E501, W504, Q530, and/or E533. A cocal virus G protein may be a mutated at K64 and/or R371.

In some embodiments, the non-viral membrane-bound protein comprises a Major Histocompatibility Complex (MHC) protein. In some embodiments, the extracellular targeting domain is a protein (e.g., interleukin-13), a peptide, or an antibody (e.g., anti-CD19 antibody, an anti-TCR antibody, or an anti-CD3 antibody). In some embodiments, the reporter is a fluorescent protein (e.g., green fluorescent protein, yellow fluorescent protein, red fluorescent protein) or an antibiotic resistance marker. In some embodiments, a linker is positioned between the membrane-bound domain and the extracellular targeting domain. A linker may be a rigid linker (e.g., a PDGFR stalk or a CD8α stalk), a flexible linker (e.g., comprising an amino acid sequence comprising GAPGAS (SEQ ID NO: 5) or GGGGS (SEQ ID NO: 7)), or an oligomerized linker (e.g., an IgG4 hinge or an amino acid sequence that can form a tetrameric coiled coil).

In some embodiments, the retrovirus is combined with the population of cells in (ii) for one minute to seventy-two hours and at a temperature ranging from 4° C. to 42° C. In some embodiments, the retrovirus and the population of cells are combined in (ii) in the presence of (a) a cell culture media, optionally RPMI or DMEM cell culture media; (b) a buffered saline solution, optionally phosphate-buffered saline or HEPES-buffered saline; and/or (c) an enhancer of retroviral transduction, optionally heparin sulfate, poly-brene, protamine sulfate, and/or dextran. In some embodi-ments, the extracellular targeting domain is capable of binding to a cognate protein (e.g., a protein receptor) that is present on the cell surface of a subset of the population of cells. In some embodiments, the population of cells is washed between (ii) and (iii) (e.g., using phosphate-buffered saline (PBS), e.g., to remove the retrovirus from the popu-lation of cells). In some embodiments, sorting the population of cells is performed using fluorescence-activated cell sort-ing, single-cell next-generation sequencing, or antibiotic selection.

In some embodiments, the methods further comprise a second retrovirus, wherein the second retrovirus comprises a different extracellular targeting domain and/or a different reporter compared to the first retrovirus.

Other aspects of the disclosure provide methods of deliv-ering a nucleic acid (e.g., a gene of interest, e.g., that encodes a protein) to an cell, the method comprising (i) providing a retrovirus comprising the nucleic acid, a viral envelope protein comprising at least one mutation that diminishes its native function, and a non-viral membrane-bound protein comprising an extracellular targeting domain that is capable of binding to a cognate ligand of the cell; and (ii) contacting the retrovirus with the cell, thereby delivering the nucleic acid to the cell. In some embodiments, the retrovirus enters or infects the cell during (ii).

Some aspects of the disclosure provide methods of deliv-ering a nucleic acid to a cell, the method comprising (i) providing a retrovirus comprising the nucleic acid, a viral envelope protein comprising at least one mutation that diminishes its native function, and a CD80 protein domain; and (ii) contacting the retrovirus with the cell, thereby delivering the nucleic acid to the cell.

Yet other aspects of the disclosure provide methods of detecting an interaction between a retrovirus and an cell, the method comprising: (i) contacting a sample comprising the retrovirus and an cell with an antibody, wherein the retro-virus comprises a viral envelope protein comprising at least one mutation that diminishes its native function, a non-viral membrane-bound protein comprising an extracellular target-ing domain, and wherein the antibody binds to the extra-cellular targeting domain of the retrovirus; (ii) optionally removing unbound antibody from the sample; and (iii) imaging the sample to detect whether the antibody-retrovi-rus complex is bound to the cell.

In some embodiments, the antibody further comprises a fluorescent label, optionally wherein the antibody is cova-lently linked to a fluorescent label. In some embodiments, the sample is imaged in (iii) using confocal or fluorescence microscopy.

Some aspects of the disclosure provide libraries of retro-viruses, comprising a plurality of unique retroviruses, wherein each unique retrovirus comprises a viral envelope protein comprising at least one mutation that diminishes its native function, a non-viral membrane-bound protein com-prising a membrane-bound domain and an extracellular targeting domain (e.g., comprising at least 5, at least 10, at least 15, at least 20, or at least 50 amino acids), and a nucleic acid encoding a reporter, and wherein each unique retrovirus comprises a different and unique extracellular targeting domain.

In some embodiments, a library is capable of being screened against a population of antigen-specific cells, optionally wherein the antigen-specific cells are B cells or T cells. A library may comprise at least $10^2$, at least $10^3$, at least $10^4$, at least $10^5$, at least $10^6$, at least $10^7$, at least $10^8$, at least $10^9$, or at least $10^{10}$ unique retroviruses. In some embodiments, each different and unique extracellular target-ing domain is generated through site-directed mutagenesis.

Some aspects of the disclosure provide populations of cells, wherein a subset of the population of cells contain a retrovirus comprising: a viral envelope protein comprising at least one mutation that diminishes its native function, a non-viral membrane-bound protein comprising a mem-brane-bound domain and an extracellular targeting domain, and a nucleic acid encoding a reporter. In some embodi-ments, a subset of the population of cells (e.g., antigen-specific cells, e.g., B cells or T cells) contains a retrovirus as described herein. In some embodiments, the subset of the population of cells contains a retrovirus inside each cell of the subset. The subset of the population that contain the retrovirus may be isolated and/or sorted from the cells of the population that do not contain the retrovirus.

BRIEF DESCRIPTION OF THE DRAWINGS

FIG. 3A demonstrates that the binding inter-action of an extracellular targeting domain present in a retrovirus to a cognate ligand of a target cell leads to entry of the retrovirus and subsequent expression of reporter (GFP). FIG. 3B demonstrates that contacting a retrovirus with a non-target cell does not lead to entry of the retrovirus.

FIGS. 5A-5B depict graphs showing that T cell signaling is active during retroviral entry or infection. FIG. 5A dem-onstrates that the binding interaction of an extracellular targeting domain present in a retrovirus to a cognate ligand of a target cell leads to entry of the retrovirus and T cell signaling activation. FIG. 5B demonstrates that contacting a retrovirus with a non-target cell does not lead to entry of the retrovirus or T cell signaling activation.

FIG. 7A demonstrates that the binding inter-action of an interleuken-13 (IL-13) protein domain present in a retrovirus to an IL-13 protein receptor of a target cell leads to entry of the retrovirus and subsequent expression of reporter (GFP). FIG. 7B demonstrates that contacting a retrovirus comprising an IL-13 protein domain with a non-target cell that does not express an IL-13 protein receptor does not lead to entry of the retrovirus.

FIG. 16A shows the ability of NYESO-1 displaying lentiviruses to transduce IG4-expressing T cells. SL-1 displaying lentiviruses do not transduce IG4-expressing T cells. FIG. 16B shows the mean fluorescence provided by the interaction between NYESO-1 displaying lentiviruses and IG4-expressing T cells.

FIG. 18A depicts an exemplary binding schematic. FIG. 18B depicts graphs showing ability of retroviral constructs to interact with a target cell.

FIG. 22A depicts the transduction rate for each lentivirus. FIG. 22B depicts graphs showing FACS data for GL9 virus and NYESO-1 virus.

DETAILED DESCRIPTION OF THE INVENTION

Figure 1:
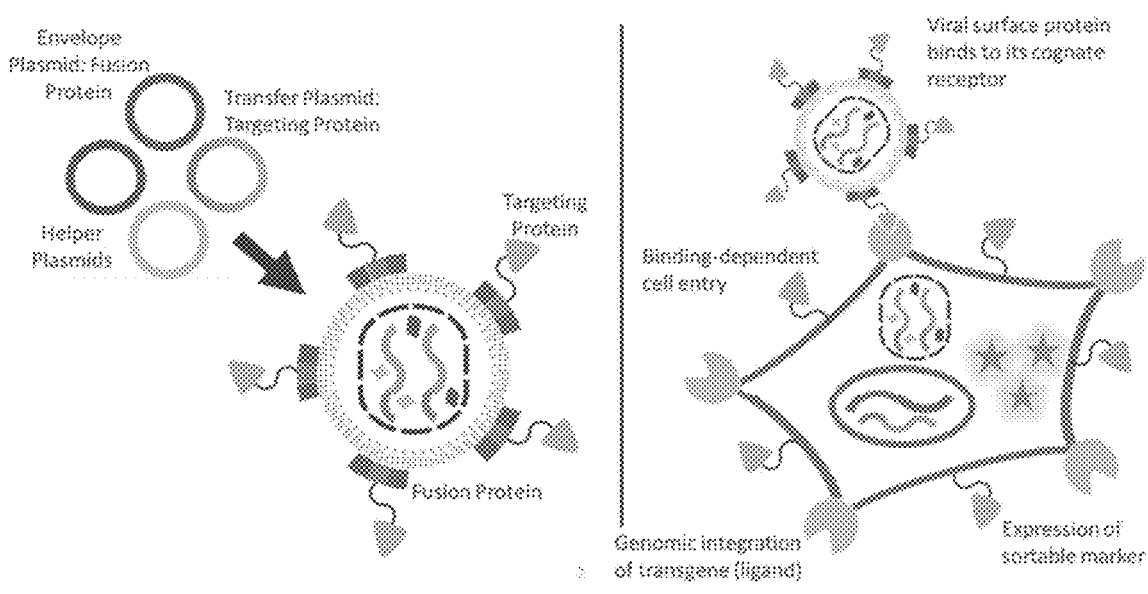
FIG. 1 depicts an exemplary schematic of a retrovirus of the current invention interacting with a cognate ligand of a target cell.

Herein are provided new and innovative methods, for example, to screen cells that are notoriously challenging to screen for specific antigens and function (e.g., T cells), and to deliver nucleic acids to target cells in a target-specific manner. In some embodiments, described herein are systems that enable, for example, repertoire-scale analysis of T cell receptor (TCR)-peptide-Major Histocompatibility Complex (pMHC) specificity, a previously intractable bottleneck, as previously described methods required considerable effort to determine what a single T cell clone can recognize (e.g., as in a typical immune response). In some embodiments, described herein are retrovirus-based systems that repurpose viral tropism as a method of selecting for molecular interactions and replace the binding functions of wild-type virus surface proteins with those of protein variants of interest, for example, by encoding these protein variants on the corresponding transfer plasmid used to make the virus, thereby ensuring that the resulting virus displays the protein variant on its surface and packaging the corresponding genetic sequence. As such, when the virus enters a target cell (e.g., bearing a receptor that binds the displayed extracellular targeting domain of the protein variant), cell entry results in integration of the genetic sequence of the displayed protein into the genome of the target cell.

Previous approaches for studying T cell specificity required a combination of generated T cell lines, recombinant expression of T cell receptors, and/or the individual validation of T cell binding or activity via a candidate antigen-based approach. Each of these elements provided an inherent limitation in the throughput of T cells or antigens screened. For example, yeast display based methods to deorphanize T cell receptors alleviated the bottleneck of number of antigens examined (with the ability to screen $>10^8$ ligands), but were still severely limited by the need to recombinantly express TCRs. The current strategies of the present invention described herein represents a tremendous advance in the study of T cell specificity and screening of T cells by allowing for screening of $>10^8$ ligands and without need for recombinant TCR expression.

Retroviruses

Described herein are retroviruses comprising a viral envelope protein comprising at least one mutation that diminishes its native function, a non-viral membrane-bound protein comprising a membrane-bound domain and an extracellular targeting domain, and a nucleic acid encoding a reporter. In some embodiments, a retrovirus comprises a viral envelope protein comprising at least one mutation that diminishes its native function and a non-viral membrane-bound protein comprising a membrane-bound domain and an extracellular targeting domain.

The retrovirus disclosed herein comprise one or more elements derived from a retroviral genome (naturally-occurring or modified) of a suitable species. Retroviruses include 7 families: alpharetrovirus (Avian leucosis virus), betaretrovirus (Mouse mammary tumor virus), gammaretrovirus (Murine leukemia virus), deltaretrovirus (Bovine leukemia virus), epsilonretrovirus (Walleye dermal sarcoma virus), lentivirus (Human immunodeficiency virus 1), and spumavirus (Human spumavirus). Six additional examples of retroviruses are provided in U.S. Pat. No. 7,901,671.

In some embodiments, a retrovirus is a lentivirus. Lentivirus is a genus of retroviruses that typically gives rise to slowly developing diseases due to their ability to incorporate into a host genome. Modified lentiviral genomes are useful as viral vectors for the delivery of a nucleic acids to a host cell. Host cells can be transfected with lentiviral vectors, and optionally additional vectors for expressing lentiviral packaging proteins (e.g., VSV-G, Rev, and Gag/Pol) to produce lentiviral particles in the culture medium.

Retrovirus and lentivirus constructs are well known in the art and any suitable retrovirus can be used to construct the retrovirus (or a plurality or library of retroviruses) as described herein. Non-limiting examples of retrovirus constructs include lentiviral vectors, human immunodeficiency viral (HIV) vector, avian leucosis viral (ALV) vector, murine leukemia viral (MLV) vector, murine mammary tumor viral (MMTV) vector, murine stem cell virus, and human T cell leukemia viral (HTLV) vector. These retrovirus constructs comprise proviral sequences from the corresponding retrovirus.

The retrovirus described herein may comprise the viral elements such as those described herein from one or more suitable retroviruses, which are RNA viruses with a single strand positive-sense RNA molecule. Retroviruses comprise a reverse transcriptase enzyme and an integrase enzyme. Upon entry into a target cell, retroviruses utilize their reverse transcriptase to transcribe their RNA molecule into a DNA molecule. Subsequently, the integrase enzyme is used to integrate the DNA molecule into the host cell genome. Upon integration into the host cell genome, the sequence from the retrovirus is referred to as a provirus (e.g., proviral sequence or provirus sequence). The retroviral vectors described herein may further comprise additional functional elements as known in the art to address safety concerns and/or to improve vector functions, such as packaging efficiency and/or viral titer. Additional information may be found in US20150316511 and WO2015/117027, the relevant disclosures of each of which are herein incorporated by reference for the purpose and subject matter referenced herein. Additional information for lentiviruses can be found in, e.g., WO2019/056015, the relevant disclosures of which are incorporated by reference herein for this particular purpose.

In some embodiments, lentiviruses are able to be targeted to target-specific cells via the pMHC-TCR interaction or any other protein-protein cell-to-cell interaction. In some embodiments, T cells with a known and relevant specificity can be enhanced (in the case of cancer or infection) or ablated (in the case of autoimmunity) without affecting other T cells, dramatically limiting the risk of off-target effects. In some embodiments, lentiviruses may encode an extracellular domain to target any other surface-expressed molecule on a target cell.

Viral Envelope Protein

The retroviruses described herein comprise a viral envelope protein comprising at least one mutation that diminishes its native function (e.g., wild-type function of a non-mutated viral envelope protein). In some embodiments, a viral envelope protein is any viral envelope protein of any retrovirus (e.g., lentivirus). A viral envelope protein may be a VSV-G envelope protein, a measles virus envelope protein, a nipah virus envelope protein, or a cocal virus G protein. In some embodiments, the native function that is diminished by a mutation of a viral envelope protein is viral tropism (e.g., ability to infect cells, bind to cells, etc.) In some embodiments, a viral envelope protein comprising at least one mutation that diminishes its native function is a mutated VSV-G envelope protein. In some embodiments, a viral envelope protein comprising at least one mutation that diminishes its native function is a mutated measles virus envelope protein. In some embodiments, a viral envelope protein comprising at least one mutation that diminishes its native function is a mutated nipah virus envelope protein. In some embodiments, a viral envelope protein comprising at least one mutation that diminishes its native function is a mutated cocal virus G protein.

In some embodiments, a mutated VSV-G envelope protein comprises a mutation at H8, K47, Y209, and/or R354. In some embodiments, a mutated VSV-G envelope protein comprises a H8A, K47A, K47Q, Y209A, R354A, and/or R354Q mutation. In some embodiments, a mutated VSV-G envelope protein is as described in Nikolic et al., "Structural basis for the recognition of LDL-receptor family members by VSV glycoprotein." Nature Comm., 2018, 9:1029, the relevant disclosures of which are incorporated by reference herein for this particular purpose.

In some embodiments, a mutated measles virus envelope protein comprises a mutation at Y481, R533, S548, and/or F549. In some embodiments, a mutated measles virus envelope protein comprises a Y481A, R533A, S548L, and/or F549S mutation.

In some embodiments, a mutated Nipah virus envelope protein comprises a mutation at E501, W504, Q530, and/or E533. In some embodiments, a mutated measles virus envelope protein comprises a E501A, W504A, Q530A, and/or E533A mutation.

In some embodiments, a mutated cocal virus G protein comprises a mutation at K64 and/or R371. In some embodiments, a mutated cocal virus G protein comprises a mutation at K64Q and/or R371A.

In some embodiments, the mutated envelope protein is derived from any other enveloped virus including but not limited to baculovirus, herpes simplex virus (HSV), cytomegalovirus (CMV), lymphocytic choriomeningitis virus (LCMV), Epstein-Barr virus (EBV), vaccinia virus, Hepatitis A, B, or C virus, vaccinia virus, alphavirus, dengue virus, yellow fever virus, Zika virus, influenza virus, hantavirus, Ebola virus, rabies virus, human immunodeficiency virus (HIV), coronavirus, and other members of rhabdoviridae.

In some embodiments, a viral envelope protein comprising at least one mutation comprises 1, 2, 3, 4, 5, 6, 7, 8, 9, 10, or more mutations. In some embodiments, a viral envelope protein comprising at least one mutation comprises a nucleotide sequence and/or amino acid sequence that is at least 50%, 60%, 70%, 80%, 90%, 95%, or 97% identical to a wild-type viral envelope protein. In some embodiments, a viral envelope protein comprising at least one mutation that diminishes its native function retains less than 95%, 90%, 80%, 70%, 60%, 50%, 40%, 30%, 20%, or 10% of the function of a wild-type viral envelope protein. In some embodiments, a viral envelope protein comprising at least one mutation lacks all of its native function. In some embodiments, a retrovirus comprising a viral envelope protein comprising at least one mutation that diminishes its native function comprises less than 95%, 90%, 80%, 70%, 60%, 50%, 40%, 30%, 20%, or 10% of the cellular infectivity of a retrovirus comprising a wild-type viral envelope protein.

Non-Viral Membrane-Bound Protein

The retroviruses described herein comprise a non-viral membrane-bound protein. A non-viral membrane-bound protein may comprise a membrane-bound domain and an extracellular targeting domain. In some embodiments, a non-viral membrane-bound protein is a chimeric protein comprising sequences from at least two different proteins. In some embodiments, a non-viral membrane-bound protein is a full-length or truncated protein comprising sequence from a single protein.

A membrane-bound domain is a protein or peptide that has an amino acid sequence that enables the protein or peptide to be fully or partially embedded or associated with the membrane (e.g., envelope) of the retrovirus. In some embodiments, a membrane-bound domain enables presentation and delivery of the extracellular targeting domain to the extracellular environment. In some embodiments, a membrane-bound domain comprises an intracellular domain, a transmembrane domain, and/or an extracellular domain. In some embodiments, a membrane-bound domain comprises an intracellular domain and a transmembrane domain. In some embodiments, the membrane-bound domain comprises a Major Histocompatibility Complex (MHC) protein or fragment thereof. A MHC protein may be a Class I or Class II MHC protein.

In some embodiments, a membrane-bound domain comprises 10-50, 10-100, 25-100, 50-200, 50-150, 100-500, 100-250, 250-500, or any reasonable number of total amino acids.

In some embodiments, a retrovirus present in a library of retroviruses comprises the same membrane-bound domain as some or all of the other retroviruses in the library. In some embodiments, each retrovirus present in a library of retroviruses comprises a different membrane-bound domain relative to some or all of the other retroviruses in the library.

In some embodiments, an extracellular targeting domain is any protein or peptide that has an amino acid sequence and is a binding partner for a target molecule or ligand (e.g., a cognate protein) on a cell surface. When present in the extracellular environment beyond the interior of the retrovirus, an extracellular targeting domain is capable of binding to a target cell. In some embodiments, an extracellular targeting domain binds or targets to a cognate protein or ligand (e.g., a protein receptor present on a target cell) that is present on the cell surface of a cell or a subset of a population of cells. In some embodiments, an extracellular targeting domain binds to a cognate protein or ligand that is present on the cell surface of a single T cell or a subset of a population of T cells. In some embodiments, a binding interaction between an extracellular targeting domain of a retrovirus and a cognate protein or ligand of a cell enables the retrovirus to enter the cell (e.g., an antigen-specific cell, e.g., a T cell).

In some embodiments, an extracellular targeting domain comprises 10-50, 10-100, 25-100, 50-200, 50-150, 100-500, 100-250, 250-500, or any reasonable number of total amino acids. In some embodiments, an extracellular targeting domain comprises at least 5, at least 10, at least 15, at least 20, or at least 50 amino acids.

In some embodiments, an extracellular targeting domain is a protein, an antibody or peptide. In some embodiments, an antibody is a full-length antibody, an antibody fragment, a nanobody, or a single chain antibody (scFv). In some embodiments, an extracellular targeting domain is an antibody that binds to a cognate protein of a target cell. In some embodiments, an extracellular targeting domain is an antibody that binds to a B-cell or T cell antigen. In some embodiments, an extracellular targeting domain is an anti-CD19 antibody (e.g., an antibody that binds to CD19). In some embodiments, an extracellular targeting domain is an antibody that binds to any cell surface molecule. In some embodiments, an extracellular targeting domain is an antibody that binds to a lineage marker (e.g., CD3, CD20, integrins, or other receptors), phenotypic markers (PD-1, CD25, CD45, or others). In some embodiments, an extracellular targeting domain is a protein or peptide that binds to a receptor (e.g., a receptor that is present on the surface of a target cell). In some embodiments, an extracellular targeting domain is a protein or peptide that binds to a cytokine receptor (e.g., interleukin-13 (IL-13) receptor). In some embodiments, an extracellular targeting domain is a cytokine (e.g., IL-2, IL-6, IL-12, IL-13). In some embodiments, an extracellular targeting domain is a chemokine ligand (e.g. CXCL9, CXCL10, CXCL 11, etc.). In some embodiments, an extracellular targeting domain is a cellular receptor, including cytokine receptors (e.g. IL-13Rα1, IL-13Rα2, IL-2 receptors, common gamma chain), GPCRs (including chemokine receptors such as CSCR3, CXCR4, etc.), and integrins. In some embodiments, an extracellular targeting domain is a peptide that is displayed by a MHC protein. In some embodiments, non-viral membrane-bound protein comprises a membrane-bound domain comprising a MHC protein or fragment and an extracellular targeting domain comprising a peptide that is displayed by a MHC protein. In some embodiments, an extracellular domain binds to a T cell receptor and/or a B cell receptor. T-cell receptors are expressed in nature on the surface of T-cells usually as alpha/beta and gamma/delta heterodimeric integral membrane proteins, each subunit comprising a short intracellular segment, a single transmembrane alpha-helix and two globular extracellular Ig-superfamily domains. B-cell receptors are transmembrane receptor proteins located on the outer surface of B cells.

In some embodiments, an extracellular targeting domain binds to a target cell or cell surface molecule with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, an extracellular targeting domain binds to a cognate protein or ligand of a target cell with a binding affinity of 10-9 to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, the binding affinity between an extracellular targeting domain and a cognate protein or ligand is in the picomolar to nanomolar range (e.g., between about $10^{-12}$ and about $10^{-9}$ M). In some embodiments, the binding affinity between an extracellular targeting domain and a cognate protein or ligand is in the nanomolar to micromolar range (e.g., between about $10^{-9}$ and about $10^{-6}$ M). In some embodiments, the binding affinity between an extracellular targeting domain and a cognate protein or ligand is in the micromolar to millimolar range (e.g., between about $10^{-6}$ and about $10^{-3}$ M). In some embodiments, the binding affinity between an extracellular targeting domain and a cognate protein or ligand is in the picomolar to micromolar range (e.g., between about $10^{-12}$ and about $10^{-6}$ M). In some embodiments, the binding affinity between an extracellular targeting domain and a cognate protein or ligand is in the nanomolar to millimolar range (e.g., between about $10^{-9}$ and about $10^{-3}$ M).

As used herein, the term antibody generally refers to a protein that includes at least one immunoglobulin variable domain or immunoglobulin variable domain sequence. For example, an antibody can include a heavy (H) chain variable region (abbreviated herein as $V_H$), and/or a light (L) chain variable region (abbreviated herein as $V_L$). In another example, an antibody includes two heavy (H) chain variable regions and/or two light (L) chain variable regions. An antibody can have the structural features of IgA, IgG, IgE, IgD, IgM (as well as subtypes thereof). The $V_H$ and $V_L$ regions can be further subdivided into regions of hypervariability, termed "complementarity determining regions" ("CDR"), interspersed with regions that are more conserved, termed "framework regions" ("FR"). Each $V_H$ and/or $V_L$ is typically composed of three CDRs and four FRs, arranged from amino-terminus to carboxy-terminus in the following order: FR1, CDR1, FR2, CDR2, FR3, CDR3, FR4. The $V_H$ or $V_L$ chain of the antibody can further include a heavy or light chain constant region, to thereby form a heavy or light immunoglobulin chain, respectively. In some embodiments, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3.

In some embodiments, a retrovirus present in a library of retroviruses comprises the same extracellular targeting domain as some or all of the other retroviruses in the library. In some embodiments, each retrovirus present in a library of retroviruses comprises a different extracellular targeting domain relative to some or all of the other retroviruses in the library.

In some embodiments, a non-viral membrane-bound protein further comprises a signal sequence (also referred to as a signal peptide of localization sequence). In some embodiments, the signal sequence is at the N- or C-terminal ends of the non-viral membrane-bound protein. A signal sequence functions to translocate the non-viral membrane-bound protein to the membrane (or envelope) of the retrovirus. In some embodiments, a signal sequence is 5-10, 5-15, 10-20, 15-20, 15-30, 20-30, or 25-30 amino acids. In some embodiments, the signal sequence is an Ig Kappa leader sequence (e.g., a murine Ig Kappa leader sequence comprising: METDTLLL-WVLLLWVPGSTG (SEQ ID NO: 1)) or a B2M signal peptide sequence (e.g., a B2M signal peptide sequence comprising: MSRSVALAVLALLSLSGLEA (SEQ ID NO: 2)). In some embodiments, a retrovirus present in a library of retroviruses comprises the same signal sequence as some or all of the other retroviruses in the library. In some embodiments, each retrovirus present in a library of retroviruses comprises a different signal sequence relative to some or all of the other retroviruses in the library.

In some embodiments, a nucleic acid encoding a non-viral membrane-bound protein further comprises an internal ribosome entry site (IRES). An IRES is an RNA sequence that allows for initiation of translation during protein synthesis. In some embodiments, the IRES is located at or near the C-terminal end. In some embodiments, the IRES is located C-terminal relative to the membrane-bound domain and the extracellular targeting domain. In some embodiments, the IRES is a viral IRES. In some embodiments, the IRES is an IRES that is native to the retrovirus. In some embodiments, the IRES is a sequence derived from encephalomyocarditis virus (EMCV). In some embodiments, a retrovirus present in a library of retroviruses comprises the same IRES as some or all of the other retroviruses in the library. In some embodiments, each retrovirus present in a library of retroviruses comprises a different IRES relative to some or all of the other retroviruses in the library.

In some embodiments, a non-viral membrane-bound protein further comprises a linker positioned between the membrane-bound domain and the extracellular targeting domain. A linker is an amino acid linker and may be a rigid linker, a flexible linker, or an oligomerized linker. A rigid linker is an amino acid sequence that lacks flexibility (e.g., may comprise at least one proline). In some embodiments, a rigid linker comprises a platelet-derived growth factor receptor (PDGFR) stalk or a CD8α stalk. In some embodiments, a PDGFR stalk comprises an amino acid sequence comprising AVGQDTQEVIVVPHSLPFK (SEQ ID NO: 3). In some embodiments, a PDGFR stalk comprises an amino acid sequence comprising ASAKPTTTPAPRPPTPAPTIA-SQPLSLRPEAARPAAGGAVHTRGLDFAK (SEQ ID NO: 4) A flexible linker is an amino acid sequence that has many degrees of freedom (e.g., may comprise a plurality of amino acids with small side chains, e.g., glycine or alanine). In some embodiments, a flexible linker comprises an amino acid sequence comprising GAPGAS (SEQ ID NO: 5). In some embodiments, a flexible linker comprises an amino acid sequence consisting of GAPGSGGGGSGGGGSAS (SEQ ID NO: 6). In some embodiments, a flexible linker comprises an amino acid sequence comprising GGGGS (SEQ ID NO: 7). In some embodiments, a flexible linker comprises an amino acid sequence comprising $(GAPGAS)_N$ (SEQ ID NO: 29) or $(G4S)_N$ (SEQ ID NO: 30), wherein N is 1, 2, 3, 4, 5, 6, 7, 8, 9, 10, or more. An oligomerized linker is an amino acid that can oligomerize to another related amino amid. In some embodiments, an oligomerized linker is an amino acid sequence that can form a dimer, trimer, or tetramer. In some embodiments, an oligomerized linker comprises an IgG4 hinge domain (e.g., ASESKY-GPPCPPCPAVGQDTQEVIVVPHSLPFK (SEQ ID NO: 8)). In some embodiments, an oligomerized linker comprises an amino acid sequence that can form a tetrameric coiled coil (e.g., ASGGGGSGELAAIKQELAAIKKELAAIKWE-LAAIKQGAG (SEQ ID NO: 9)). In some embodiments, an oligomerized linker comprises an amino acid sequence that can form a dimeric coiled coil (e.g., ASESKYGPPCPPCP (SEQ ID NO: 10)).

Reporter

In some embodiments, the retroviruses described herein may comprise a reporter (e.g., a reporter protein). In some embodiments, the retroviruses described herein comprise a nucleic acid encoding a reporter (e.g., a reporter protein). As used herein, a reporter is generally a protein or gene that can be detected when expressed in a retrovirus and/or target cell. In some embodiments, the presence or absence of a reporter in a target cell or a subset of a target cells in a population of cells allows for the ability to sort cells (e.g., using flow cytometry and/or fluorescence-activated cell sorting).

In some embodiments, a reporter is a fluorescent protein. A fluorescent protein may be a green fluorescent protein (GFP), yellow fluorescent protein (YFP), red fluorescent protein (RFP). A fluorescent protein may be as described in U.S. Pat. No. 7,060,869, entitled "Fluorescent protein sensors for detection of analytes".

In some embodiments, a reporter is an antibiotic resistance marker. In some embodiments, an antibiotic resistance marker is a protein or gene that confers a competitive advantage to a target cell that contains the marker. In some embodiments, the antibiotic resistance marker comprises a hygromycin resistance protein or gene, a kanamycin resistance protein or gene, ampicillin resistant protein or gene, streptromycin resistant protein or gene, or a neomycin resistance protein or gene.

Cells

A cell as described herein may be any bacterial, mammalian, or yeast cell. In some embodiments, a cell is a human, mouse, rat, or a non-human primate cell. In some embodiments, a cell is a somatic cell or a reproductive cell. In some embodiments, a cell is an epithelial cell, a neural cell, a hormone-secreting cell, an immune cell, a secretory cell, a blood cell, an interstitial cell, or a germ cell. In some embodiments, a cell is an antigen-specific cell (e.g., a cell that binds to a specific antigen). In some embodiments, an antigen-specific cell is an immune cell. In some embodiments, an antigen-specific cell is a B cell or a T cell. In some embodiments, a cell is a target cell (e.g., that comprises a cognate protein or ligand capable of being targeted by a retrovirus described herein)

A population of cells as described herein may be any bacterial, mammalian, or yeast cell population. In some embodiments, a population of cells is a population of human, mouse, rat, or non-human primate cells. In some embodiments, a population of cells is a somatic cell population or a reproductive cell population. In some embodiments, a population of cells comprises epithelial cells, neural cells, hormone-secreting cells, immune cells, secretory cells, blood cells, interstitial cells, and/or germ cells. In some embodiments, a population of cells comprises antigen-specific cells (e.g., cells that binds to a specific antigen). In some embodiments, a population of antigen-specific cells comprises immune cells. In some embodiments, a population of antigen-specific cells comprises B cells and/or T cells. In some embodiments, a population of cells comprises a homogenous population of cells. In some embodiments, a population of cells comprises a heterogeneous population of cells.

In some embodiments, a population of cells is a population of cells isolated from a subject. A subject may be a human subject (e.g., a human subject suffering from a disease), a mouse subject, a rat subject, or a non-human primate subject. In some embodiments, a population of cells is isolated from the blood or a tumor of a subject.

In some embodiments, a population of cells has been previously frozen and thawed (e.g., 1, 2, 3, 4, 5, or more freeze/thaw cycles). In some embodiments, a population of cells are maintained in liquid culture media. In some embodiments, a population of cells have been passaged 1, 2, 3, 4, 5, or more times, using any known method. In some embodiments, a population of cells are maintained in liquid culture media prior to being combined with a retrovirus or plurality of retroviruses. In some embodiments, a population of cells are maintained in liquid culture media after to being combined with a retrovirus or plurality of retroviruses. In some embodiments, a population of cells are maintained in liquid culture media prior to while being combined with a retrovirus or plurality of retroviruses.

In some embodiments, a population of cells comprises any of the retroviruses described herein. In some embodiments, a subset of a population of cells contain any of the retroviruses described herein. In some embodiments, a subset of a population of cells contains the retrovirus inside each cell of the subset (e.g., inside the nucleus of each cell of the subset). In some embodiments, a population of cells or a subset thereof expresses a reporter (e.g., a fluorescent protein or an antibiotic resistance marker). In some embodiments, a population of cells or a subset thereof (e.g., containing a retrovirus) are isolated and/or sorted based on the presence or absence of a reporter. In some embodiments, a subset of a population of cells that contain retrovirus described herein are isolated and/or sorted based on the presence or absence of a reporter away from the cells of the population that do not contain the retrovirus. In some embodiments, at least 50%, 60%, 70%, 80%, 90%, or 95% of a population of cells prior to cell sorting contain a retrovirus. In some embodiments, at least 70%, 80%, 90%, 95%, or 100% of a population of cells contain a retrovirus following isolation and/or sorting based on the presence or absence of a reporter.

Methods of Screening

Described herein are methods of screening a population of cells comprising: (i) providing a retrovirus comprising a viral envelope protein comprising at least one mutation that diminishes its native function, a non-viral membrane-bound protein comprising a membrane-bound domain and an extracellular targeting domain, and a nucleic acid encoding a reporter; (ii) combining the retrovirus with a population of cells; and (iii) sorting the population of cells based on the presence or absence of the reporter. In some embodiments, the retrovirus of (i) comprises a nucleic acid comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter; and a mutated viral envelope protein comprising at least one mutation that diminishes its native function.

As used herein, the term "combining" (which, in some embodiments, is synonymous with the terms "providing" and "contacting") generally refers to the act of bringing a retrovirus into close, physical contact with a population of cells, such that the extracellular targeting domain of the retrovirus is capable of binding to the cognate ligand present on a subset of cells of the population. In some embodiments, combining of a retrovirus and a population of cells occurs when a solution comprising the retrovirus and a solution comprising the population of cells are mixed. In some embodiments, combining of a retrovirus and a population of cells occurs when a lyophilized retrovirus and a solution comprising the population of cells are mixed. In some embodiments, combining of a retrovirus and a population of cells occurs when a lyophilized retrovirus and a lyophilized population of cells are mixed and reconstituted with a solution. In some embodiments, the cells of the population are maintained in cell culture media, in a monolayer of cells, and/or are attached to a tissue culture plate or petri dish.

Generally, a retrovirus and a population of cells are combined (e.g., physically combined or contacted) for a defined period of time. In some embodiments, a period of time is measured in seconds, minutes, hours or days. In some embodiments, period of time is 0-30 seconds, 15-45 seconds, 30-60 seconds, 45-90 seconds, 60-90 seconds, or 60-120 seconds. In some embodiments, a retrovirus and a population of cells are combined and in contact for 0-30 seconds, 15-45 seconds, 30-60 seconds, 45-90 seconds, 60-90 seconds, or 60-120 seconds. In some embodiments, period of time is 1-2 minutes, 1-5 minutes, 1-10 minutes, 2-10 minutes, 5-10 minutes, 5-20 minutes, 10-20 minutes, 25-30 minutes, 25-60 minutes, 30-45 minutes, 30-40 minutes, 40-60 minutes, 50-70 minutes, or 60-120 minutes. In some embodiments, a retrovirus and a population of cells are combined and in contact for 1-2 minutes, 1-5 minutes, 1-10 minutes, 2-10 minutes, 5-10 minutes, 5-20 minutes, 10-20 minutes, 25-30 minutes, 25-60 minutes, 30-45 minutes, 30-40 minutes, 40-60 minutes, 50-70 minutes, or 60-120 minutes. In some embodiments, a period of time is 1-2 hours, 1-5 hours, 1-3 hours, 2-5 hours, 3-6 hours, 3-12 hours, 6-12 hours, 12-18 hours, 12-24 hours, 15-30 hours, 18-24 hours, 24-48 hours, 24-36 hours, or 36-50 hours. In some embodiments, a retrovirus and a population of cells are combined and in contact for 1-2 hours, 1-5 hours, 1-3 hours, 2-5 hours, 3-6 hours, 3-12 hours, 6-12 hours, 12-18 hours, 12-24 hours, 15-30 hours, 18-24 hours, 24-48 hours, 24-36 hours, or 36-50 hours. In some embodiments, a period of time is 1, 2, 3, 4, 5, 6, 7, 8, 9, 10, or 5-15 days. In some embodiments, a retrovirus and a population of cells are combined and in contact for 1, 2, 3, 4, 5, 6, 7, 8, 9, 10, or 5-15 days.

In some embodiments, a population of cells are sorted based on the presence or absence of the reporter. In some embodiments, a subset of the population of cells containing the reporter (e.g., express the reporter) are sorted from the remaining subset of the population of cells that do not contain the reporter. In some embodiments, sorting of the population of cells is performed using flow cytometry (e.g., fluorescence-activated cell sorting), next-generation genome sequencing (e.g., single-cell next-generation sequencing), or antibiotic selection.

In some embodiments, the conditions of step (ii) that allow for the retrovirus to have cell-to-cell interactions with a subset of the population of cells comprise combining the retrovirus and the population of cells in the presence of defined solutions, compositions and at specific temperatures. In some embodiments, the retrovirus and the population of cells are combined in the presence of a cell culture media (e.g., RPMI or DMEM cell culture media). In some embodiments, the retrovirus and the population of cells are combined in the presence of a buffered saline solution. In some embodiments, a buffered saline solution is a phosphate-buffered saline or HEPES-buffered saline. In some embodiments, a buffered saline solution comprises bovine serum albumin and/or EDTA. In some embodiments, the retrovirus and the population of cells are combined in the presence of an enhancer of retroviral transduction (e.g., heparin sulfate, polybrene, protamine sulfate, or dextran). In some embodiments, the retrovirus and the population of cells are combined in (ii) at a temperature ranging from 4° C. to 42° C., 4° C. to 8° C., 4° C. to 10° C., 8° C. to 15° C., 10° C. to 20° C., 18° C. to 23° C., 20° C. to 30° C., 25° C. to 35° C., 30° C. to 40° C., or 37° C. to 42° C.

In some embodiments, the methods of screening described herein further comprise washing the population of cells between steps (ii) and (iii) with a wash solution. In some embodiments, a wash solution is any liquid solution that allows for maintenance of healthy cells (e.g., solution comprising neutral pH, low-to-moderate levels of ionic strength). In some embodiments, washing the population of cells removes excess and/or remaining retrovirus from the population of cells. In some embodiments, the population of cells are washed using a cell culture media (e.g., RPMI or DMEM cell culture media). In some embodiments, the population of cells are washed using a buffered saline solution. In some embodiments, a buffered saline solution is a phosphate-buffered saline or HEPES-buffered saline. In some embodiments, a buffered saline solution comprises bovine serum albumin and/or EDTA. In some embodiments, the population of cells are washed at a temperature ranging from 4° C. to 42° C., 4° C. to 8° C., 4° C. to 10° C., 8° C. to 15° C., 10° C. to 20° C., 18° C. to 23° C., 20° C. to 30° C., 25° C. to 35° C., 30° C. to 40° C., or 37° C. to 42° C.

In some embodiments, the population of cells are maintained in liquid culture prior to being combined with the retrovirus. In some embodiments, the population of cells are maintained in liquid culture after being combined with the retrovirus. In some embodiments, the population of cells are maintained in liquid culture during the combining step with the retrovirus. In some embodiments, the population of cells are attached to a cell culture plate or petri dish. In some embodiments, the population of cells are maintained in a monolayer, an embryoid body, or any cell aggregate.

In some embodiments, methods of screening comprise the use of a plurality of retroviruses. In certain embodiments, a plurality of retroviruses comprises at least $10^2$, $10^3$, $10^4$, $10^5$, $10^6$, $10^7$, $10^8$, $10^9$, $10^{10}$, $10^{11}$, or $10^{12}$ unique retroviruses. In some embodiments, there may be at least $10^2$, $10^3$, $10^4$, $10^5$, $10^6$, $10^7$, $10^8$, $10^9$, $10^{10}$, $10^{11}$, or $10^{12}$ copies of each unique retrovirus present in a plurality of retroviruses.

In some embodiments, methods of screening comprise screening a population of cells with at least two different, unique retroviruses. In some embodiments, a different, unique retrovirus comprises a different extracellular targeting domain and/or a different reporter. In some embodiments, methods of screening comprise a first retrovirus and a second retrovirus, wherein the first and second retrovirus comprise different extracellular targeting domains and/or different reporters. In some embodiments, methods of screening comprise screening a population of cells with 2, 3, 4, 5, 6, 7, 8, 9, 10, 50, 100 or more different retroviruses. In some embodiments, methods of screening comprise screening a population of cells with a library of retroviruses. In some embodiments, a library of retroviruses comprises at least $10^2$, at least $10^3$, at least $10^4$, at least $10^5$, at least $10^6$, at least $10^7$, at least $10^8$, at least $10^9$, or at least $10^{10}$ unique retroviruses.

Library of Retroviruses

Described herein are libraries of retroviruses, wherein a library comprises a plurality of unique retroviruses, wherein each unique retrovirus comprises a viral envelope protein comprising at least one mutation that diminishes its native function, a non-viral membrane-bound protein comprising a membrane-bound domain and an extracellular targeting domain, and a nucleic acid encoding a reporter, and wherein each unique retrovirus comprises a different and unique extracellular targeting domain. Also described herein are libraries of cells comprising retroviruses, wherein a library comprises a plurality of unique cells, wherein each unique cell comprises a unique retrovirus.

In some embodiments, libraries include pMHC-encoded (peptide/MHC-encoded) retroviral (e.g., lentiviral) libraries for use in screening populations of T cells. In such libraries, the pMHC displayed on the virus surface will enable T cell infection in a TCR-specific manner. Infected T cells can be collected and sequenced, allowing for the identification of pMHC ligands can infect a subset of a T cell population of interest and the ability to simultaneously track TCR sequences and reactive pMHC ligands. In some embodiments, pMHC retroviral libraries minimally comprise randomized transfer vectors containing randomized pMHC targeting elements. In some embodiments, randomly derived libraries are generated using degenerate oligonucleotide primers. In some embodiments, targeted libraries that are specific for a unique set of antigens (e.g., all possible viral or bacterial antigens for a particular target of interest— human immunodeficiency virus, tuberculosis TB, etc.; or all possible neoantigens for a particular subject) are generated.

In some embodiments, a library is capable of being screened against a population of antigen-specific cells (e.g., B cells or T cells). In some embodiments, a library comprises at least $10^2$, at least $10^3$, at least $10^4$, at least $10^5$, at least $10^6$, at least $10^7$, at least $10^8$, at least $10^9$, or at least $10^{10}$ unique retroviruses. In some embodiments, a library comprising unique retroviruses comprises extracellular targeting domains that are at least 5, at least 10, at least 15, at least 20, or at least 50 amino acids in length. In some embodiments, each different and unique extracellular targeting domain is generated through site-directed mutagenesis.

Retroviral or cell libraries can vary in size from hundreds to hundreds of thousands, millions, or more unique retroviruses or unique cells. In some embodiments, the libraries of the disclosure comprise at least 500,000 unique retroviruses or unique cells. The libraries of the invention include retroviral libraries and cellular libraries. A library is a synthetic (i.e., isolated, synthetically produced, free from components that are naturally found together in a cell, purified before being put into the library) collection of members having a common element and at least one distinct element. The library comprises a thousand or more (e.g., at least: 1,000; 2,000; 3,000; 4,000; 5,000; 10,000; 50,000; 100,000; 500,000; 600,000; 700,000; 800,000; 900,000; 1,000,000; 2,000,000; 3,000,000; 4,000,000; or more) members. The upper limit of the library size is defined by the combinatorics of domains or modules providing distinctness or diversity among the members. For instance, an upper limit may be 4,000,000 members. Thus, in some embodiments, the library is highly diverse, and includes at least 500,000 distinct members. The highly diverse library may have a diversity of $10^6$ or greater. In some embodiments, a library of retroviruses is generated using site-directed mutagenesis of a nucleic acid described herein. In some embodiments, the site-directed mutagenesis involves the use of primers and a low-fidelity RNA polymerase to allow for randomized mutagenesis of a common nucleic acid as described herein.

Methods of delivering nucleic acid to a cell Described herein are methods of delivering a nucleic acid to a cell, comprising (i) providing a retrovirus, as described herein, comprising the nucleic acid, a viral envelope protein comprising at least one mutation that diminishes its native function, and a non-viral membrane-bound protein comprising an extracellular targeting domain that is capable of binding to a cognate ligand of the cell; and (ii) contacting the retrovirus with the cell such that the retrovirus enters or infects the cell. In some embodiments, the nucleic acid encodes an mRNA molecule, optionally wherein the mRNA is a gene of interest. In some embodiments, the nucleic acid encodes a double-stranded RNA, an antisense RNA, a microRNA, or any other RNA molecule.

In some embodiments, the gene of interest encodes a protein. In some embodiments, the gene of interest encodes a therapeutic protein (e.g., a protein to compensate for a diseased condition in a subject).

In some embodiments, the nucleic acid is delivered to the cell when the retrovirus enters or infects the cell during step (ii). In some embodiments, the methods of delivering a nucleic acid described herein do not require a transfection agent (e.g., a lipophilic transfection agent such as Lipofectin).

Methods of detection Described herein are methods of detecting an interaction between a retrovirus and a cell, comprising: (i) contacting a sample comprising the retrovirus and an cell with an antibody, wherein the retrovirus comprises a viral envelope protein comprising at least one mutation that diminishes its native function, a non-viral membrane-bound protein comprising an extracellular targeting domain, and wherein the antibody binds to the extracellular targeting domain of the retrovirus; (ii) optionally removing unbound antibody from the sample; and (iii) imaging the sample to detect whether the antibody-retrovirus complex is bound to the cell.

In some embodiments, the antibody further comprises at least one fluorescent label. In some embodiments, a fluorescent label is a xanthene derivative (e.g., fluorescein, rhodamine, Oregon green, eosin and Texas red), cyanine derivative (e.g., cyanine, indocarbocyanine, oxacarbocyanine, thiacarbocyanine and merocyanine), naphthalene derivative (e.g., dansyl and prodan derivatives), coumarin derivative, oxadiazole derivative (e.g., pyridyloxazole, nitrobenzoxadiazole and benzoxadiazole), pyrene derivative (e.g., cascade blue), oxazine derivative (e.g., Nile red, Nile blue, cresyl violet and oxazine 170), acridine derivative (e.g., proflavin, acridine orange and acridine yellow), arylmethine derivative (e.g., auramine, crystal violet and malachite green), or tetrapyrrole derivative (e.g., porphin, phthalocyanine and bilirubin). The fluorescent label may be non-covalently associated with the antibody or covalently linked to the antibody.

In some embodiments, the sample is imaged in step (iii) using confocal or fluorescence microscopy. In some embodiments, methods of detection can be accomplished using standard microscopy setups (e.g., confocal or fluorescence microscopes). In some embodiments, a sample is detected in an ultra-multiplexed format while imaging using standard confocal or epi-fluorescence microscope.

Nucleic Acids

As used herein, the term "nucleic acids" generally refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). Nucleic acids include DNA such as D-form DNA and L-form DNA and RNA, as well as various modifications thereof. Modifications include base modifications, sugar modifications, and backbone modifications.

It is to be understood that the nucleic acids used in retroviruses and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The modification may render the nucleic acid more stable and/or less susceptible to degradation under certain conditions. For example, in some instances, the nucleic acids are nuclease-resistant. Methods for synthesizing nucleic acids, including automated nucleic acid synthesis, are also known in the art.

The nucleic acids may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7 deazaguanine, 7 deaza 7 substituted guanine (such as 7 deaza 7 (C2 C6)alkynylguanine), 7 deaza 8 substituted guanine, hypoxanthine, N2-substituted guanines (e.g. N2-methyl-guanine), 5-amino-3-methyl-3H,6H-thiazolo[4,5-d]pyrimidine-2,7-dione, 2,6 diaminopurine, 2 aminopurine, purine, indole, adenine, substituted adenines (e.g. N6-methyl-adenine, 8-oxo-adenine) 8 substituted guanine (e.g. 8 hydroxyguanine and 8 bromoguanine), and 6 thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Amino Acid Substitutions

In some embodiments, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

EXAMPLES

Example 1. Generation of Retrovirus that Targets Antigen-Specific T Cells

Figure 2:
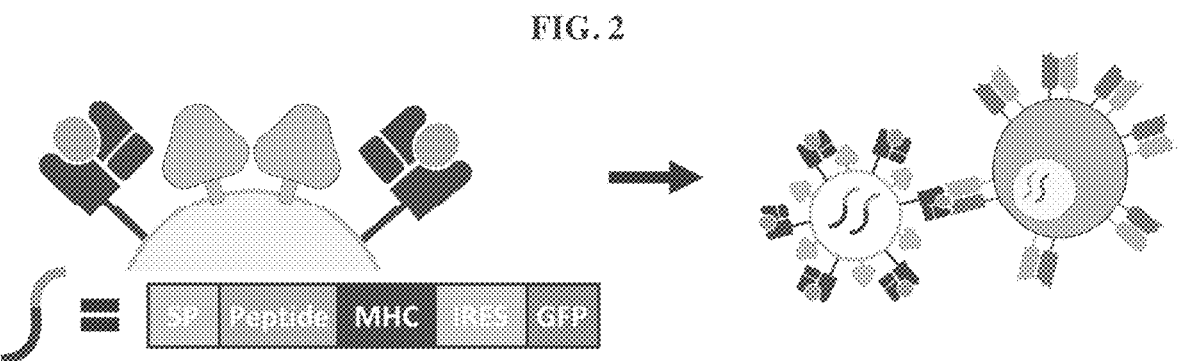
FIG. 2 depicts an exemplary schematic of a protein comprising a signal sequence (SP), an extracellular targeting domain (peptide), a membrane-bound domain (MHC), an internal ribosome entry site (IRES), and a reporter (GFP); and the ability of a retrovirus comprising said protein to interact with a target cell.

Targeted lentiviruses were generated by polyethylenimine (PEI) transfection of HEK293T cells with the following plasmids: an envelope plasmid encoding a mutated VSV-G envelope protein comprising K47Q and R354A mutations, at least one helper plasmid (pRRE, pRev, or psPAX2.1), and a transfer plasmid (FIG. 1). The transfer plasmids used encoded a nucleic acid comprising a structure: S-ETD-MBD-IRES-R, wherein S encoded a B2M signal sequence (as provided by SEQ ID NO: 2), ETD encoded a variable extracellular targeting domain (e.g., the cancer-testis antigen NYESO-1); MBD encoded a membrane bound domain (e.g., MHC HLA-A2 domain), IRES encoded an internal ribosome entry site derived from encephalomyocarditis virus (EMCV), and R encoded a green fluorescent protein GFP reporter (FIG. 2).

The resulting viruses were harvested and purified by standard centrifugation techniques, prior to mixing (using pipette mixing) with T cell lines (e.g. Jurkat T cells) expressing T cell receptors (TCRs) specific to known pMHCs in the presence of hexadimethrine bromide.

Figure 3A:
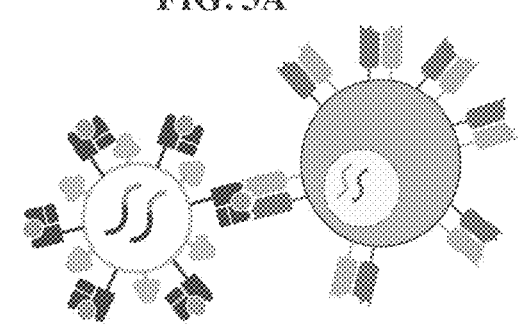
FIGS. 3A-3B depict graphs showing retroviral entry into a target cell.
Figure 3A:
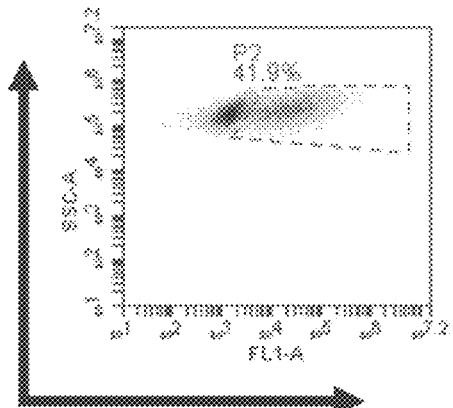
Figure 3B:
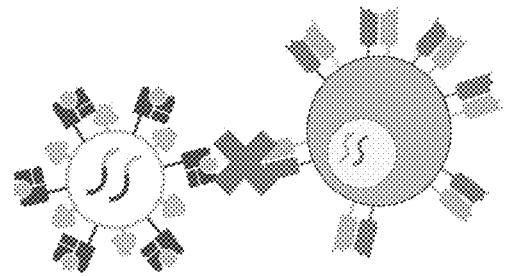
Figure 3B:
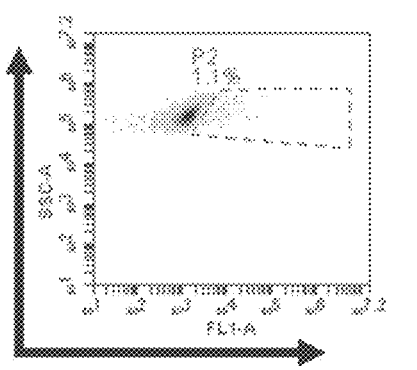

Mixing HLA-A2-NYESO-1 pMHC-displaying viruses with Jurkat T cells expressing an IG4 T cell receptor (TCR) variant (SEQ ID NO: 27) that recognizes the displayed NYESO-1 with a binding affinity of ~26 μM, efficient infection was observed, with 41.9% of T cells expressing the GFP reporter after mixing (FIG. 3A). This result indicated that 41.9% of T cells in this cell population were infected by the virus. Conversely, mixing HLA-A2-NYESO-1 pMHC-displaying viruses were mixed with cells that did not express an IG4 TCR, minimal infection was observed, with only 1.1% of T cells expressing the GFP reporter after mixing (FIG. 3B).

Figure 4:
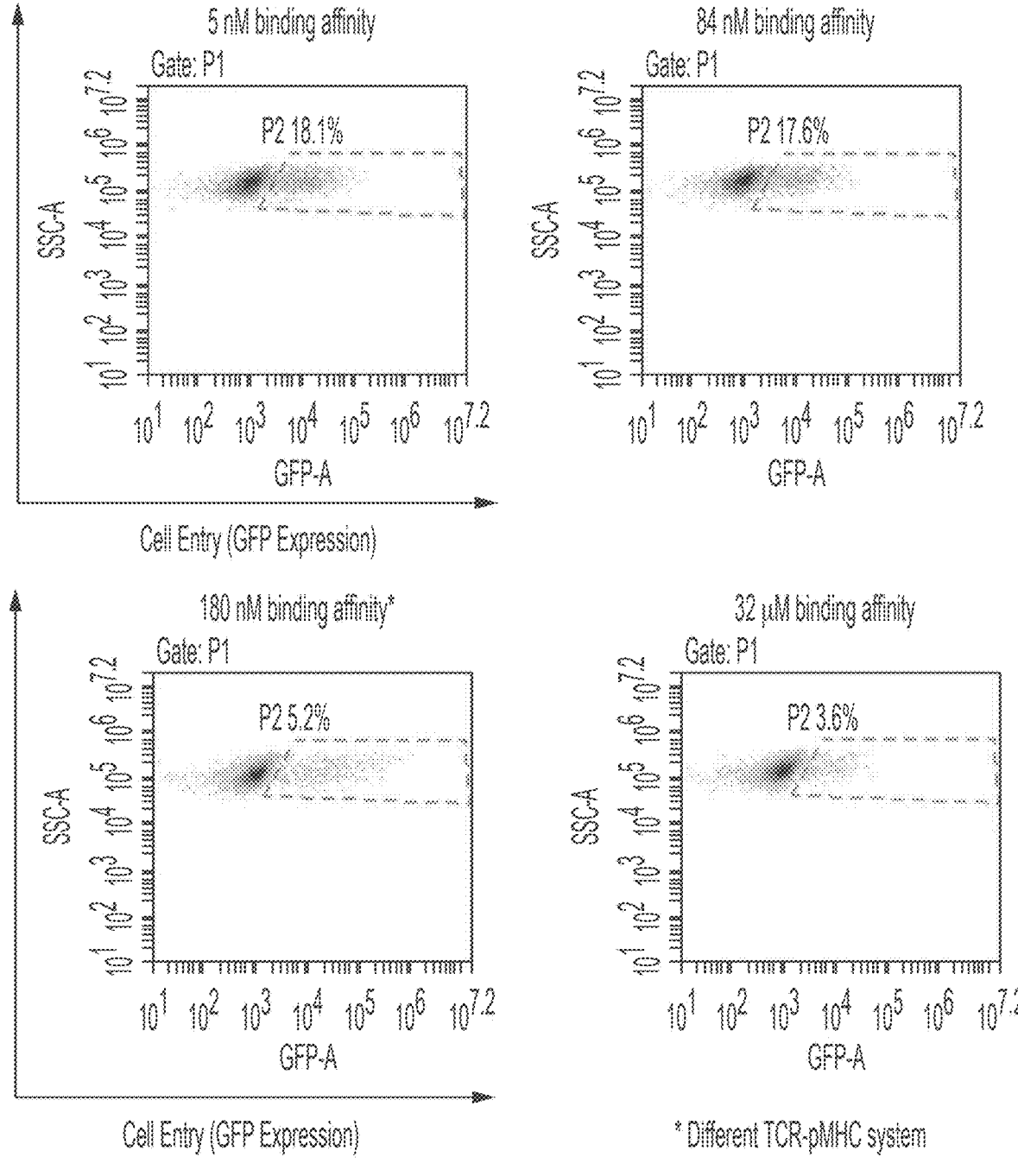
FIG. 4 depicts graphs showing the ability of retroviral entry into target cells at variable affinities between an extracellular targeting domain and its cognate ligand.
Figure 5A:
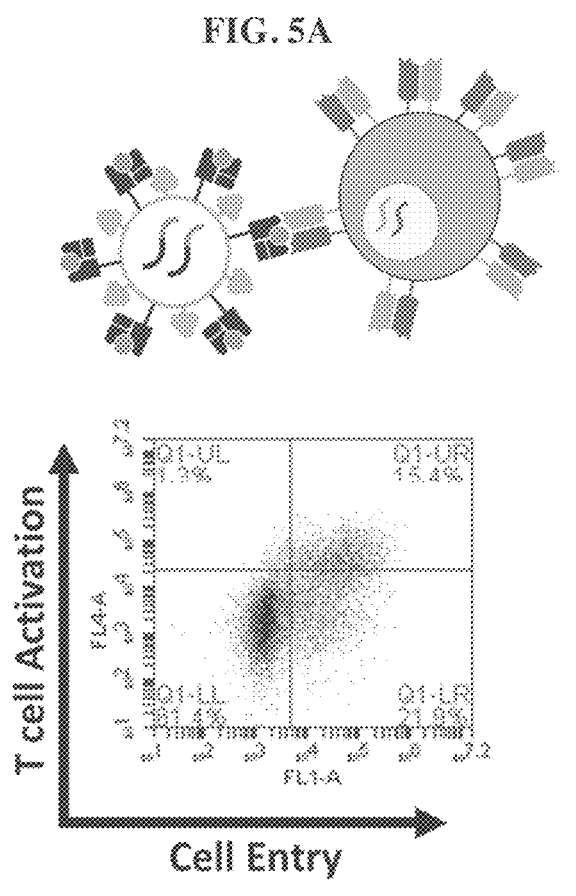
Figure 5B:
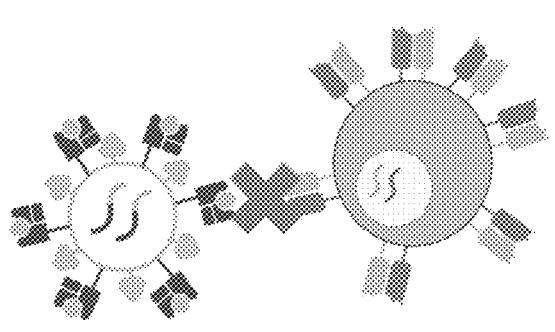
Figure 5B:
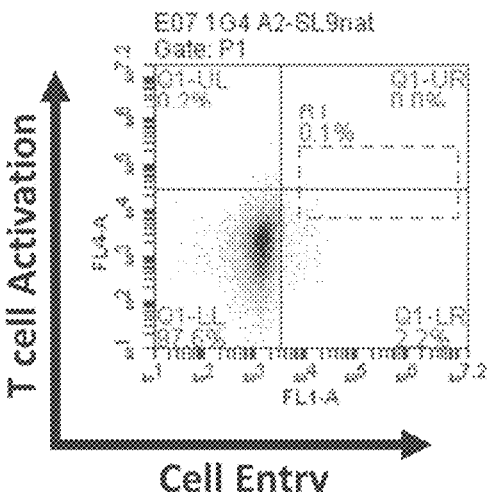
Figure 6:
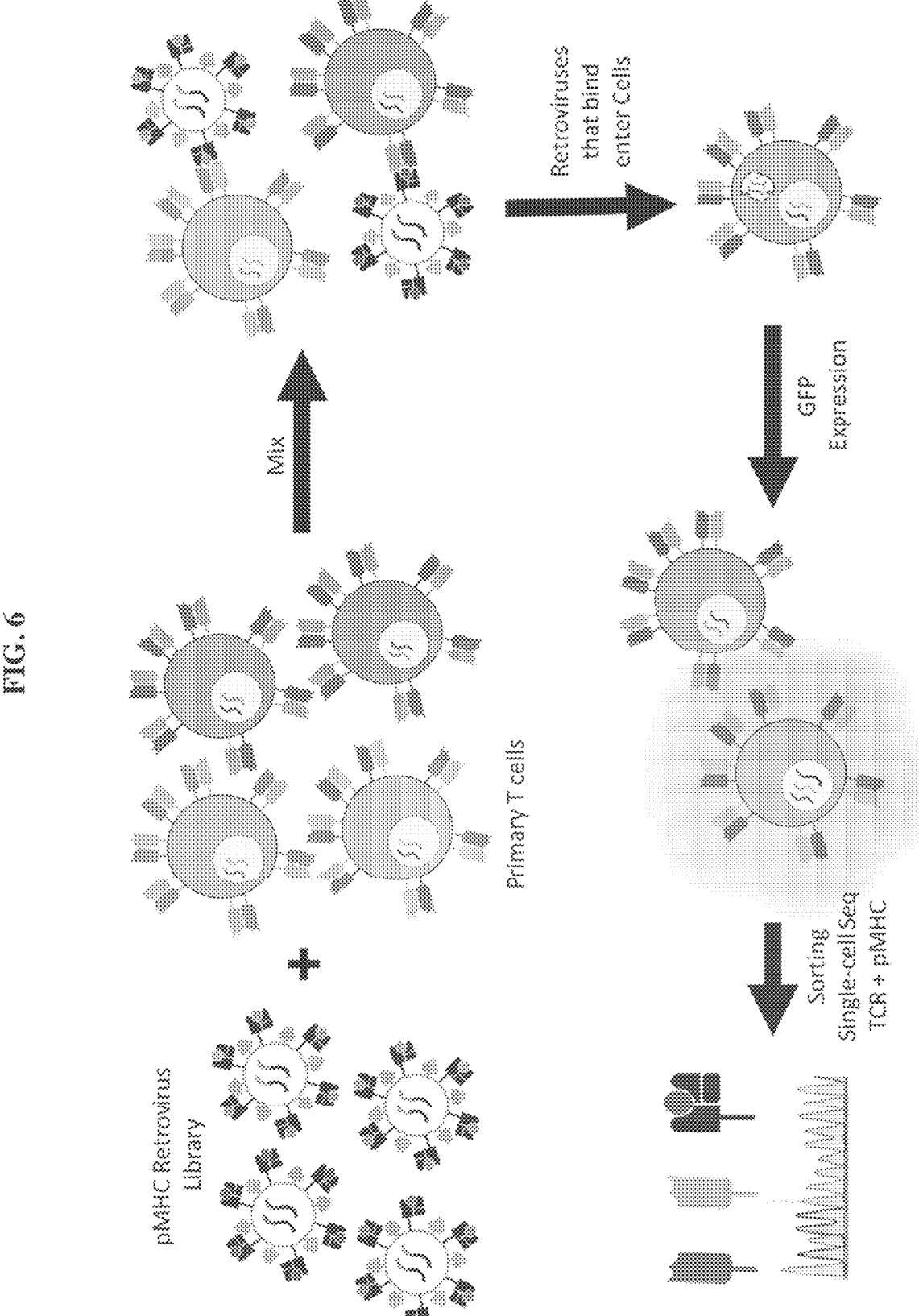
FIG. 6 depicts an exemplary schematic of a pMHC retroviral library screening methodology.

Mixing HLA-A2-NYESO-1 pMHC-displaying viruses with T cells expressing different versions of the IG4 TCR (wherein the different versions of the IG4 TCR exhibit reduced binding to the NYESO-1 antigen, compared to IG4 TCR variant comprising SEQ ID NO: 27) demonstrated that the viruses were able to infect T cells even when the binding affinity between the NYESO-1 antigen and IG4 TCR was down to 32 μM (FIG. 4). A 32 μM binding affinity between NYESO-1 antigen and an IG4 TCR variant (SEQ ID NO: 24) provided 3.6% transduction; a 84 nM binding affinity between NYESO-1 antigen and a IG4 TCR variant (SEQ ID NO: 25) provided 17.6% transduction; and a 5 nM binding affinity between NYESO-1 antigen and a IG4 TCR variant (SEQ ID NO: 26) provided 18.1% transduction; when measuring for GFP expression. 1G4-expressing T cells exhibited T cell activation when transduced/infected with HLA-A2-NYESO-1-displaying viruses, as evidenced by upregulation of CD69 (FIG. 5A). Conversely, HLA-A2-SL9-displaying viruses did not transduce/infect nor activate 1G4-expressing T cells (FIG. 5B).

Example 2. Generation of Retroviruses that Target IL-13 Receptor

Figure 7A:
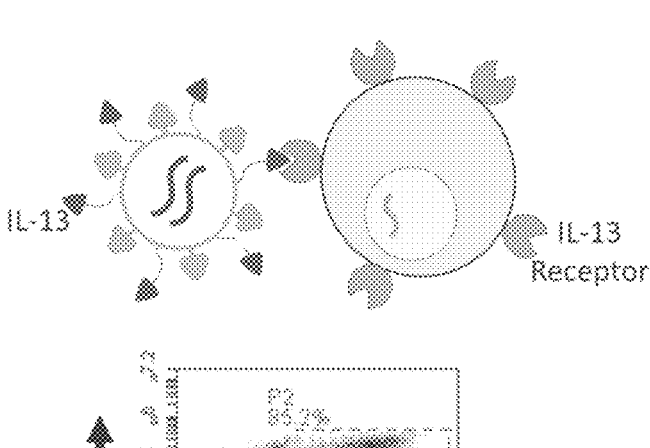
FIGS. 7A-7B depict graphs showing retroviral entry into a target cell.
Figure 7A:
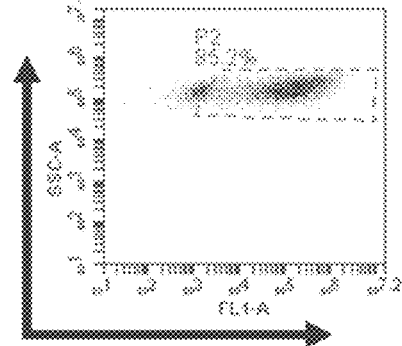
Figure 7B:
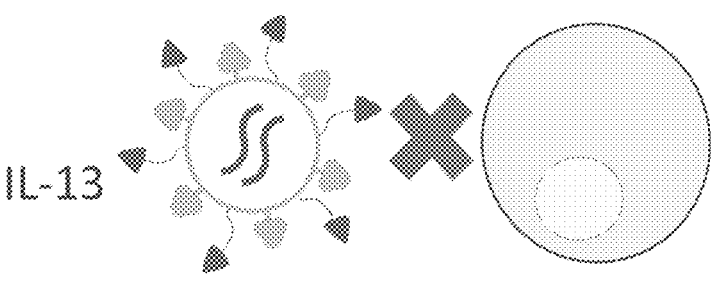
Figure 7B:
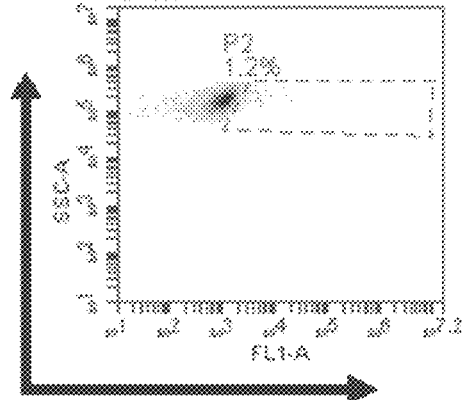

A lentivirus comprising an interleukin-13 (IL-13) extracellular targeting domain was generated, as described in Example 1. The IL-13 extracellular targeting domain consisted of full-length IL-13 protein connected to an IgG4 hinge linker protein linker and a PDGFR transmembrane domain comprising a truncated cytoplasmic tail (PDGFR transmembrane domain: VVVISAILALVVLTIISLIIL-IMLWQKKPR (SEQ ID NO: 28)). When the resultant viruses were mixed with Jurkat cells expressing the IL-13Rα1 receptor, efficient transduction was observed, with 85.2% of the cells expressing the GFP reporter after mixing (FIG. 7A). When the same viruses were mixed with cells not expressing any IL-13 receptors, minimal infection was observed (FIG. 7B).

Figure 12:
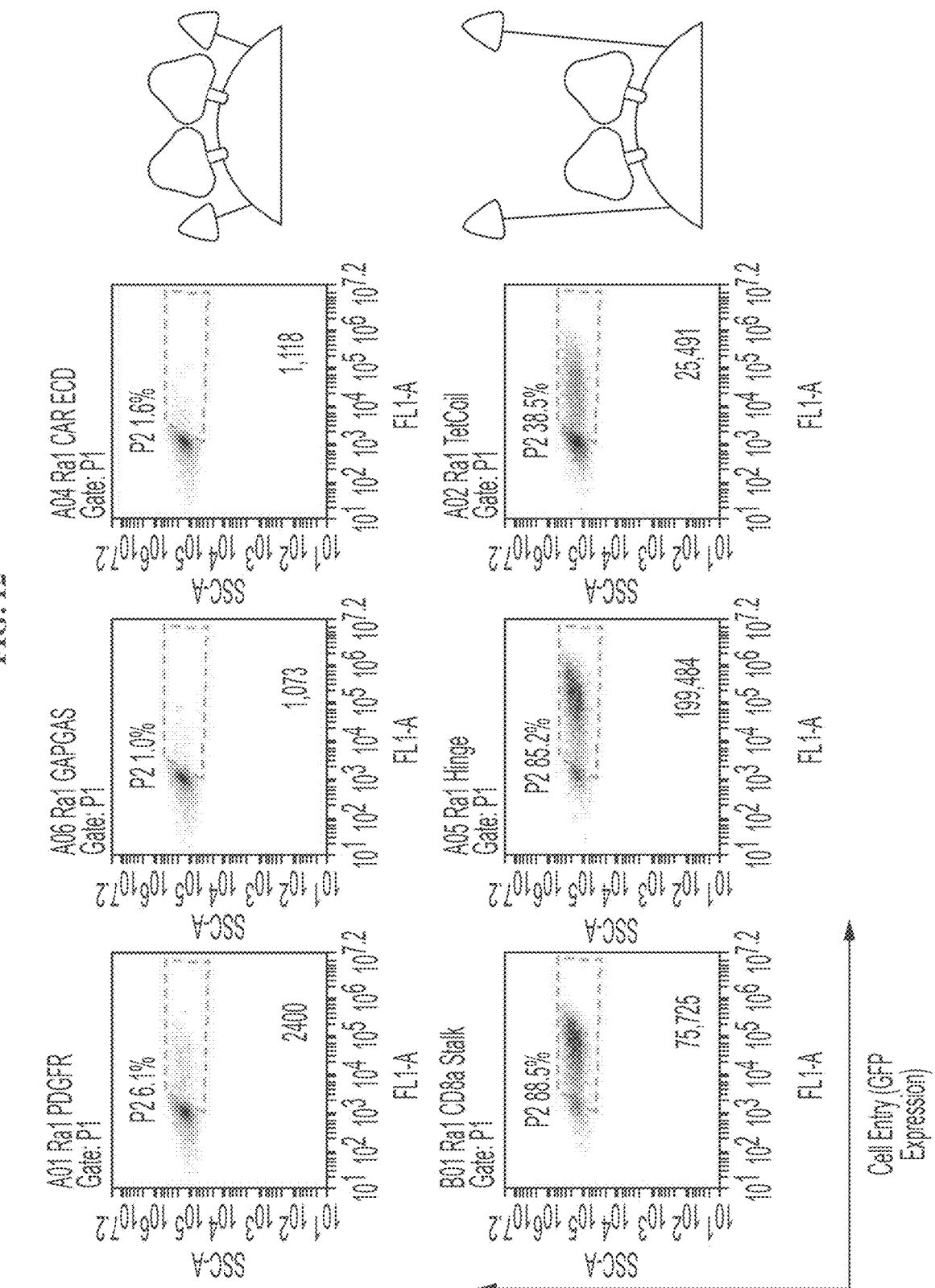
FIG. 12 depicts graphs showing the effect of short protein linkers (PDGFR; GAPGAS (SEQ ID NO: 5); CAR ECD; top, left to right) and long protein linkers (CD8α; Hinge domain; tetrameric coiled coil; bottom, left to right) on retroviral entry.

Additional IL-13 expressing lentiviruses were generated with alternative protein linkers to connect the IL-13 extracellular targeting domain to the PDGFR transmembrane domain. Equivalent volumes of all lentiviruses tested were mixed with Jurkat cells bearing the IL13Rα1 receptor and transduction rates were assessed by GFP reporter (FIG. 12).

Short and long protein linkers were tested for their abilities to allow for cell-to-cell interactions between the extracellular targeting domain (IL-13) and the cognate ligand (IL13Rα1 receptor. Lentiviruses comprising short linkers were marginally able to infect Jurkat cells, with PDGFR linker (AVGQDTQEVIVVPHSLPFK (SEQ ID NO: 3)) enabling infection of 6.1% of cells; GAPGAS linker (GAPGAS (SEQ ID NO: 5)) enabling infection of 1.0% of cells; and a CAR ECD linker (ASESKYGPPCPPCP (SEQ ID NO: 10)) enabling infection of 1.6% of cells. Lentiviruses comprising long linkers were highly successful at infecting Jurkat cells, with CD8α stalk linker (ASAKPTTT-PAPRPPTPAPTIASQPLSLRPEAARPAAGGAVHTR-GLDFAK (SEQ ID NO: 4)) enabling infection of 88.5% of cells; IgG4 hinge linker (ASESKY-GPPCPPCPAVGQDTQEVIVVPHSLPFK (SEQ ID NO: 8)) enabling infection of 85.2% of cells; and an oligomerized linker comprising an amino acid sequence that can form a tetrameric coiled coil (e.g., ASGGGGSGELAAIKQELAAI-KKELAAIKWELAAIKQGAG (SEQ ID NO: 9)) enabling infection of 38.5% of cells.

Example 3. Generation of Retroviruses that Target CD19

Figures 8, 9:
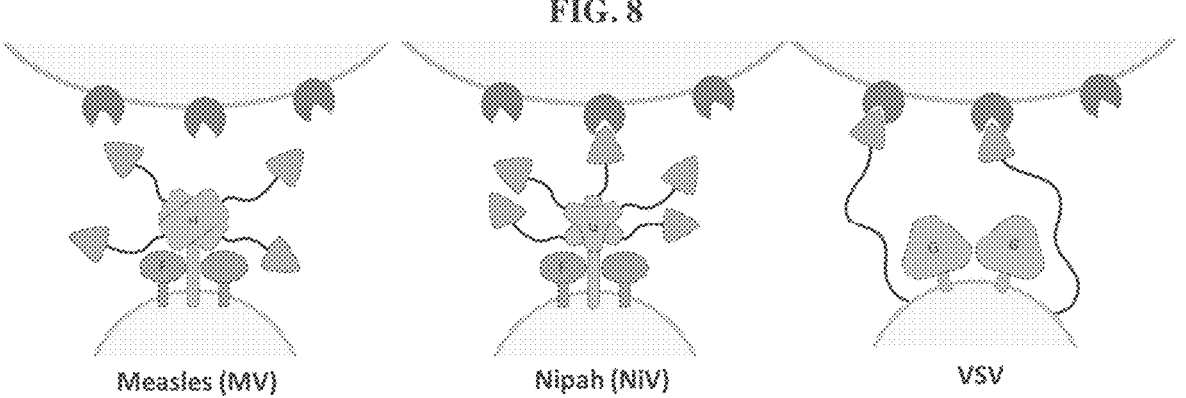
FIG. 8 depicts three exemplary retroviruses, each com-prising a different viral envelope protein.
FIG. 9 depicts the ability of a retrovirus comprising a Nipah viral envelope protein and an anti-CD19 scFv antibody to infect and enter CD19+ Raji cells.

A lentivirus pseudotyped with a Nipah virus F protein and a Nipah virus G protein fused to an anti-CD19 scFv was able to transduce CD19$^+$ Raji B cells (cells that express CD19), with 14.5% of cells expressing the GFP reporter after mixing (FIG. 9).

Figure 10A:
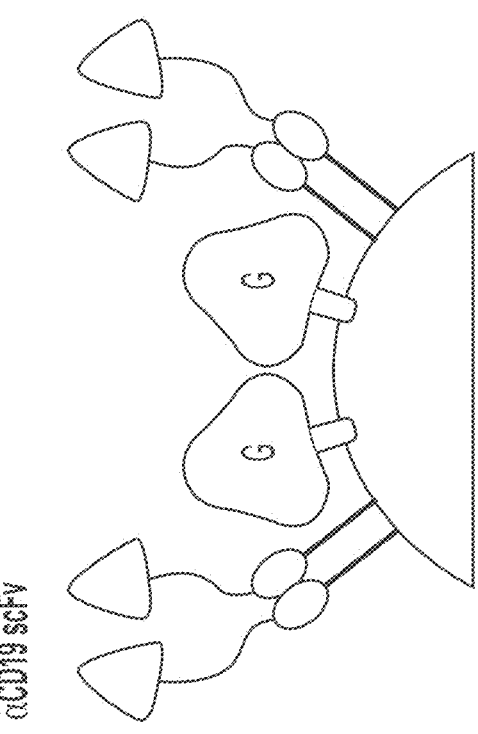
FIGS. 10A-10B depict the ability of a retrovirus comprising a mutated VSV-G viral envelope protein and an anti-CD19 scFv antibody to infect and enter CD19+ Raji cells, while not infecting CD19− Jurkat cells. A retrovirus comprising a wild-type VSV-G viral envelope protein and an anti-CD19 scFv antibody infects both CD19+ Raji cells and CD19− Jurkat cells.
Figure 10B:
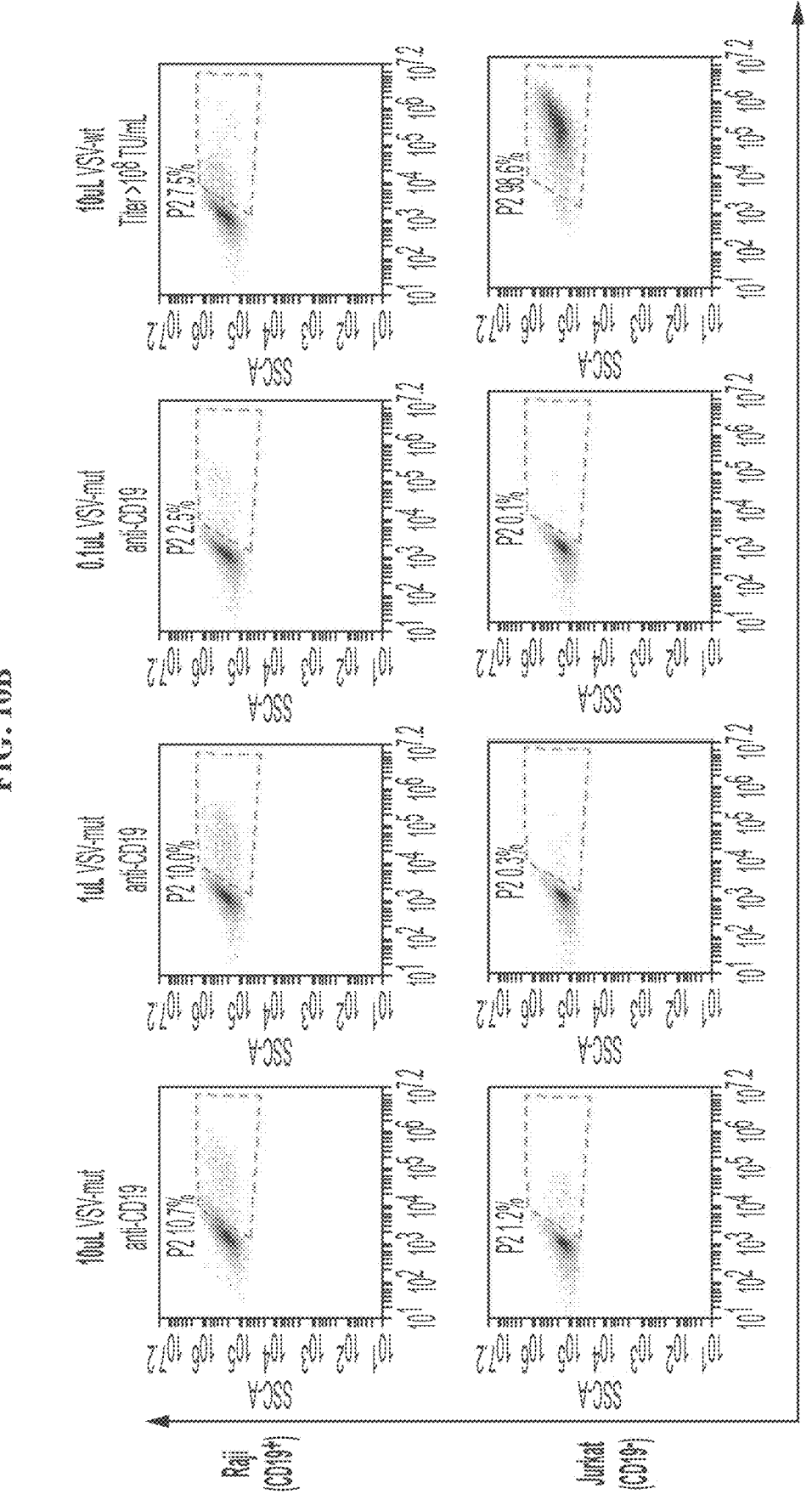
Figure 11:
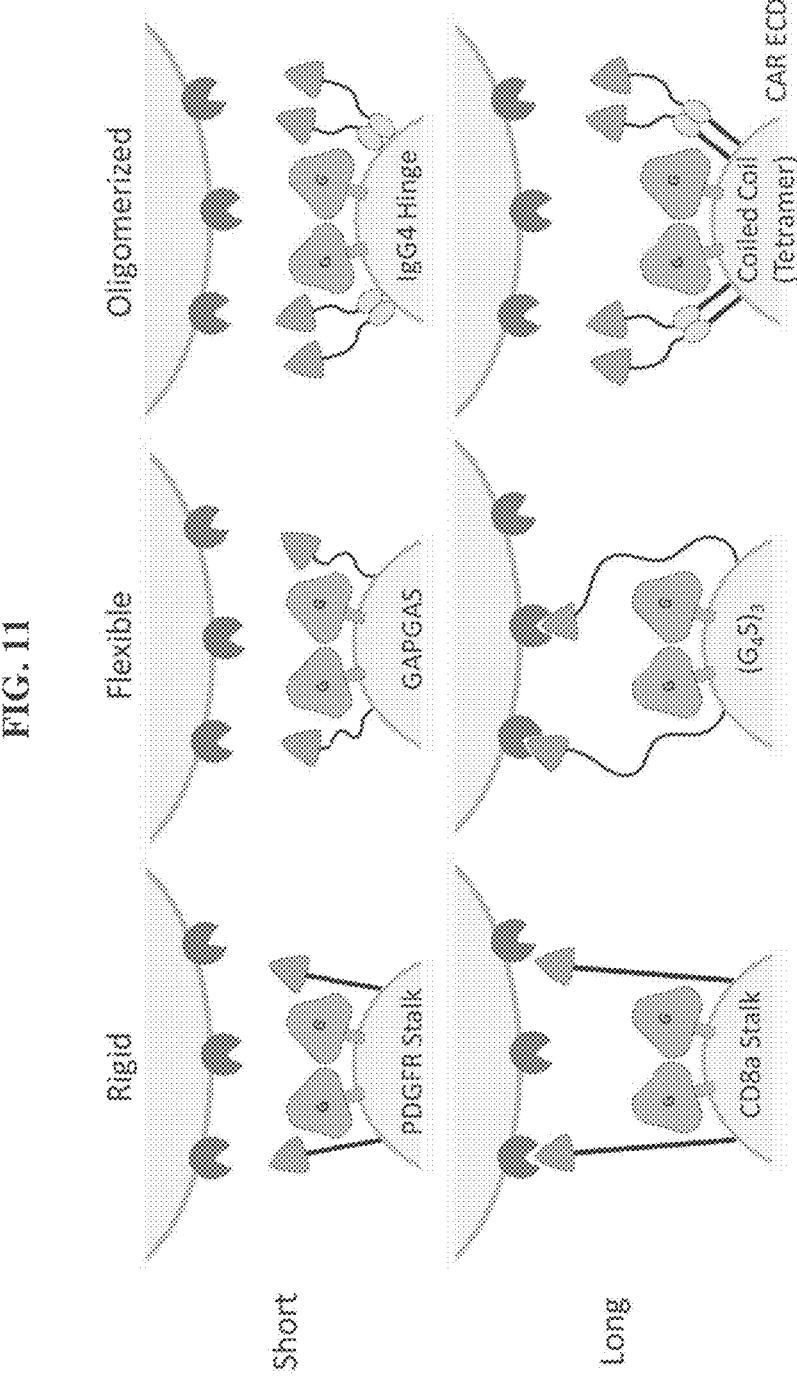
FIG. 11 depicts exemplary linkers for use in nucleic acids and proteins comprising membrane-bound and extracellular targeting domains.

A lentivirus pseudotyped with VSV-mut (mutated VSV-G) and an anti-CD19 scFv fused to an IgG hinge domain, a truncated PDGFR stalk, and PDGFR transmembrane domain was able to transduce CD19$^+$ Raji B cells. Application of 1 μL of VSV-mut lentivirus (200× concentrated) to the CD19$^+$ Raji B cells provided 10.0% infected cells (based on expression of GFP reporter); 10 μL VSV-mut provided 10.7% infected cells. (FIG. 10). The same VSV-mut lentivirus construct did not transduce/infect CD19$^-$ Jurkat cells (cells that do not express CD19), demonstrating that the lentivirus is specific for cells expressing the cognate ligand of its extracellular targeting domain (anti-CD19 scFv).

A lentivirus pseudotyped with VSV-wt (wild-type VSV-G) and an anti-CD19 scFv fused to an IgG hinge domain, a truncated PDGFR stalk, and PDGFR transmembrane domain was able to transduce CD19$^+$ Raji B cells and CD19$^-$ Jurkat cells. This comparative result demonstrates the lentivirus comprising a mutated VSV-G (wherein the mutations diminish the native function of VSV-G protein) is selective for transducing/infecting cells that express a cognate ligand targeted by the extracellular targeting domain of the lentivirus.

Example 4. Ability of Targeted Lentiviruses to Induce T Cell Signaling

Figure 13:
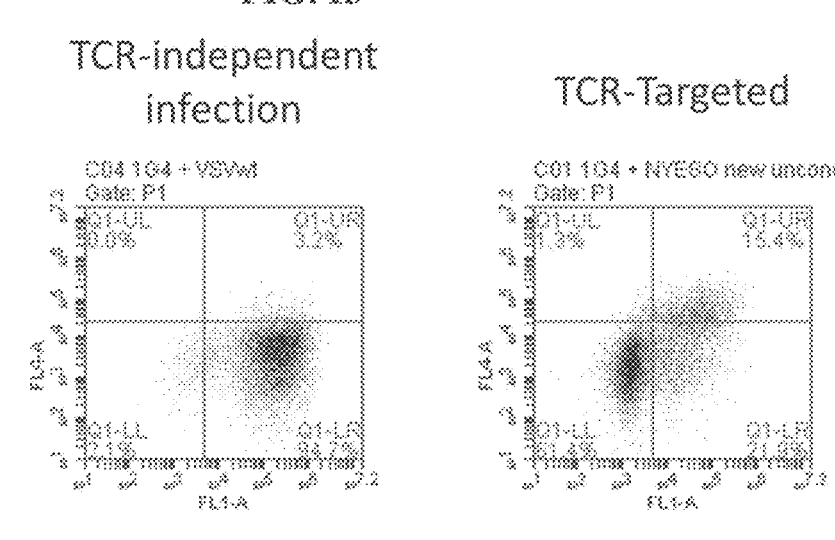
FIG. 13 depicts graphs showing that retroviruses comprising mutated VSV-G viral envelope proteins activate T cell signaling (right panel) and that retroviruses comprising wild-type VSV-G viral envelope proteins do not activate T cell signaling (left panel), as determined by expression of CD69.
Figure 14:
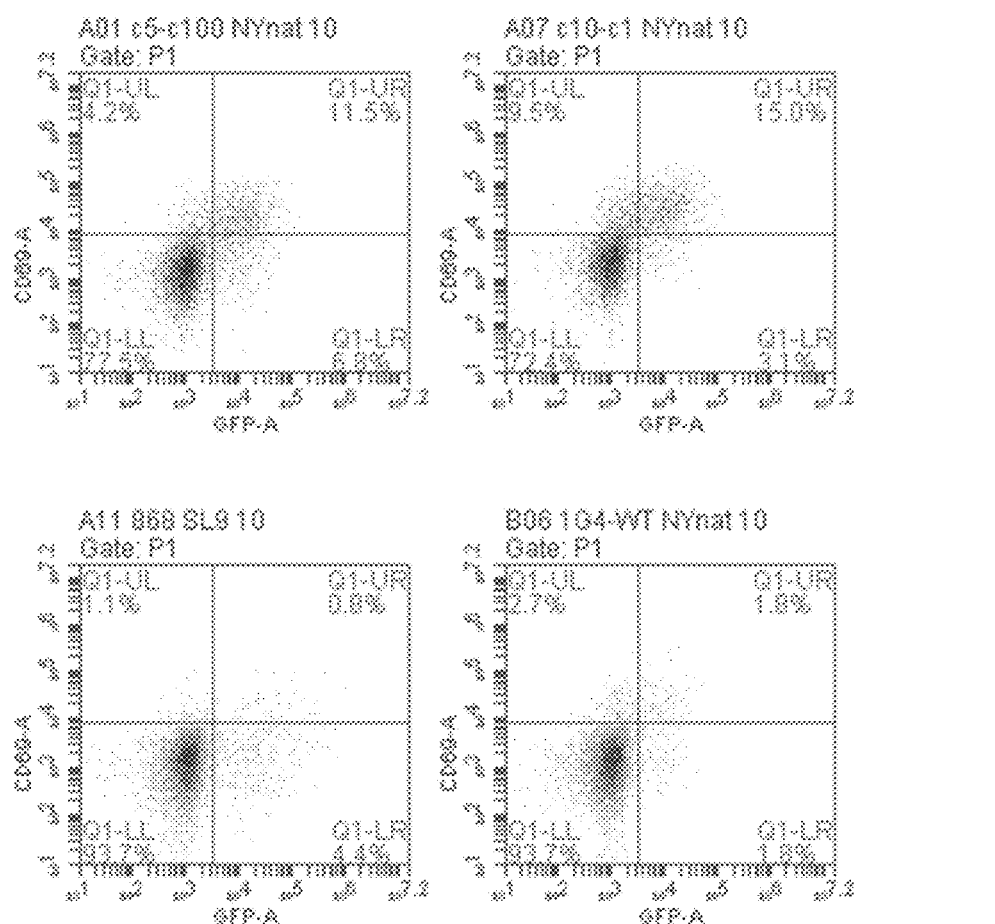
FIG. 14 depicts graphs showing that retroviruses having variable affinities between their extracellular targeting domains and a T cell cognate ligand are able to activate T cell signaling.

Viruses were assessed to determine whether infection via TCR targeting resulted in evidence of TCR signaling. While non-targeted VSV-wt viruses efficiently infected T cells, they did not activate T cells, as assessed by CD69 expression levels, compared to controls (FIG. 13, left panel). However, when HLA-A2-NYESO-1 displaying viruses were used to target Jurkat T cells expressing the high-affinity wild-type 1G4 TCR, upregulation of CD69 was observed in transduced cells, indicating TCR signaling occurred during infection (FIG. 13, right panel). These results were replicated when mixing HLA-A2-NYESO-1 displaying viruses with T cells expressing the lower-affinity mutant 1G4 TCR constructs described in Example 1 (FIG. 14)

Figure 15:
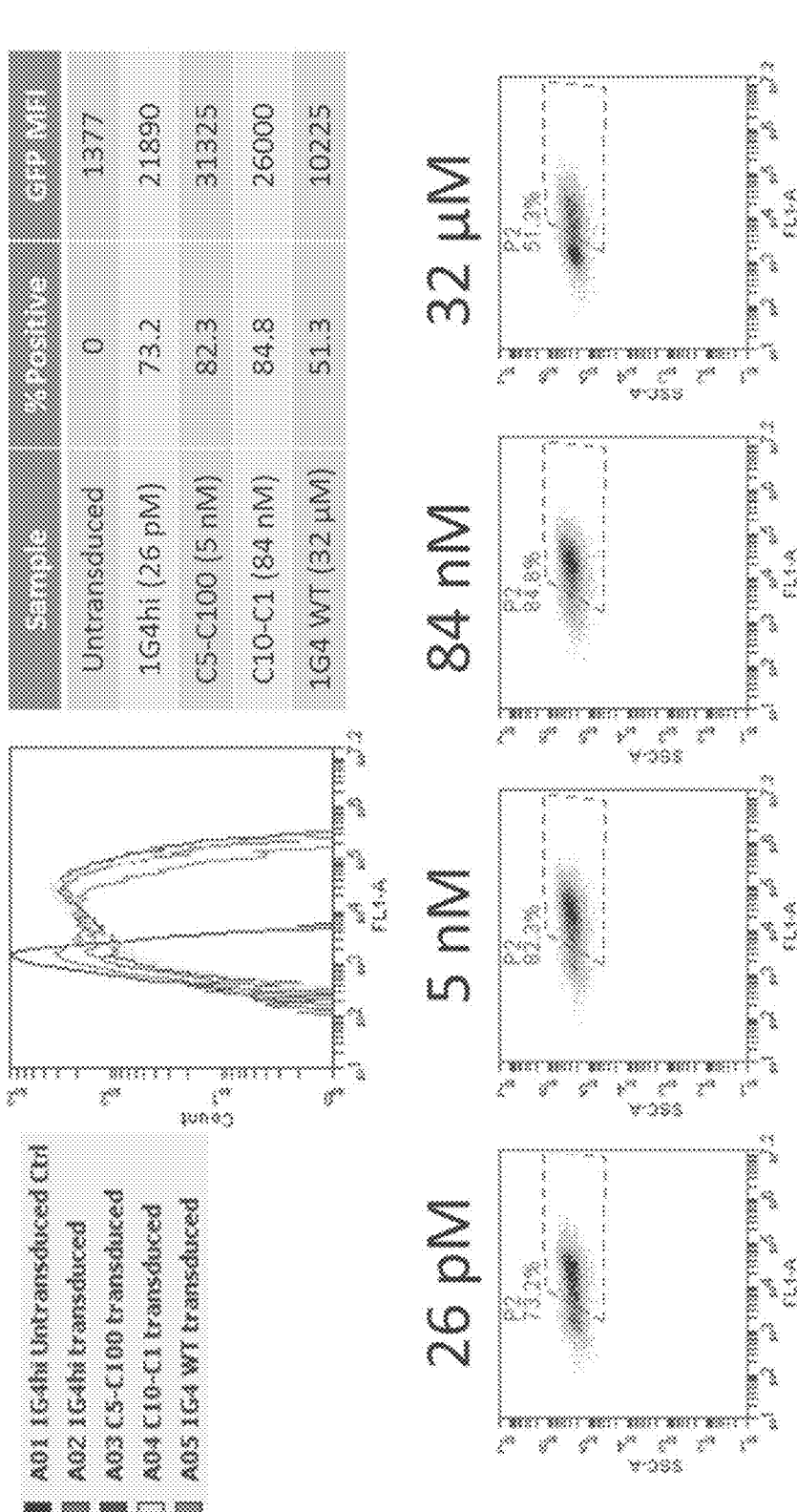
FIG. 15 depicts graphs showing the ability of retroviral entry into target cells at variable affinities, from picomolar to micromolar binding affinities, between an extracellular targeting domain and its cognate ligand.

Example 5. Lentiviral Transduction Through the TCR at Physiological Affinities A population of Jurkat T cells was purified on the basis of expression of IG4 TCR before being contacted with HLA-A2-NYESO-1 displaying viruses. The viruses efficiently transduced the purified populations of Jurkat T cells expressing each of the affinity variants of the 1G4 TCR, based on expression of the GFP reporter (FIG. 15). A 32 μM binding affinity between NYESO-1 antigen and an IG4 TCR variant provided 51.3% transduction; a 84 nM binding affinity between NYESO-1 antigen and an IG4 TCR variant provided 84.8% transduction; a 5 nM binding affinity between NYESO-1 antigen and an IG4 TCR variant provided 82.3% transduction; and a 26 nM binding affinity between NYESO-1 antigen and an IG4 TCR variant provided 73.2% transduction.

Figure 16A:
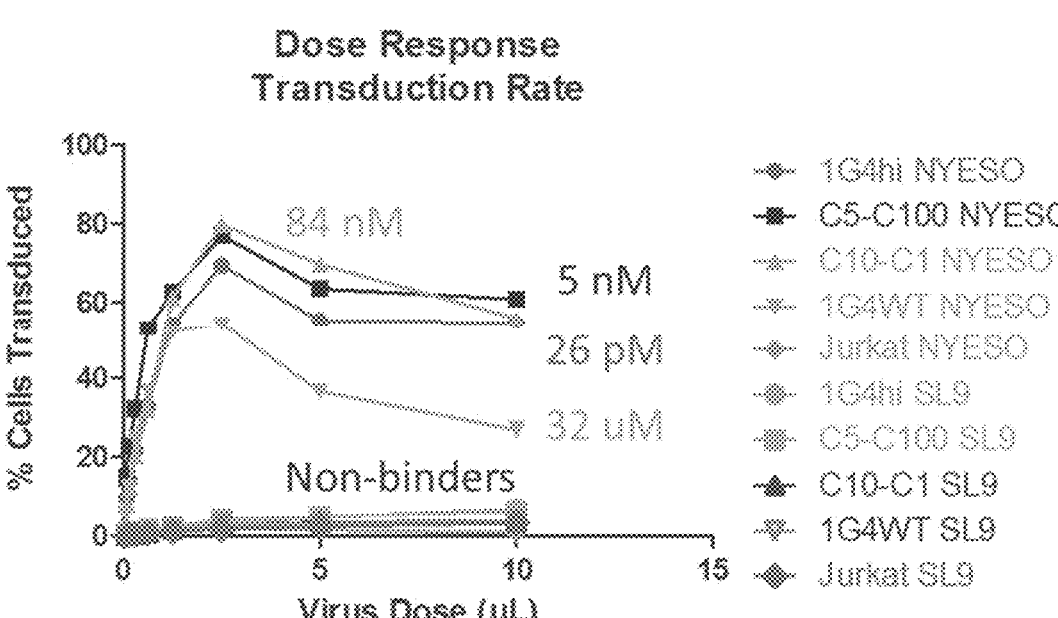
FIGS. 16A-16B depict graphs demonstrating the ability of retroviral entry into target cells at varying concentrations of virus.
Figure 16B:
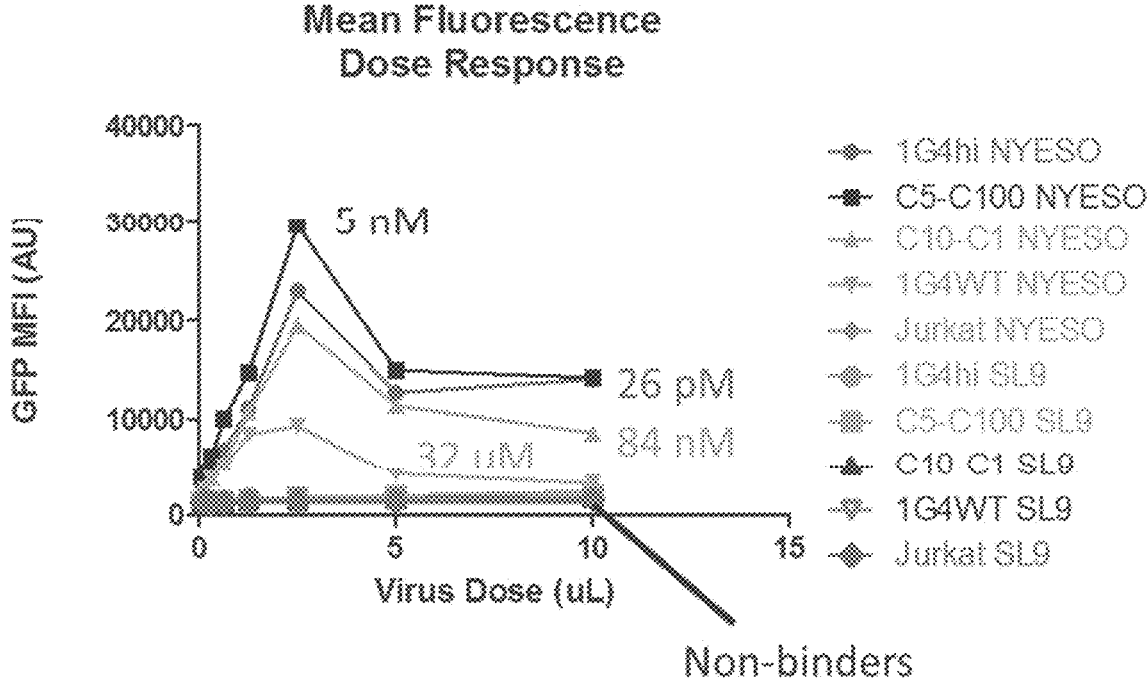

The differences among different IG4 TCR affinity variants were further investigated by performing a dose response to incubate varying amounts (0.5-10 μL of virus) of the HLA-A2-NYESO-1 displaying viruses with cells. NYESO-1 displaying lentiviruses transduce IG4-expressing T cells, even at high viral load (FIG. 16A). Conversely, SL-1 displaying lentiviruses (negative controls) do not transduce IG4-expressing T cells (SL-1 and IG4 TCR are not cognate binding partners).

Figure 17:
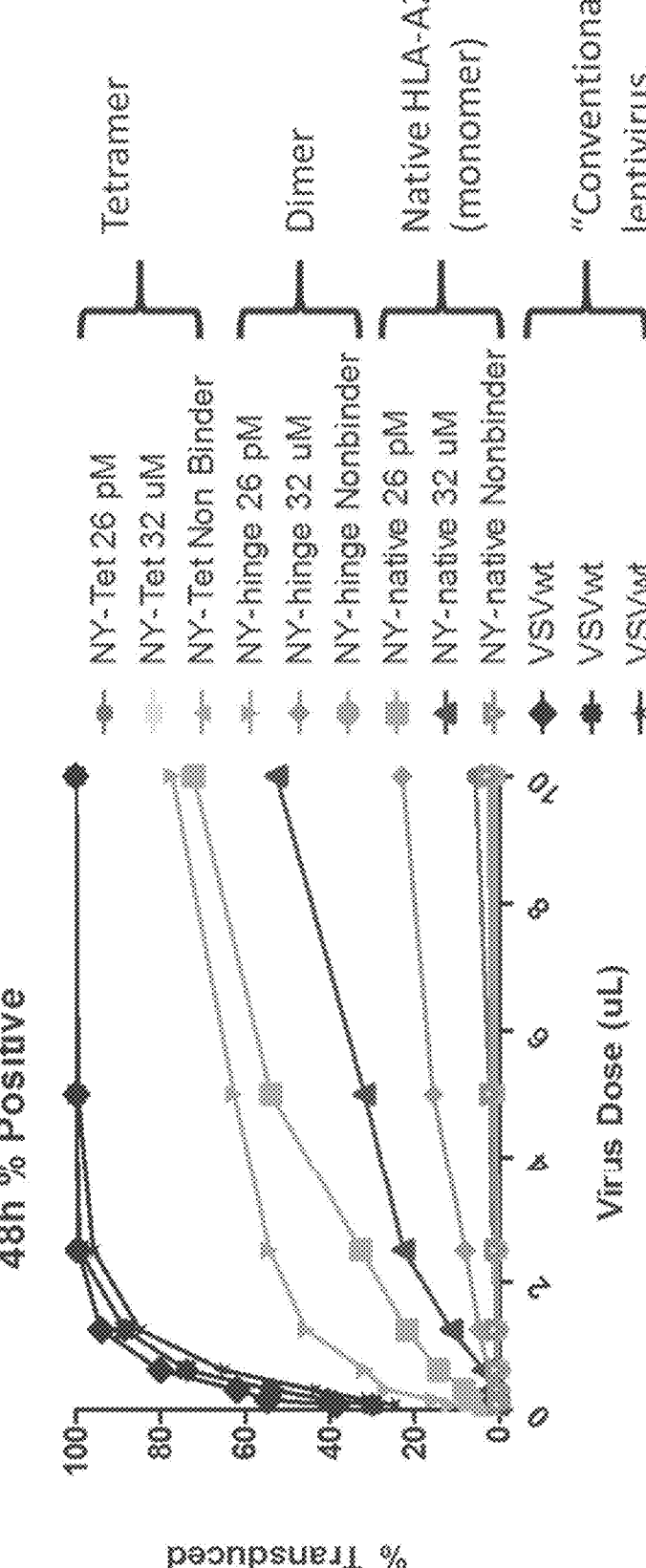
FIG. 17 depicts a graph that demonstrates the impact of protein linker oligomerization on retroviral transduction.

The protein architecture of the membrane-bound NYESO-1 targeting protein was altered to test the ability of oligomerized NYESO-1 displaying constructs to transduce T cells. NYESO-1 displaying expressing lentiviruses were generated with alternative protein linkers to connect the NYESO-1 extracellular targeting domain to transmembrane domain were generated (a protein linker comprising the IgG4 hinge (dimer); and an oligomerized linker comprising an amino acid sequence that can form a tetrameric coiled coil (tetramer)). As demonstrated in FIG. 17, lentiviruses expressing these alternative architectures were able transduce T cells expressing the 26 μM and 32 μM IG4 TCR variants.

Example 6. Virus Binding Assay

Figure 18A:
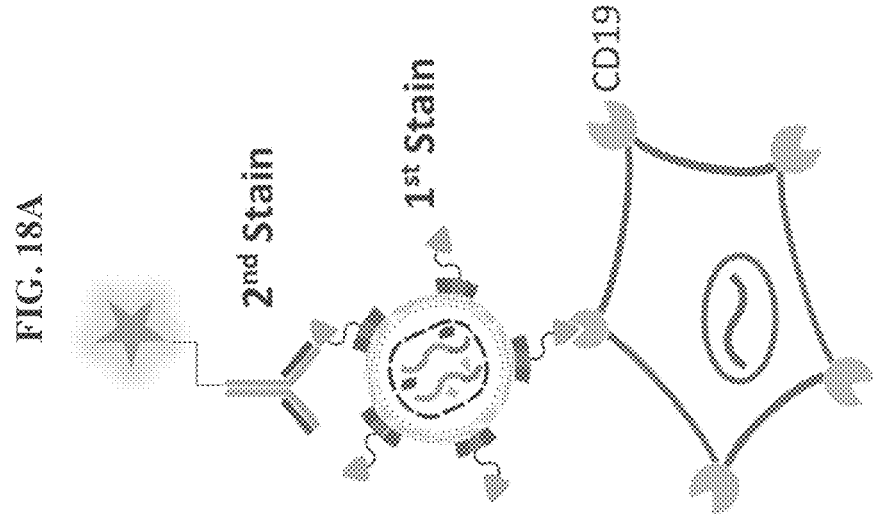
FIGS. 18A-18B depict the ability to detect a binding interaction between a retrovirus comprising an anti-CD19 scFv antibody and a target cell comprising CD19 using a fluorescently labeled antibody that binds to the retrovirus.
Figure 18B:

Viruses were pseudotyped with either (1) wild-type VSV-G (VSV-G); (2) measles virus F protein and receptor-blinded H protein fused to an anti-CD19 scFv and a FLAG tag (MV-αCD19); (3) Nipah virus F protein and receptor-blinded G protein fused to an anti-CD19 scFv and a FLAG tag (NiV-αCD19); or (4) Nipah virus F and receptor-blinded G protein with a FLAG tag but no scFv (NiV-dead). Each of these viruses was mixed with CD19$^+$ Raji B cells and subsequently exposed to a fluorescently-labeled antibody against the FLAG tag. As demonstrated in FIGS. 18A-18B, the viruses that expressed an anti-CD19 scFv (MV-αCD19 and NiV-αCD19) bound to the Raji B cells. The viruses that did not express an anti-CD19 scFv (VSV-G and NiV-dead) did not bind to the Raji B cells.

Example 7. Screening a Library of Retroviruses Against Population of T Cells

A library of retroviruses ($10^7$-$10^{10}$ unique retroviruses) comprising a mutated VSV-G envelope protein, a non-viral membrane-bound protein comprising a MHC membrane-bound domain, a variable IL-13 extracellular targeting domain, and a GFP reporter.

First, a library of nucleic acids encoding unique non-viral membrane-bound proteins comprising a MHC membrane-bound domain and a variable IL-13 extracellular targeting domain, is prepared using PCR primers that include degenerate codons at positions known to interact with IL-13 receptors and and induce random mutagenesis in the IL-13 extracellular targeting domain. The resulting nucleic acid constructs are assembled into viral transfer plasmids with fluorescent reporters by standard molecular cloning techniques. These plasmids ("transfer plasmids"), along with helper plasmids and an envelope plasmid encoding mutated VSV-G envelope protein (or an equivalent pseudotype) are transfected into retroviruses to generate the library of retroviruses. The viruses are purified and mixed with populations of cells (e.g. T cell lines, HEK293 cell lines) that express an IL-13 receptor of interest. The viruses are incubated with the populations of cells at an appropriate temperature (e.g., 37° C.) for an appropriate period of time (e.g., 1-48 hours). Mixing is performed in standard cell culture media with hexadimethrine bromide. After 24-48 hours, the cells are sorted based on the expression of the GFP reporter. High-expressing cells are retained and the sorting process is repeated as needed. After these rounds of selection by sorting, the retained cells are lysed and the cellular RNA and DNA are isolated for analysis using next-generation sequencing methods to determine which IL-13 variants were able to mediate viral entry.

Example 8. Generation of Additional Retroviruses that Targets Antigen-Specific T Cells Additional targeted lentiviruses were generated using the protocols described in Example 1.

Figure 19:
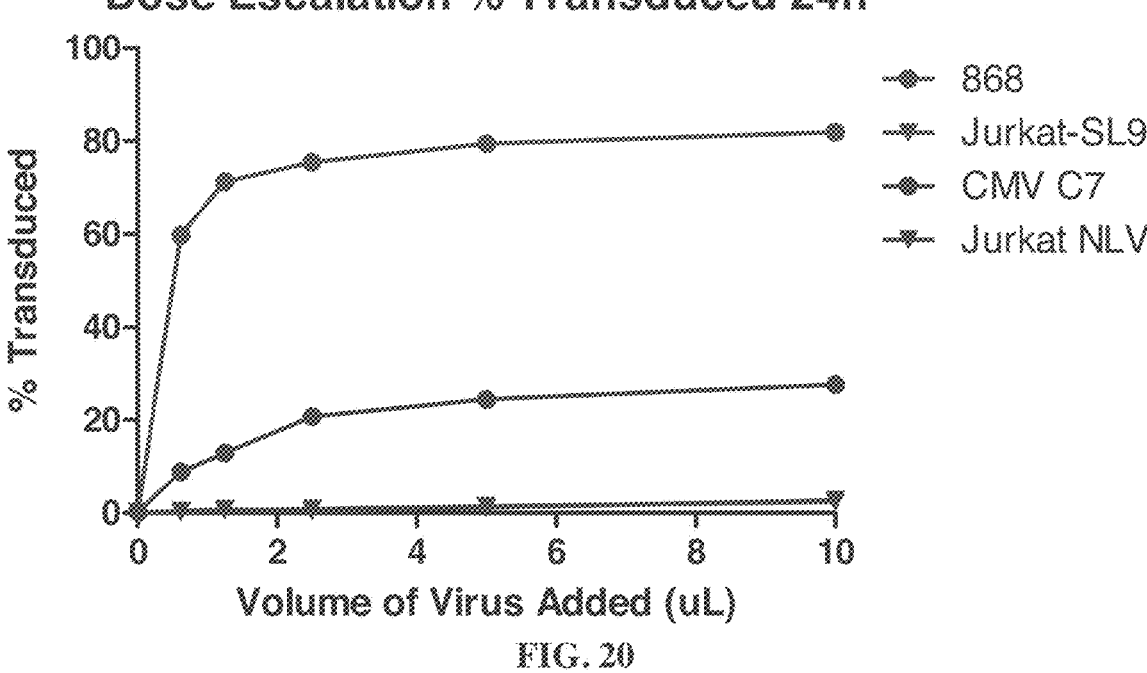
FIG. 19 depicts the ability of SL9 peptide displaying lentiviruses to transduce 868 TCR-expressing T cells ('868') and the ability of CMV NLV peptide displaying lentiviruses to transduce C7 TCR-expressing T cells ('CMV C7').
Figure 20:
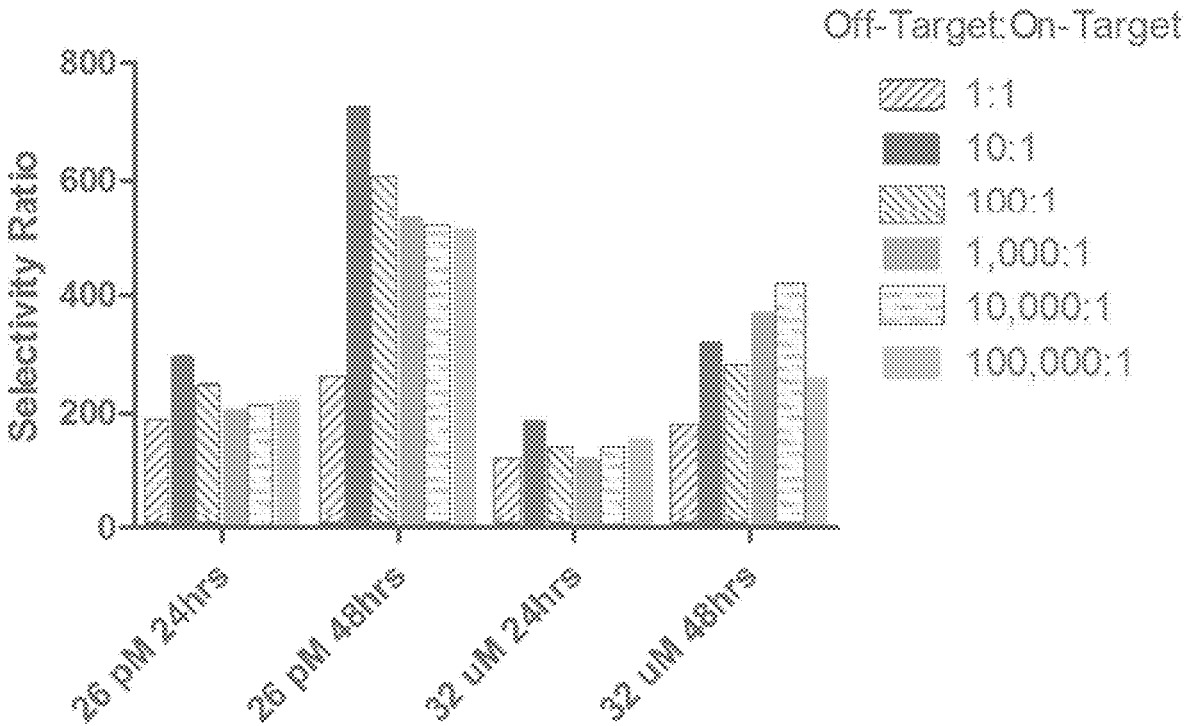
FIG. 20 depicts the ability of NYESO-1 displaying lentiviruses to selectively transduce T cells (target cells) expressing an IG4 T cell receptor (TCR) variant (binding affinities of ~26 μM or ~32 μM for NYESO-1) relative to cells not expressing an IG4 TCR (off-target) at ratios of off-target cells to target cells as high as 100,000:1.

As shown in FIG. 19, mixing (i) lentivirus comprising a mutated VSV-G envelope protein and pMHC displaying a SL9 peptide and (ii) 868 TCR-expressing T cells demonstrated that the viruses were able to transduce and infect T cells even at low amounts of added virus (~70% transduction at 1 μL of virus). Conversely, mixing of these viruses with off-target Jurkat cells led to low levels of transduction (less than 5% up to 10 μL of virus added). A similar experiment As also shown in FIG. 19, mixing (i) lentivirus comprising a mutated VSV-G envelope protein and pMHC displaying a cytomegalovirus (CMV) NLV peptide and (ii) C7 TCR-expressing T cells demonstrated that the viruses were able to transduce and infect T cells (~25% transduction at 10 μL of virus). Conversely, mixing of these viruses with off-target Jurkat cells led to low levels of transduction (less than 5% up to 10 μL of virus added).

Example 9. Generation of Retroviruses Comprising Targeted pMHCs Stabilized by Disulfides Additional targeted lentiviruses were generated using the protocols described in Example 1. These additional lentiviruses further comprised a disulfide situated within the pMHC in order to stabilize the structure of the pMHC.

Figure 21:
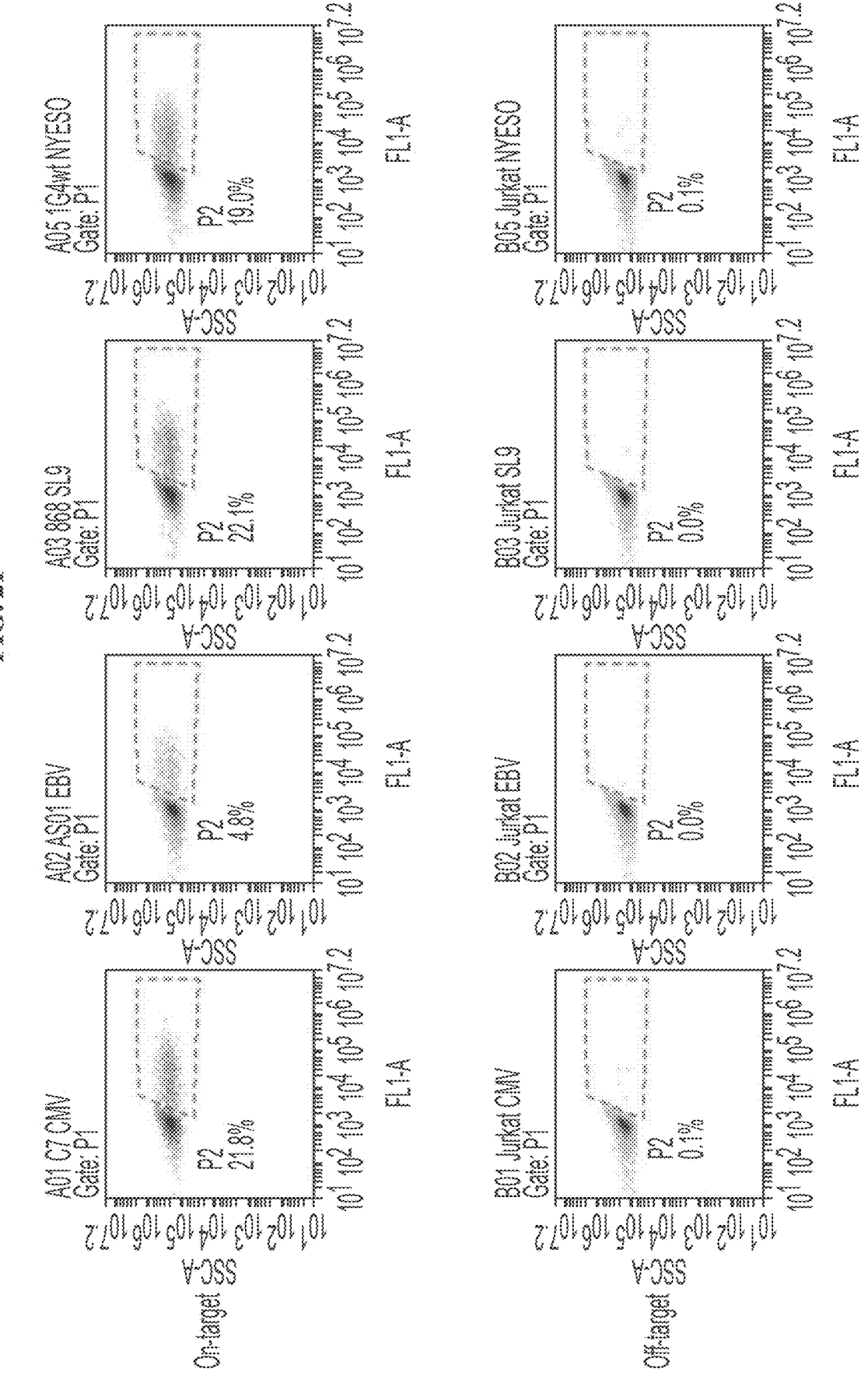
FIG. 21 depicts the ability of lentiviruses displaying varying targeting peptides (CMV NLV; EBV; SL9; GL9; NYESO-1) to selectively transduce T cells that express targeting peptide-specific TCRs (on-target) relative to T cells that do not express the targeting peptide-specific TCRs (off-target).

As shown in FIG. 21, mixing (i) lentivirus comprising a mutated VSV-G envelope protein and a disulfide-stabilized pMHC displaying a targeting peptide and (ii) target cells expressing a cognate receptor demonstrated that the targeted viruses were able to transduce and infect target cells. Conversely, mixing of these targeted viruses with off-target cells caused no, or very limited (0.1%) transduction.

Specifically, a lentivirus comprising a disulfide-stabilized CMV NLV pMHC tranduced on-target C7 TCR-expressing T cells at a 21.8% transduction rate; a lentivirus comprising a disulfide-stabilized EBV pMHC tranduced on-target AS01 cells at a 4.8% transduction rate; a lentivirus comprising a disulfide-stabilized SL9 pMHC tranduced on-target 868 TCR-expressing T cells at a 22.1% transduction rate; and a lentivirus comprising a disulfide-stabilized NYESO-1 pMHC tranduced on-target IG4 TCR-expressing T cells at a 19.0% transduction rate.

Example 10. Targeted Viruses Transduce Primary Cells

Figure 22A:
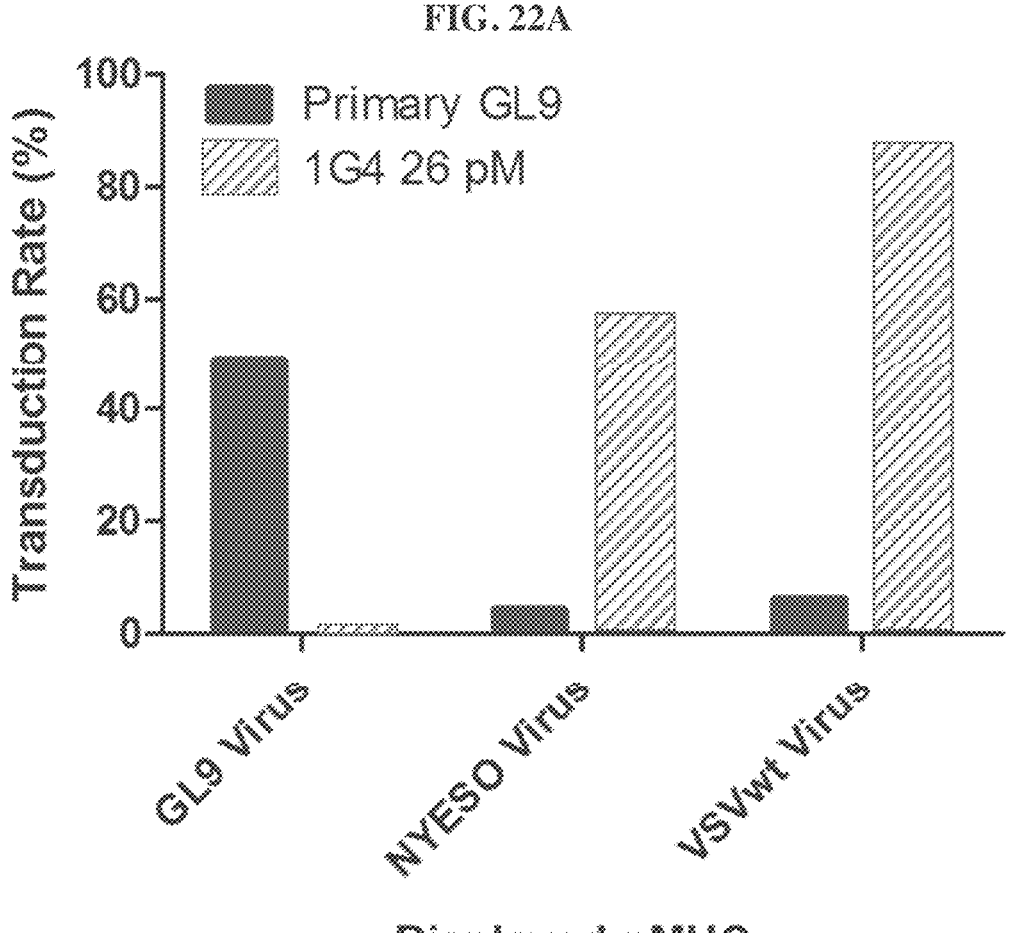
FIGS. 22A-22B depict the ability of varying lentiviruses (GL9 peptide targeting; NYESO-1 peptide targeting; wild-type VSV) to transduce primary T cells that express GL9-specific TCRs and T cells that express an IG4 TCR variant.
Figure 22B:
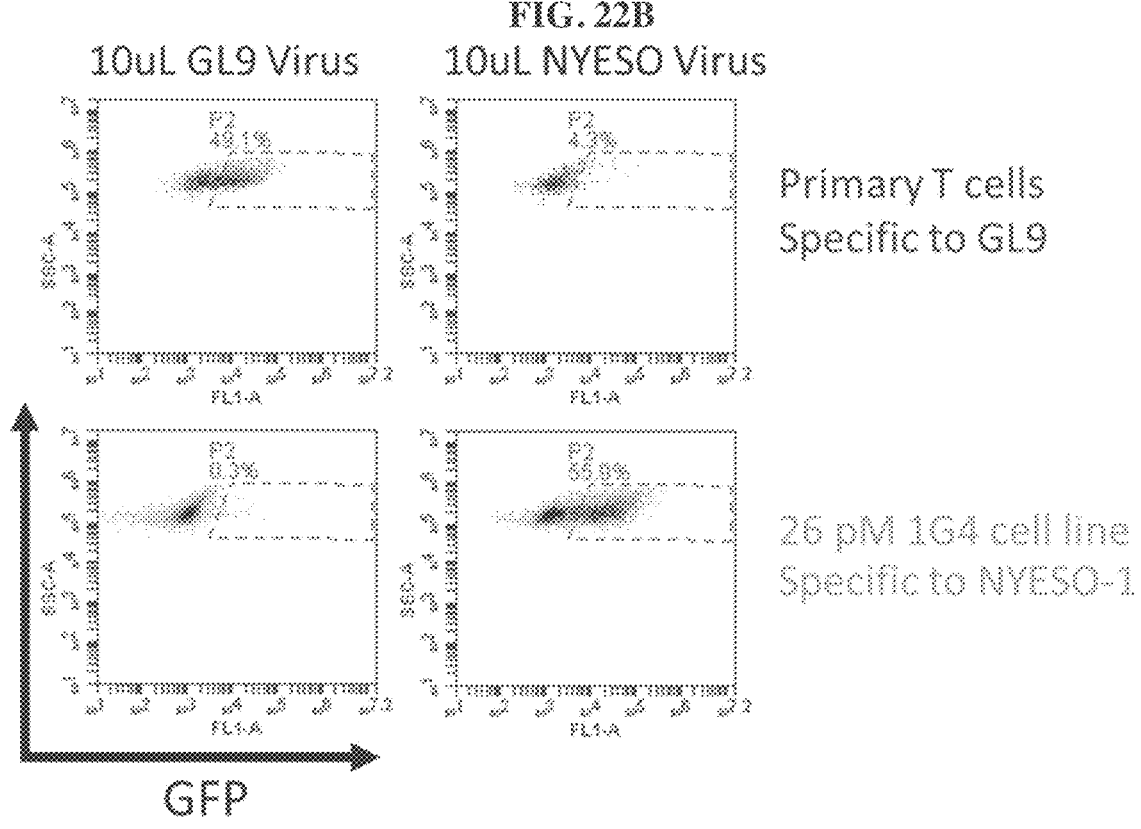

A primary T cell line specific for GL9 (presented by HLA-A2) was specifically and efficiently transduced by viruses having a mutated VSV-G envelope protein and displaying GL9 (FIGS. 22A-22B). About 50% of primary T cells were transduced by these GL9-targeting viruses. Conversely, these GL9-targeting viruses only transduced 0.3% of IG4 TCR-expressing T cells. The IG4 TCR-expressing T cells were specifically and efficiently transduced by viruses having a mutated VSV-G envelope protein and displaying NYESO-1 (55.9% transduction). Furthermore, the targeted virus infects the primary cells more efficiently than a wild-type VSV-G virus. These results indicate that the targeted viruses can even infect unstimulated primary cells.

Figure 23:
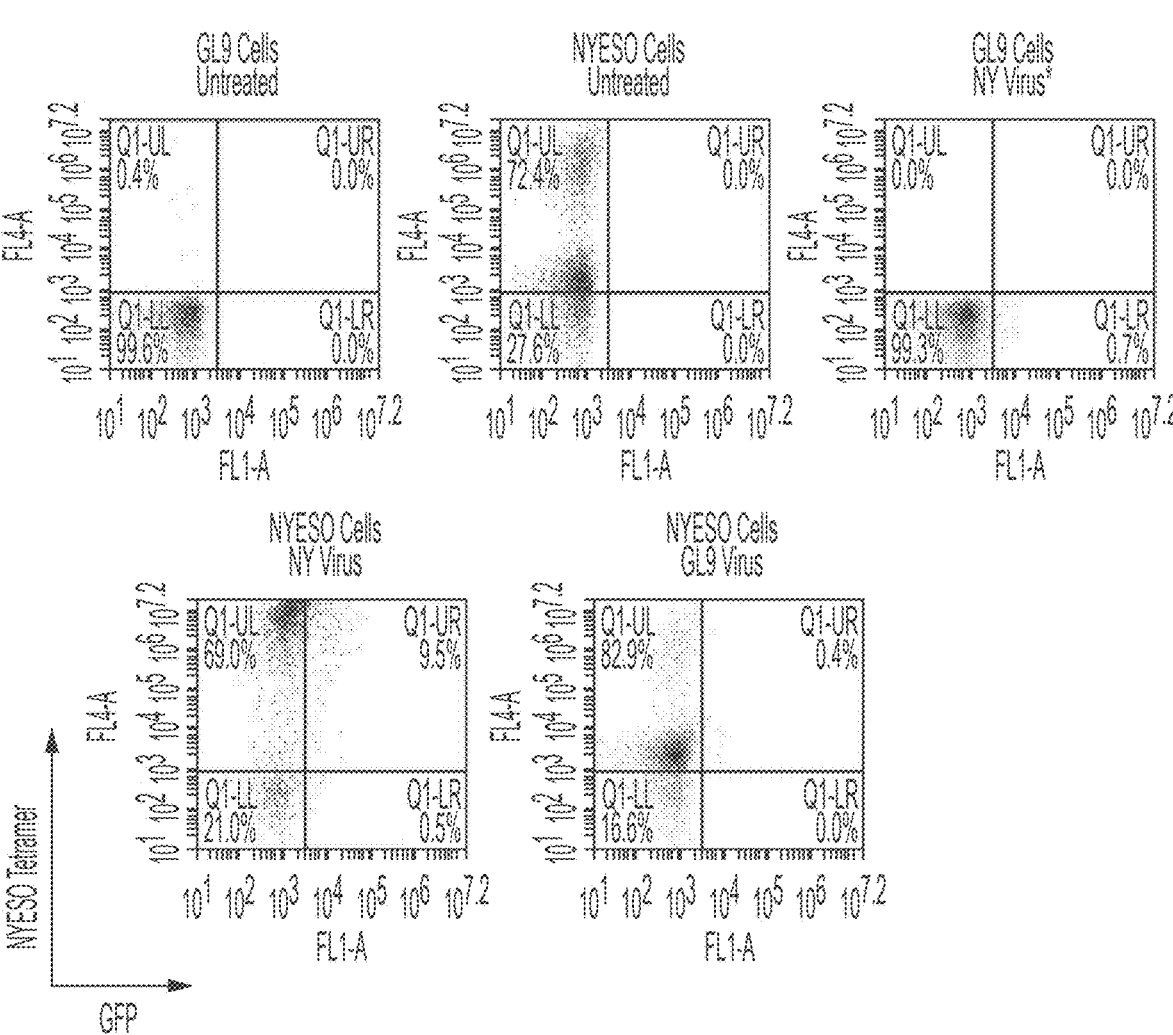
FIG. 23 depicts graphs showing that primary NYESO-1-reactive cells are specifically infected.
Figure 24:
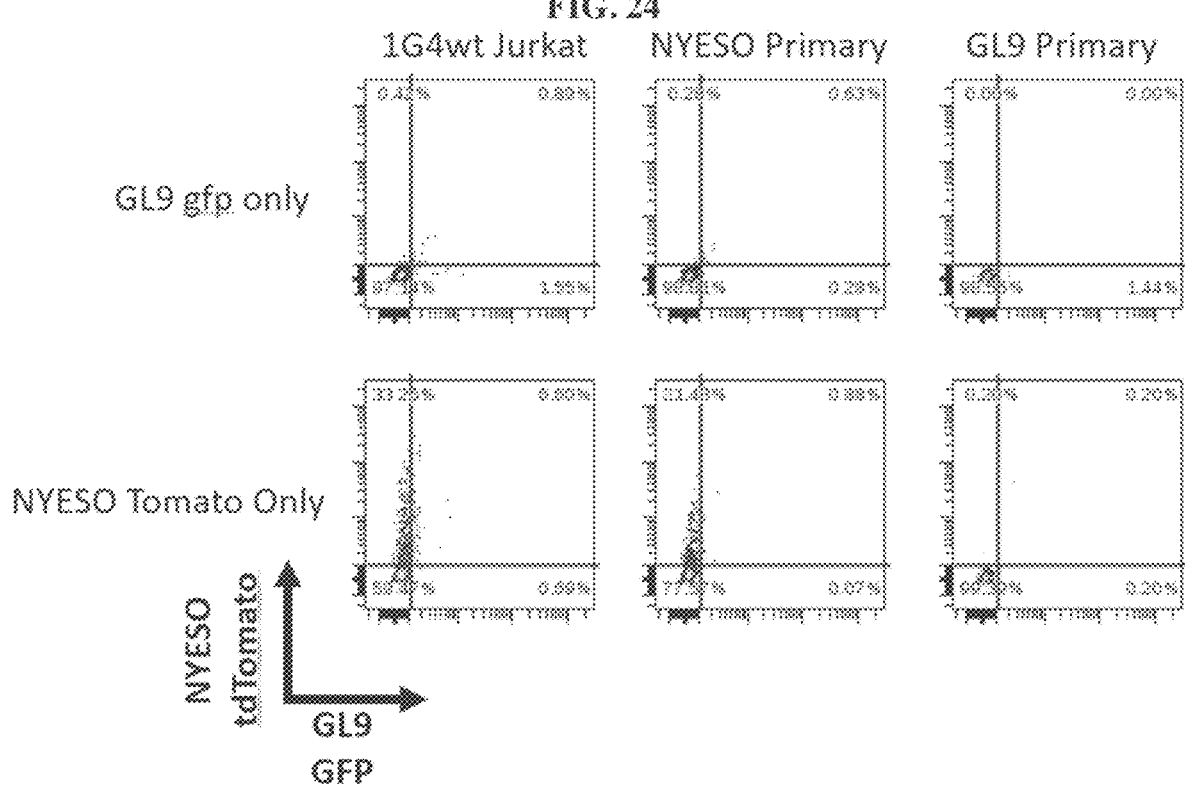
FIG. 24 depicts graphs showing that NYESO-1 targeted virus specifically infects expanded primary cells.

Similarly, a primary T cell line specific for NYESO (presented by HLA-A2) was specifically and efficiently transduced by viruses having a mutated VSV-G envelope protein and displaying NYESO-1 (FIGS. 23-24). Conversely, GL9-targeting viruses were unable to efficiently transduce the primary T cell line specific for NYESO. Collectively, these data demonstrate that primary NYESO-1-reactive cells, including expanded primary cells, can be specifically infected by NYESO-targeted viruses.

Example 11. Generation of Retroviruses Comprising CD80 Domain

Figure 25:
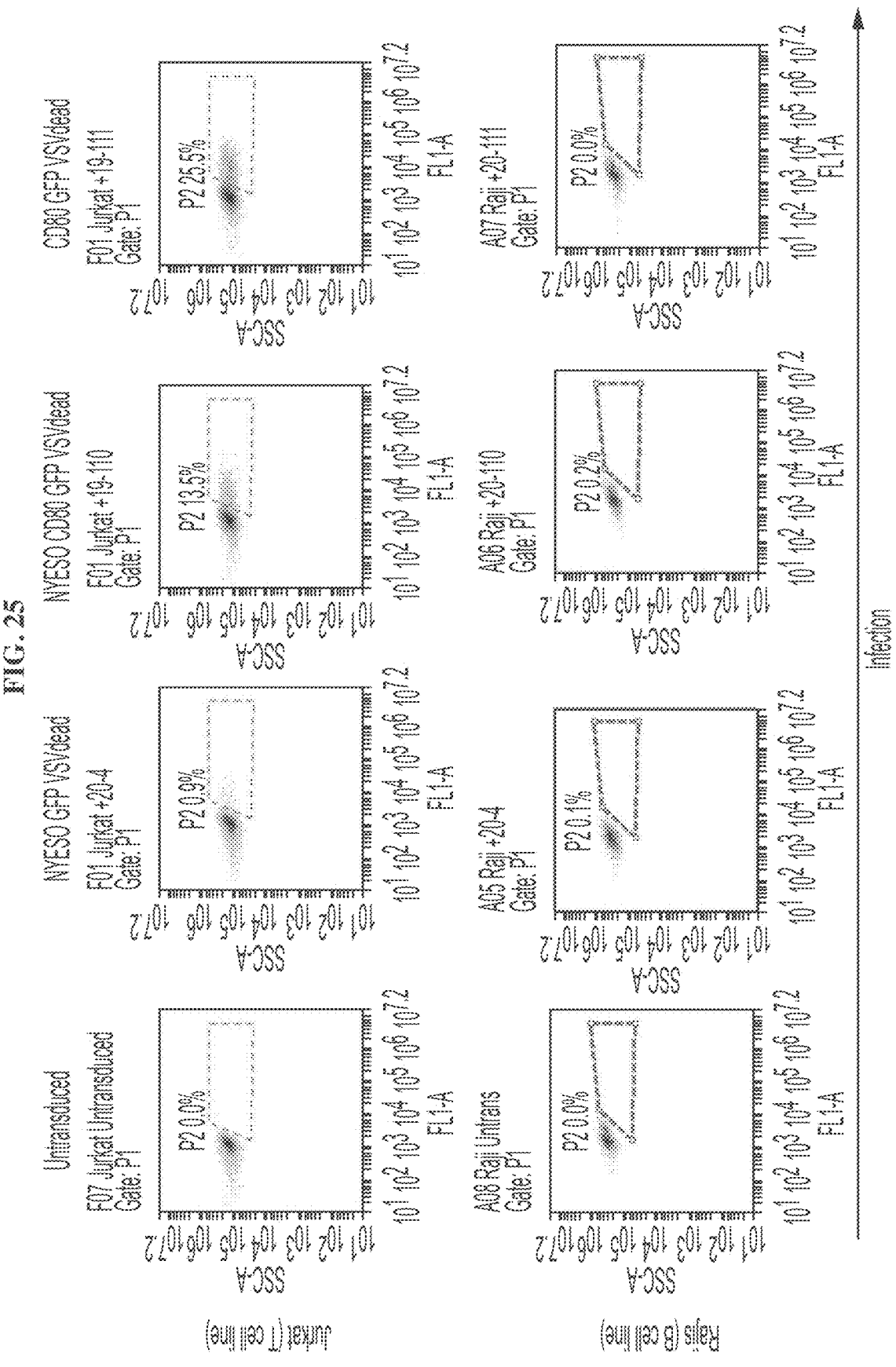
FIG. 25 depicts graphs showing the ability of a retrovirus comprising a mutated VSV-G viral envelope protein and a CD80 domain to specifically infect Jurkat T cells, relative to a B cell line.
Figure 26:
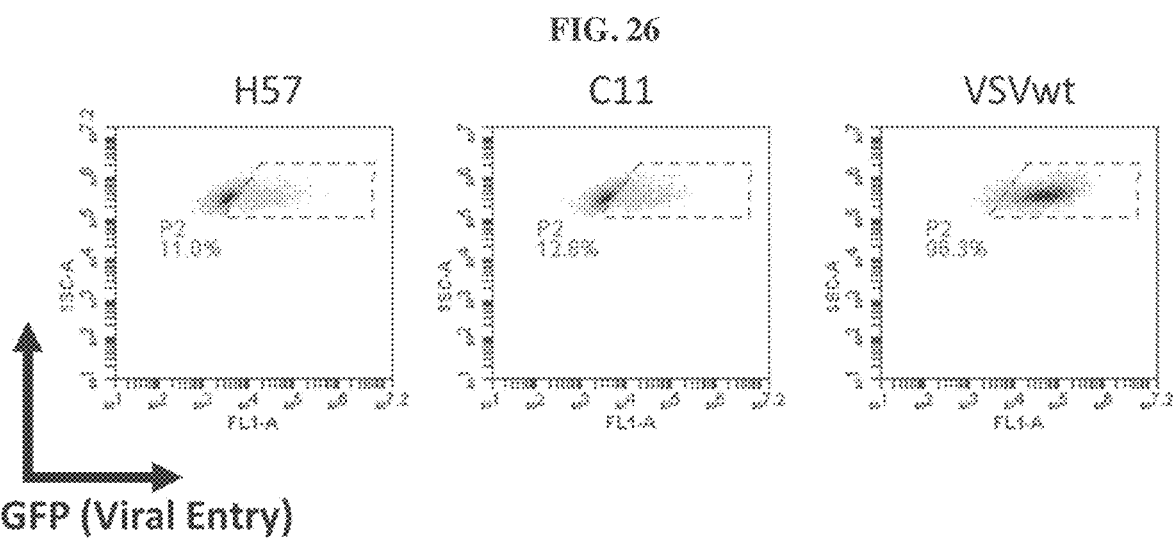
FIG. 26 depicts the ability of retroviruses comprising a mutated VSV-G viral envelope protein and either an anti-TCR-alpha beta antibody (H57) or an anti-CD3 antibody (C11) to infect of TCR-transduced 58−/− mouse cell lines.

A virus pseudotyped with a mutated VSV-G envelope protein and comprising a CD80 extracellular domain was generated using the protocol described in Example 1. This virus was able to specifically and efficiently infect Jurkat T cells (25.5% transduction), relative to B cells (0.0% transduction) (FIG. 25).

Similarly, a virus pseudotyped with a mutated VSV-G envelope protein and comprising a NYESO-1 pMHC and a CD80 extracellular domain was generated using the protocol described in Example 1. This virus was able to specifically and efficiently infect Jurkat T cells (13.5% transduction), relative to B cells (0.2% transduction) (FIG. 25). The presence of the CD80 domain enabled the transduction of this virus into the Jurkat T cells, as demonstrated by the inability of a virus a virus pseudotyped with a mutated VSV-G envelope protein and only comprising the NYESO-1 pMHC to infect these Jurkat T cells (0.9% transduction).

Collectively, these data show that the presence of CD80 on the virus surface mediates specific infection of T cells and demonstrates that CD80 could be used to generally target viruses to T cells.

Example 12. Murine Anti-CD3 Antibody Mediates Infection of TCR-Transduced 58−/− Cells Display of antibodies that are specific to the murine TCR constant region (H57 antibody) or the murine CD3 (2C11 antibody) on the surface of a virus enabled the viruses to infect mouse T cell lines. A virus comprising a mutated VSV-G viral envelope protein and the anti-TCR antibody provided 11.0% transduction of $58\alpha^-\beta^-$ mouse T hybridoma cells; and a virus comprising a mutated VSV-G viral envelope protein and the anti-CD3 antibody provided 12.8% transduction of $58\alpha^-\beta^-$ mouse T hybridoma cells.

Example 13. Generation of Viruses Comprising Dead Cocal Virus G Protein

A lentivirus was pseudotyped with a cocal virus G protein (Cocal-dead; amino acid comprising SEQ ID NO: 53) comprising mutations to reduce its infectivity. These mutations, at K64Q and R371A of the cocal virus G protein, were analogous to those mutations used in the VSV-dead variant described in Example 1. The cocal-dead virus further comprised a displayed anti-CD19 scFv antibody.

Figure 27:
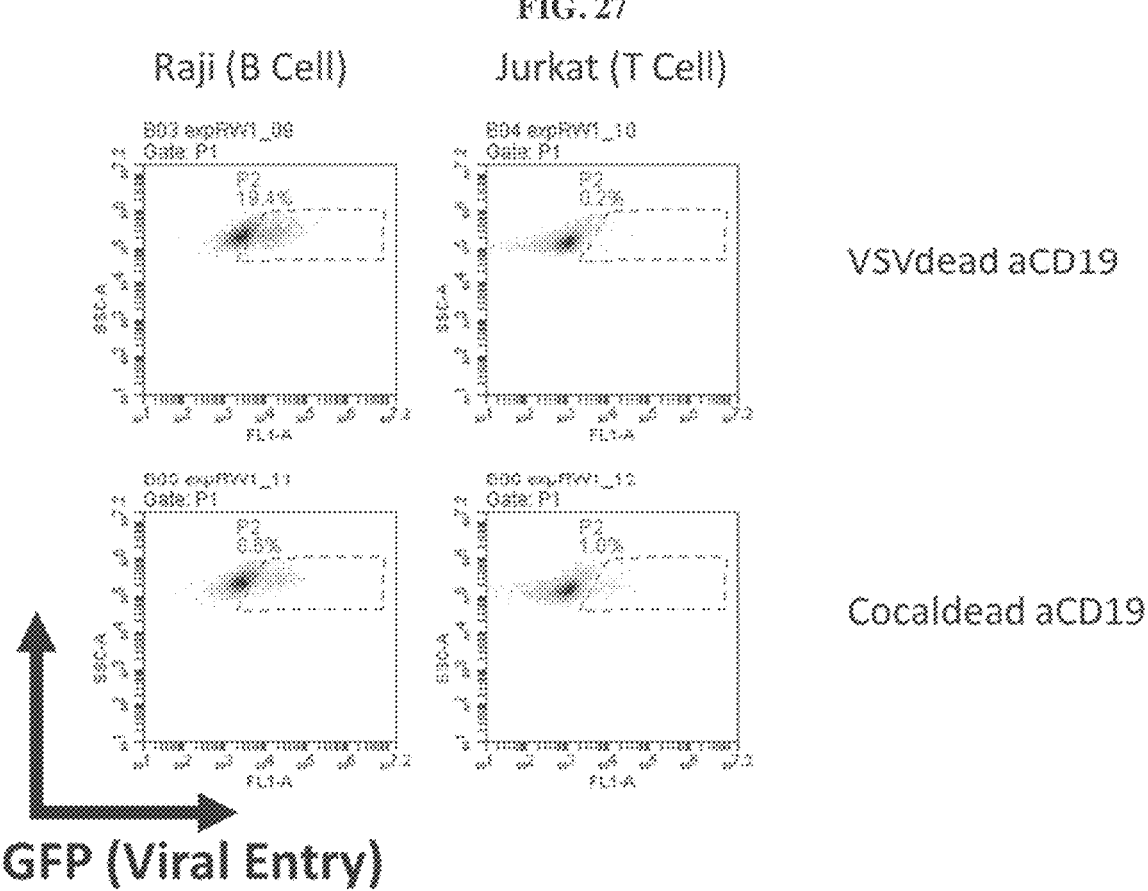
FIG. 27 depicts the ability of a retrovirus comprising either a mutated VSV-G viral envelope protein or a mutated cocal viral envelope protein; and an anti-CD19 scFv antibody to infect and enter CD19+ Raji cells, while not infecting CD19− Jurkat cells. A retrovirus comprising a wild-type VSV-G viral envelope protein and an anti-CD19 scFv antibody infects both CD19+ Raji cells and CD19− Jurkat cells.

This cocal-dead virus was able to transduce CD19$^+$ Raji B cells (8.6% transduction), as shown in FIG. 27, in a similar manner as a lentivirus comprising VSV-dead protein and displayed anti-CD19 scFv antibody.

These data demonstrates that the viral targeting strategy is highly robust and that any viral envelope protein (e.g., mutated VSV-G, mutated Nipah envelope, mutated Measles envelope, mutated cocal viral envelope) that can be mutated to reduce its infectivity can be effectively used.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

```
SEQUENCES
>Kappa leader sequence, amino acid (SEQ ID NO: 1):
METDTLLLWVLLLWVPGSTG >B2M signal peptide sequence, amino acid (SEQ ID NO: 2):
MSRSVALAVLALLSLSGLEA >PDGFR short stalk, amino acid (SEQ ID NO: 3):
AVGQDTQEVIVVPHSLPFK >PDGFR long stalk, amino acid (SEQ ID NO: 4):
ASAKPTTTPAPRPPTPAPTIASQPLSLRPEAARPAAGGAVHTRGLDFAK >Short flexible linker, amino acid (SEQ ID NO: 5):
GAPGAS >Long flexible linker, amino acid (SEQ ID NO: 6):
GAPGSGGGSGGGGSAS >Short flexible linker, amino acid (SEQ ID NO: 7):
GGGGS >IgG4 hinge domain, amino acid (SEQ ID NO: 8):
ASESKYGPPCPPCPAVGQDTQEVIVVPHSLPFK >Tetrameric coiled coil, amino acid (SEQ ID NO: 9):
ASGGGGSGELAAIKQELAAIKKELAAIKWELAAIKQGAG >Dimeric coiled coil, amino acid (SEQ ID NO: 10):
ASESKYGPPCPPCP >Wild-type VSV-G envelope protein (with leader sequence),
DNA sequence (SEQ ID NO: 11):
atgaagtgcctttttgtacttagccttttttattcattggggtgaattgcaagttcaccatagttt ttccacacaaccaaaaaggaaactggaaaaatgttccttctaattaccattattgcccgtcaag ctcagatttaaattggcataatgacttaataggcacagccatacaagtcaaaatgcccaagagt cacaaggctattcaagcagacggttggatgtgtcatgcttccaaatgggtcactacttgtgatt tccgctggtatggaccgaagtatataacacagtccatccgatccttcactccatctgtagaaca atgcaaggaaagcattgaacaaacgaaacaaggaacttggctgaatccaggcttccctcctcaa agttgtggatatgcaactgtgacggatgccgaagcagtgattgtccaggtgactcctcaccatg tgctggttgatgaatacacaggagaatgggttgattcacagttcatcaacggaaaatgcagcaa ttacatatgccccactgtccataactctacaacctggcattctgactataaggtcaaagggcta tgtgattctaacctcatttccatggacatcaccttcttctcagaggacggagagctatcatccc tgggaaaggagggcacagggttcagaagtaactactttgcttatgaaactggaggcaaggcctg caaaatgcaatactgcaagcattggggagtcagactcccatcaggtgtctggttcgagatggct gataaggatctctttgctgcagccagattccctgaatgcccagaagggtcaagtatctctgctc catctcagacctcagtggatgtaagtctaattcaggacgttgagaggatcttggattattccct ctgccaagaaacctggagcaaaatcagagcgggtcttccaatctctccagtggatctcagctat cttgctcctaaaaacccaggaaccggtcctgctttcaccataatcaatggtaccctaaaatact
```

-continued ttgagaccagatacatcagagtcgatattgctgctccaatcctctcaagaatggtcggaatgat cagtggaactaccacagaaagggaactgtgggatgactgggcaccatatgaagacgtggaaatt ggacccaatggagttctgaggaccagttcaggatataagtttcctttatacatgattggacatg gtatgttggactccgatcttcatcttagctcaaaggctcaggtgttcgaacatcctcacattca agacgctgcttcgcaacttcctgatgatgagagtttattttttggtgatactgggctatccaaa aatccaatcgagcttgtagaaggttggttcagtagttggaaaagctctattgcctcttttttct ttatcatagggttaatcattggactattcttggttctccgagttggtatccatctttgcattaa attaaagcacaccaagaaaagacagatttatacagacatagagatgaaccgacttggaaagtaa >Wild-type VSV-G envelope protein (with leader sequence),
amino acid sequence (SEQ ID NO: 12):
MKCLLYLAFLFIGVNCKFTIVFPHNQKGNWKNVPSNYHYCPSSSDLNWHNDLIGTAIQVKMPKS

HKAIQADGWMCHASKWVTTCDFRWYGPKYITQSIRSFTPSVEQCKESIEQTKQGTWLNPGFPPQ

SCGYATVTDAEAVIVQVTPHHVLVDEYTGEWVDSQFINGKCSNYICPTVHNSTTWHSDYKVKGL

CDSNLISMDITFFSEDGELSSLGKEGTGFRSNYFAYETGGKACKMQYCKHWGVRLPSGVWFEMA

DKDLFAAARFPECPEGSSISAPSQTSVDVSLIQDVERILDYSLCQETWSKIRAGLPISPVDLSY

LAPKNPGTGPAFTIINGTLKYFETRYIRVDIAAPILSRMVGMISGTTTERELWDDWAPYEDVEI

GPNGVLRTSSGYKFPLYMIGHGMLDSDLHLSSKAQVFEHPHIQDAASQLPDDESLFFGDTGLSK

NPIELVEGWFSSWKSSIASFFFIIGLIIGLFLVLRVGIHLCIKLKHTKKRQIYTDIEMNRLGK

>Wild-type VSV-G envelope protein, amino acid sequence
(SEQ ID NO: 13):
KFTIVFPHNQKGNWKNVPSNYHYCPSSSDLNWHNDLIGTAIQVKMPKSHKAIQADGWMCHASKW

VTTCDFRWYGPKYITQSIRSFTPSVEQCKESIEQTKQGTWLNPGFPPQSCGYATVTDAEAVIVQ

VTPHHVLVDEYTGEWVDSQFINGKCSNYICPTVHNSTTWHSDYKVKGLCDSNLISMDITFFSED

GELSSLGKEGTGFRSNYFAYETGGKACKMQYCKHWGVRLPSGVWFEMADKDLFAAARFPECPEG

SSISAPSQTSVDVSLIQDVERILDYSLCQETWSKIRAGLPISPVDLSYLAPKNPGTGPAFTIIN

GTLKYFETRYIRVDIAAPILSRMVGMISGTTTERELWDDWAPYEDVEIGPNGVLRTSSGYKFPL

YMIGHGMLDSDLHLSSKAQVFEHPHIQDAASQLPDDESLFFGDTGLSKNPIELVEGWFSSWKSS

IASFFFIIGLIIGLFLVLRVGIHLCIKLKHTKKRQIYTDIEMNRLGK

>VSV-G envelope protein (with leader sequence), DNA sequence
(SEQ ID NO: 14):
atgaagtgcctttttgtacttagcctttttattcattggggtgaattgcaagttcaccatagttt ttccacacaaccaaaaaggaaactggaaaaatgttccttctaattaccattattgcccgtcaag ctcagatttaaattggcataatgacttaataggcacagccttacaagtcaaaatgccccagagt cacaaggctattcaagcagacggttggatgtgtcatgcttccaaatgggtcactacttgtgatt tccgctggtatggaccgaagtatataacacagtccatccgatccttcactccatctgtagaaca atgcaaggaaagcattgaacaaacgaaacaaggaacttggctgaatccaggcttccctcctcaa agttgtggatatgcaactgtgacggatgccgaagcagtgattgtccaggtgactcctcaccatg tgctggttgatgaatacacaggagaatgggttgattcacagttcatcaacggaaaatgcagcaa ttacatatgcccccactgtccataactctacaacctggcattctgactataaggtcaaagggcta tgtgattctaacctcatttccatggacatcaccttcttctcagaggacggagagctatcatccc tgggaaaggagggcacagggttcagaagtaactactttgcttatgaaactggaggcaaggcctg caaaatgcaatactgcaagcattggggagtcagactcccatcaggtgtctggttcgagatggct gataaggatctcttgctgcagccagattccctgaatgcccagaagggtcaagtatctctgctc catctcagacctcagtggatgtaagtctaattcaggacgttgagaggatcttggattattccct -continued ctgccaagaaacctggagcaaaatcagagcgggtcttccaatctctccagtggatctcagctat cttgctcctaaaaacccaggaaccggtcctgctttcaccataatcaatggtaccctaaaatact ttgagaccagatacatcagagtcgatattgctgctccaatcctctcaagaatggtcggaatgat cagtggaactaccacagaagccgaactgtgggatgactgggcaccatatgaagacgtggaaatt ggacccaatggagttctgaggaccagttcaggatataagtttcctttatacatgattggacatg gtatgttggactccgatcttcatcttagctcaaaggctcaggtgttcgaacatcctcacattca agacgctgcttcgcaacttcctgatgatgagagtttattttttggtgatactgggctatccaaa aatccaatcgagcttgtagaaggttggttcagtagttggaaaagctctattgcctctttttttct ttatcatagggttaatcattggactattcttggttctccgagttggtatccatctttgcattaa attaaagcacaccaagaaaagacagatttatacagacatagagatgaaccgacttggaaagtaa >VSV-G envelope protein (with leader sequence), amino acid
sequence (SEQ ID NO: 15):
MKCLLYLAFLFIGVNCKFTIVFPHNQKGNWKNVPSNYHYCPSSSDLNWHNDLIGTALQVKMPQS

HKAIQADGWMCHASKWVTTCDFRWYGPKYITQSIRSFTPSVEQCKESIEQTKQGTWLNPGFPPQ

SCGYATVTDAEAVIVQVTPHHVLVDEYTGEWVDSQFINGKCSNYICPTVHNSTTWHSDYKVKGL

CDSNLISMDITFFSEDGELSSLGKEGTGFRSNYFAYETGGKACKMQYCKHWGVRLPSGVWFEMA

DKDLFAAARFPECPEGSSISAPSQTSVDVSLIQDVERILDYSLCQETWSKIRAGLPISPVDLSY

LAPKNPGTGPAFTIINGTLKYFETRYIRVDIAAPILSRMVGMISGTTTEAELWDDWAPYEDVEI

GPNGVLRTSSGYKFPLYMIGHGMLDSDLHLSSKAQVFEHPHIQDAASQLPDDESLFFGDTGLSK

NPIELVEGWFSSWKSSIASFFFIIGLIIGLFLVLRVGIHLCIKLKHTKKRQIYTDIEMNRLGK

>I41L/K47Q/R354A VSV-G envelope protein, amino acid sequence
(SEQ ID NO: 16):
KFTIVFPHNQKGNWKNVPSNYHYCPSSSDLNWHNDLIGTALQVKMPQSHKAIQADGWMCHASKW

VTTCDFRWYGPKYITQSIRSFTPSVEQCKESIEQTKQGTWLNPGFPPQSCGYATVTDAEAVIVQ

VTPHHVLVDEYTGEWVDSQFINGKCSNYICPTVHNSTTWHSDYKVKGLCDSNLISMDITFFSED

GELSSLGKEGTGFRSNYFAYETGGKACKMQYCKHWGVRLPSGVWFEMADKDLFAAARFPECPEG

SSISAPSQTSVDVSLIQDVERILDYSLCQETWSKIRAGLPISPVDLSYLAPKNPGTGPAFTIIN

GTLKYFETRYIRVDIAAPILSRMVGMISGTTTEAELWDDWAPYEDVEIGPNGVLRTSSGYKFPL

YMIGHGMLDSDLHLSSKAQVFEHPHIQDAASQLPDDESLFFGDTGLSKNPIELVEGWFSSWKSS

IASFFFIIGLIIGLFLVLRVGIHLCIKLKHTKKRQIYTDIEMNRLGK

>K47Q/R354A VSV-G envelope protein,
amino acid sequence (SEQ ID NO: 17):
KFTIVFPHNQKGNWKNVPSNYHYCPSSSDLNWHNDLIGTAIQVKMPQSHKAIQADGWMCHASKW

VTTCDFRWYGPKYITQSIRSFTPSVEQCKESIEQTKQGTWLNPGFPPQSCGYATVTDAEAVIVQ

VTPHHVLVDEYTGEWVDSQFINGKCSNYICPTVHNSTTWHSDYKVKGLCDSNLISMDITFFSED

GELSSLGKEGTGFRSNYFAYETGGKACKMQYCKHWGVRLPSGVWFEMADKDLFAAARFPECPEG

SSISAPSQTSVDVSLIQDVERILDYSLCQETWSKIRAGLPISPVDLSYLAPKNPGTGPAFTIIN

GTLKYFETRYIRVDIAAPILSRMVGMISGTTTEAELWDDWAPYEDVEIGPNGVLRTSSGYKFPL

YMIGHGMLDSDLHLSSKAQVFEHPHIQDAASQLPDDESLFFGDTGLSKNPIELVEGWFSSWKSS

IASFFFIIGLIIGLFLVLRVGIHLCIKLKHTKKRQIYTDIEMNRLGK

>Exemplary wild-type measles envelope protein (with leader
sequence), DNA sequence (SEQ ID NO: 18):
ATGGGCAGCCGGATCGTGATCAACCGGGAGCACCTGATGATCGACCGGCCCTACGTGCTGCTGG

CCGTGCTGTTCGTGATGTTCCTGAGCCTGATCGGCTTGCTAGCCATTGCTGGAATCCGGCTGCA

-continued

```
CAGAGCCGCCATCTACACCGCCGAGATCCACAAGAGCCTGAGCACCAACCTGGACGTGACCAAC

AGCATCGAGCATCAGGTCAAGGACGTGCTGACCCCCCTGTTTAAGATCATCGGCGACGAAGTGG

GCCTGCGGACCCCCCAGAGATTCACCGACCTGGTCAAGTTCATCAGCGACAAGATCAAGTTCCT

GAACCCCGACCGGGAGTACGACTTCCGGGACCTGACCTGGTGCATCAACCCCCCCGAGCGGATC

AAGCTGGACTACGACCAGTACTGCGCCGATGTGGCCGCCGAGGAACTGATGAATGCATTGGTGA

ACTCAACTCTACTGGAGACCAGAACAACCAATCAGTTCCTAGCTGTCTCAAAGGGAAACTGCTC

AGGGCCCACTACAATCAGAGGTCAATTCTCAAACATGTCGCTGTCCCTGTTAGACTTGTATTTA

GGTCGAGGTTACAATGTGTCATCTATAGTCACTATGACATCCCAGGGAATGTATGGGGGAACTT

ACCTAGTGGAAAAGCCTAATCTGAGCAGCAAAAGGTCAGAGTTGTCACAACTGAGCATGTACCG

AGTGTTTGAAGTAGGTGTTATCAGAAATCCGGGTTTGGGGGCTCCGGTGTTCCATATGACAAAC

TATCTTGAGCAACCAGTCAGTAATGATCTCAGCAACTGTATGGTGGCTTTGGGGGAGCTCAAAC

TCGCAGCCCTTTGTCACGGGGAAGATTCTATCACAATTCCCTATCAGGGATCAGGGAAAGGTGT

CAGCTTCCAGCTCGTCAAGCTAGGTGTCTGGAAATCCCCAACCGACATGCAATCCTGGGTCCCC

TTATCAACGGATGATCCAGTGATAGACAGGCTTTACCTCTCATCTCACAGAGGTGTTATCGCTG

ACAACCAAGCAAATGGGCTGTCCCGACAACACGAACAGATGACAAGTTGCGAATGGAGACATG

CTTCCAACAGGCGTGTAAGGGTAAAATCCAAGCACTCTGCGAGAATCCCGAGTGGGCACCATTG

AAGGATAACAGGATTCCTTCATACGGGGTCTTGTCTGTTGATCTGAGTCTGACAGTTGAGCTTA

AAATCAAAATTGCTTCGGGATTCGGGCCATTGATCACACACGGTTCAGGGATGGACCTATACAA

ATCCAACCACAACAATGTGTATTGGCTGACTATCCCGCCAATGAAGAACCTAGCCTTAGGTGTA

ATCAACACATTGGAGTGGATACCGAGATTCAAGGTTAGTCCCtatCTCTTCAcaGTCCCAATTA

AGGAAGCAGGCGGAGACTGCCATGCCCCAACATACCTACCTGCGGAGGTGGATGGTGATGTCAA

ACTCAGTTCCAATCTGGTGATTCTACCTGGTCAAGATCTCCAATATGTTTTGGCAACCTACGAT

ACTTCCcgGGTTGAACATGCTGTGGTTTATTACGTTTACAGCCCAAGCCGCTCATTTTCTTACT

TTTATCCTTTTAGGTTGCCTATAAAGGGGGTCCCCATCGAATTACAAGTGGAATGCTTCACATG

GGACCAAAAACTCTGGTGCCGTCACTTCTGTGTGCTTGCGGACTCAGAATCTGGTGGACATATC

ACTCACTCTGGGATGGTGGGCATGGGAGTCAGCTGCACAGTCACCCGGGAAGATGGAACCAATG

ACTACAAAGACGATGACGACAAGTGA
```

>Exemplary wild-type measles envelope protein, amino acid sequence
(SEQ ID NO: 19):
```
MGSRIVINREHLMIDRPYVLLAVLFVMFLSLIGLLAIAGIRLHRAAIYTAEIHKSLSTNLDVTN

SIEHQVKDVLTPLFKIIGDEVGLRTPQRFTDLVKFISDKIKFLNPDREYDFRDLTWCINPPERI

KLDYDQYCADVAAEELMNALVNSTLLETRTTNQFLAVSKGNCSGPTTIRGQFSNMSLSLLDLYL

GRGYNVSSIVTMTSQGMYGGTYLVEKPNLSSKRSELSQLSMYRVFEVGVIRNPGLGAPVFHMTN

YLEQPVSNDLSNCMVALGELKLAALCHGEDSITIPYQGSGKGVSFQLVKLGVWKSPTDMQSWVP

LSTDDPVIDRLYLSSHRGVIADNQAKWAVPTTRTDDKLRMETCFQQACKGKIQALCENPEWAPL

KDNRIPSYGVLSVDLSLTVELKIKIASGFGPLITHGSGMDLYKSNHNNVYWLTIPPMKNLALGV

INTLEWIPRFKVSPYLFTVPIKEAGGDCHAPTYLPAEVDGDVKLSSNLVILPGQDLQYVLATYD

TSRVEHAVVYYVYSPSRSFSYFYPFRLPIKGVPIELQVECFTWDQKLWCRHFCVLADSESGGHI

THSGMVGMGVSCTVTREDGTNDYKDDDDK
```

>Exemplary mutant measles envelope protein, DNA sequence
(SEQ ID NO: 20):
```
ATGGGCAGCCGGATCGTGATCAACCGGGAGCACCTGATGATCGACCGGCCCTACGTGCTGCTGG

CCGTGCTGTTCGTGATGTTCCTGAGCCTGATCGGCTTGCTAGCCATTGCTGGAATCCGGCTGCA
```

-continued

```
CAGAGCCGCCATCTACACCGCCGAGATCCACAAGAGCCTGAGCACCAACCTGGACGTGACCAAC

AGCATCGAGCATCAGGTCAAGGACGTGCTGACCCCCCTGTTTAAGATCATCGGCGACGAAGTGG

GCCTGCGGACCCCCCAGAGATTCACCGACCTGGTCAAGTTCATCAGCGACAAGATCAAGTTCCT

GAACCCCGACCGGGAGTACGACTTCCGGGACCTGACCTGGTGCATCAACCCCCCCGAGCGGATC

AAGCTGGACTACGACCAGTACTGCGCCGATGTGGCCGCCGAGGAACTGATGAATGCATTGGTGA

ACTCAACTCTACTGGAGACCAGAACAACCAATCAGTTCCTAGCTGTCTCAAAGGGAAACTGCTC

AGGGCCCACTACAATCAGAGGTCAATTCTCAAACATGTCGCTGTCCCTGTTAGACTTGTATTTA

GGTCGAGGTTACAATGTGTCATCTATAGTCACTATGACATCCCAGGGAATGTATGGGGGAACTT

ACCTAGTGGAAAAGCCTAATCTGAGCAGCAAAAGGTCAGAGTTGTCACAACTGAGCATGTACCG

AGTGTTTGAAGTAGGTGTTATCAGAAATCCGGGTTTGGGGGCTCCGGTGTTCCATATGACAAAC

TATCTTGAGCAACCAGTCAGTAATGATCTCAGCAACTGTATGGTGGCTTTGGGGGAGCTCAAAC

TCGCAGCCCTTTGTCACGGGGAAGATTCTATCACAATTCCCTATCAGGGATCAGGGAAAGGTGT

CAGCTTCCAGCTCGTCAAGCTAGGTGTCTGGAAATCCCCAACCGACATGCAATCCTGGGTCCCC

TTATCAACGGATGATCCAGTGATAGACAGGCTTTACCTCTCATCTCACAGAGGTGTTATCGCTG

ACAACCAAGCAAATGGGCTGTCCCGACAACACGAACAGATGACAAGTTGCGAATGGAGACATG

CTTCCAACAGGCGTGTAAGGGTAAAATCCAAGCACTCTGCGAGAATCCCGAGTGGGCACCATTG

AAGGATAACAGGATTCCTTCATACGGGGTCTTGTCTGTTGATCTGAGTCTGACAGTTGAGCTTA

AAATCAAAATTGCTTCGGGATTCGGGCCATTGATCACACACGGTTCAGGGATGGACCTATACAA

ATCCAACCACAACAATGTGTATTGGCTGACTATCCCGCCAATGAAGAACCTAGCCTTAGGTGTA

ATCAACACATTGGAGTGGATACCGAGATTCAAGGTTAGTCCCGCGCTCTTCAATGTCCCAATTA

AGGAAGCAGGCGGAGACTGCCATGCCCCAACATACCTACCTGCGGAGGTGGATGGTGATGTCAA

ACTCAGTTCCAATCTGGTGATTCTACCTGGTCAAGATCTCCAATATGTTTTGGCAACCTACGAT

ACTTCCGCGGTTGAACATGCTGTGGTTTATTACGTTTACAGCCCAAGCCGCTCATTTTCTTACT

TTTATCCTTTTAGGTTGCCTATAAAGGGGGTCCCCATCGAATTACAAGTGGAATGCTTCACATG

GGACCAAAAACTCTGGTGCCGTCACTTCTGTGTGCTTGCGGACTCAGAATCTGGTGGACATATC

ACTCACTCTGGGATGGTGGGCATGGGAGTCAGCTGCACAGTCACCCGGGAAGATGGAACCAATG

ACTACAAAGACGATGACGACAAGTGA
```

>Exemplary mutant measles envelope protein,
amino acid sequence (SEQ ID NO: 21):

```
MGSRIVINREHLMIDRPYVLLAVLFVMFLSLIGLLAIAGIRLHRAAIYTAEIHKSLSTNLDVTN

SIEHQVKDVLTPLFKIIGDEVGLRTPQRFTDLVKFISDKIKFLNPDREYDFRDLTWCINPPERI

KLDYDQYCADVAAEELMNALVNSTLLETRTTNQFLAVSKGNCSGPTTIRGQFSNMSLSLLDLYL

GRGYNVSSIVTMTSQGMYGGTYLVEKPNLSSKRSELSQLSMYRVFEVGVIRNPGLGAPVFHMTN

YLEQPVSNDLSNCMVALGELKLAALCHGEDSITIPYQGSGKGVSFQLVKLGVWKSPTDMQSWVP

LSTDDPVIDRLYLSSHRGVIADNQAKWAVPTTRTDDKLRMETCFQQACKGKIQALCENPEWAPL

KDNRIPSYGVLSVDLSLTVELKIKIASGFGPLITHGSGMDLYKSNHNNVYWLTIPPMKNLALGV

INTLEWIPRFKVSPALFNVPIKEAGGDCHAPTYLPAEVDGDVKLSSNLVILPGQDLQYVLATYD

TSAVEHAVVYVVYSPSRSFSYFYPFRLPIKGVPIELQVECFTWDQKLWCRHFCVLADSESGGHI

THSGMVGMGVSCTVTREDGTNDYKDDDDK
```

-continued

>Exemplary mutant Nipah envelope protein, DNA sequence
(SEQ ID NO: 22):
ATGAAGAAGATCAACGAGGGCCTGCTGGACAGCAAGATCCTGAGCGCCTTCAACACCGTGATTG

CCCTGCTGGGCTCTATCGTGATCATCGTGATGAACATCATGATCATCCAGAACTACACCCGGTC

CACCGACAACCAGGCCGTGATTAAGGATGCTCTGCAGGGAATCCAGCAGCAGATCAAAGGCCTG

GCCGACAAGATCGGCACAGAGATCGGCCCTAAGGTGTCCCTGATCGACACCAGCAGCACCATCA

CAATCCCCGCCAATATCGGACTGCTGGGAAGCAAGATCAGCCAGAGCACCGCCAGCATCAACGA

GAACGTGAACGAGAAGTGCAAGTTCACCCTGCCTCCACTGAAGATCCACGAGTGCAACATCAGC

TGCCCCAATCCTCTGCCATTCAGAGAGTACAGACCCCAGACAGAGGGCGTGTCCAATCTCGTGG

GCCTGCCTAACAACATCTGCCTGCAGAAAACCAGCAACCAGATCCTGAAGCCTAAGCTGATCTC

CTACACACTGCCCGTCGTGGGCCAGAGCGGCACCTGTATTACAGATCCTCTGCTGGCCATGGAC

GAGGGCTACTTTGCCTACAGCCACCTGGAAAGAATCGGCAGCTGTAGCCGGGGAGTGTCCAAGC

AGAGAATCATCGGCGTGGGCGAAGTGCTGGATAGAGGCGACGAAGTGCCCAGCCTGTTCATGAC

CAATGTGTGGACCCCTCCTAATCCTAACACCGTGTACCACTGCAGCGCCGTGTACAACAACGAG

TTCTACTACGTGCTGTGCGCCGTGTCCACAGTGGGCGACCCTATCCTGAACAGCACCTATTGGA

GCGGCAGCCTGATGATGACCAGACTGGCCGTGAAGCCCAAGAGCAATGGCGGCGGATACAACCA

GCATCAGCTGGCCCTGCGGTCCATCGAGAAGGGCAGATACGACAAAGTGATGCCTTACGGCCCC

AGCGGCATCAAGCAAGGCGATACCCTGTACTTTCCCGCCGTGGGATTTCTCGTGCGGACCGAGT

TCAAGTACAACGACAGCAACTGCCCCATCACCAAGTGCCAGTACAGCAAGCCCGAGAACTGCAG

ACTGAGCATGGGCATCAGACCCAACAGCCACTACATCCTGAGAAGCGGCCTGCTGAAGTACAAC

CTGAGCGACGGCGAGAACCCCAAGGTGGTGTTCATCGAGATCAGCGACCAGCGGCTGTCTATCG

GCAGCCCCTCCAAGATCTACGACTCTCTGGGCCAGCCAGTGTTCTACCAGGCCAGCTTTAGCTG

GGACACCATGATCAAGTTCGGCGACGTGCTGACCGTGAATCCCCTGGTGGTCAACTGGCGGAAC

AATACCGTGATCAGCCGGCCTGGCCAGTCTCAGTGCCCCAGATTCAATACCTGTCCTGCCATTT

GCGCCGAAGGCGTGTACAATGACGCCTTCCTGATCGATCGGATCAACTGGATCTCTGCCGGCGT

GTTCCTGGACTCTAATGCCACAGCCGCCAATCCTGTGTTCACCGTGTTCAAGGACAATGAGATC

CTGTATCGGGCCCAGCTGGCCTCCGAGGACACAAATGCCCAGAAAACAATCACCAACTGCTTTC

TGCTCAAGAACAAGATCTGGTGCATCAGCCTGGTGGAAATCTACGACACCGGCGACAACGTGAT

CAGGCCCAAGCTGTTCGCCGTGAAGATCCCTGAGCAGTGTACAGGCGGCGGAGGATCTGGCGGA

GGTGGAAGCGGAGGCGGTGGATCTGCTAGCGATTACAAGGATGACGACGATAAGTGA

>Exemplary mutant Nipah envelope protein, amino acid sequence
(SEQ ID NO: 23):
MKKINEGLLDSKILSAFNTVIALLGSIVIIVMNIMIIQNYTRSTDNQAVIKDALQGIQQQIKGL

ADKIGTEIGPKVSLIDTSSTITIPANIGLLGSKISQSTASINENVNEKCKFTLPPLKIHECNIS

CPNPLPFREYRPQTEGVSNLVGLPNNICLQKTSNQILKPKLISYTLPVVGQSGTCITDPLLAMD

EGYFAYSHLERIGSCSRGVSKQRIIGVGEVLDRGDEVPSLFMTNVWTPPNPNTVYHCSAVYNNE

FYYVLCAVSTVGDPILNSTYWSGSLMMTRLAVKPKSNGGGYNQHQLALRSIEKGRYDKVMPYGP

SGIKQGDTLYFPAVGFLVRTEFKYNDSNCPITKCQYSKPENCRLSMGIRPNSHYILRSGLLKYN

LSDGENPKVVFIEISDQRLSIGSPSKIYDSLGQPVFYQASFSWDTMIKFGDVLTVNPLVVNWRN

NTVISRPGQSQCPRFNTCPAICAEGVYNDAFLIDRINWISAGVFLDSNATAANPVFTVFKDNEI

LYRAQLASEDTNAQKTITNCFLLKNKIWCISLVEIYDTGDNVIRPKLFAVKIPEQCTGGGSGG

GGSGGGGSASDYKDDDDK

-continued

>IG4 TCR (Variant that binds to NYESO-1 antigen with 32 µM
binding affinity), amino acid sequence (SEQ ID NO: 24):
MSIGLLCCAALSLLWAGPVNAGVTQTPKFQVLKTGQSMTLQCAQDMNHEYMSWYRQDPGMGLRL

IHYSVGAGITDQGEVPNGYNVSRSTTEDFPLRLLSAAPSQTSVYFCASSYVGNTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLIQSSQREQTSGRLNASLDKSSGSSTLYIAASQPGDSATYLCAVRPTSG

GSYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>IG4 TCR (Variant that binds to NYESO-1 antigen with 84 nM
binding affinity), amino acid sequence (SEQ ID NO: 25):
MSIGLLCCAALSLLWAGPVNAGVTQTPKFQVLKTGQSMTLQCAQDMNHEYMSWYRQDPGMGLRL

IHYSVGAQTTDQGEVPNGYNVSRSTIEDFPLRLLSAAPSQTSVYFCASSYLGNTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLIQSSQREQTSGRLNASLDKSSGSSTLYIAASQPGDSATYLCAVRPMIG

GTYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>IG4 TCR (Variant that binds to NYESO-1 antigen with 5 nM
binding affinity), amino acid sequence (SEQ ID NO: 26):
MSIGLLCCAALSLLWAGPVNAGVTQTPKFQVLKTGQSMTLQCAQDMNHEYMSWYRQDPGMGLRL

IHYSVGAGTTDRGEVPNGYNVSRSTIEDFPLRLLSAAPSQTSVYFCASSYVGDTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLIQSSQREQTSGRLNASLDKSSGSSTLYIAASQPGDSATYLCAVRPLLD

GTYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>IG4 TCR (Variant that binds to NYESO-1 antigen with 26 pM
binding affinity), amino acid sequence (SEQ ID NO: 27):
MSIGLLCCAALSLLWAGPVNAGVTQTPKFQVLKTGQSMTLQCAQDMNHEYMSWYRQDPGMGLRL

IHYSVAIQTTDQGEVPNGYNVSRSTIEDFPLRLLSAAPSQTSVYFCASSYLGNTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLITPWQREQTSGRLNASLDKSSGSSTLYIAASQPGDSATYLCAVRPLLD

GTYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>868 TCR (Beta Chain-P2A-Alpha Chain), amino acid sequence
(SEQ ID NO: 31):
MSIGLLCCAALSLLWAGPVNADAGVTQSPTHLIKTRGQQVTLRCSPKQGHDTVSWYQQALGQGP

QFIFQYYEEEERQRGNFPDRFSGHQFPNYSSELNVNALLLGDSALYLCASSDTVSYEQYFGPGT

RLTVTEDLKNVFPPEVAVFEPSEAEISHTQKATLVCLATGFYPDHVELSWWVNGKEVHSGVSTD

PQPLKEQPALNDSRYCLSSRLRVSATFWQDPRNHFRCVQFYGLSENDEWTQDRAKPVTQIVSA

EAWGRADCGFTSESYQQGVLSATILYEILLGKATLYAVLVSALVLMAMVKRKDSRGGSATNFSL

LKQAGDVEENPGPMETLLGLLILWLQLQWVSSKEVEQNSGPLSVPEGAIASLNCTYSDRGSQSF

FWYRQYSGKSPELIMFIYSNGDKEDGRFTAQLNKASQYISLLIRDSKLSDSATYLCAVRTNSGY

ALNFGKGTSLLVTPHIQKPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKLVEKSFETDTNLNFQN

LSVIGFRILLLKVAGFNLLMTLRLWSS

>CMV C7 TCR, amino acid sequence (SEQ ID NO: 33):
MGTRLLFWVAFCLLGADHTGAGVSQSPSNKVTEKGKDVELRCDPISGHTALYWYRQRLGQGLEF

LIYFQGNSAPDKSGLPSDRFSAERTGESVSTLTIQRTQQEDSAVYLCASSQTQLWETQYFGPGT

RLLVLEDLKNVFPPEVAVFEPSEAEISHTQKATLVCLATGFYPDHVELSWWVNGKEVHSGVSTD

PQPLKEQPALNDSRYCLSSRLRVSATFWQNPRNHFRCVQFYGLSENDEWTQDRAKPVTQIVSA

EAWGRADCGFTSESYQQGVLSATILYEILLGKATLYAVLVSALVLMAMVKRKDSRGGSATNFSL

LKQAGDVEENPGPMEKNPLAAPLLILWFHLDCVSSILNVEQSPQSLHVQEGDSTNFTCSFPSSN

FYALHWYRWETAKSPEALFVMTLNGDEKKKGRISATLNTKEGYSYLYIKGSQPEDSATYLCAFI

TGNQFYFGTGTSLTVIPNIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>SL9 pMHC (5L9 peptide portion bolded), amino acid sequence
(SEQ ID NO: 35):
MSRSVALAVLALLSLSGLEASLYNTVATLGGGASGGGGSGGGGSIQRTPKIQVYSRHPAENGKS

NFLNCYVSGFHPSDIEVDLLKNGERIEKVEHSDLSFSKDWSFYLLYYTEFTPTEKDEYACRVNH

VTLSQPKIVKWDRDMGGGGSGGGGSGGGGSGGGGSHSMRYFFTSVSRPGRGEPRFIAVGYVDDT

QFVRFDSDAASQRMEPRAPWIEQEGPEYWDGETRKVKAHSQTHRVDLGTLRGAYNQSEAGSHTV

QRMYGCDVGSDWRFLRGYHQYAYDGKDYIALKEDLRSWTAADMAAQTTKHKWEAAHVAEQLRAY

LEGTCVEWLRRYLENGKETLQRTDAPKTHMTHHAVSDHEATLRCWALSFYPAEITLTWQRDGED

QTQDTELVETRPAGDGTFQKWAAVVVPSGQEQRYTCHVQHEGLPKPLTLRWEPSSQPTIPIVGI

IAGLVLFGAVITGAVVAAVMWRRKSS

>CMV pMHC (CMV NLV peptide portion bolded), amino acid sequence
(SEQ ID NO: 37):
MSRSVALAVLALLSLSGLEANLVPMVATVGASGGSGGGSGGGGSIQRTPKIQVYSRHPAENGKS

NFLNCYVSGFHPSDIEVDLLKNGERIEKVEHSDLSFSKDWSFYLLYYTEFTPTEKDEYACRVNH

VTLSQPKIVKWDRDMGGGGSGGGGSGGGGSGGGGSHSMRYFFTSVSRPGRGEPRFIAVGYVDDT

QFVRFDSDAASQRMEPRAPWIEQEGPEYWDGETRKVKAHSQTHRVDLGTLRGAYNQSEAGSHTV

QRMYGCDVGSDWRFLRGYHQYAYDGKDYIALKEDLRSWTAADMAAQTTKHKWEAAHVAEQLRAY

LEGTCVEWLRRYLENGKETLQRTDAPKTHMTHHAVSDHEATLRCWALSFYPAEITLTWQRDGED

-continued

QTQDTELVETRPAGDGTFQKWAAVVVPSGQEQRYTCHVQHEGLPKPLTLRWEPSSQPTIPIVGI

IAGLVLFGAVITGAVVAAVMWRRKSS

>disulfide trap MHC comprising Y84C mutation(bolded) and position
2 of the linker being a C (bolded); shown with the HGH Signal
Peptide (underlined) and the GL9 peptide (italicized), amino
acid sequence (SEQ ID NO: 39):
MATGSRTSLLLAFGLLCLPWLQEGSA*GILGFVFTLG*CGGSGGGGSGGGGSIQRTPKIQVYSRHP

AENGKSNFLNCYVSGFHPSDIEVDLLKNGERIEKVEHSDLSFSKDWSFYLLYYTEFTPTEKDEY

ACRVNHVTLSQPKIVKWDRDMGGGGSGGGSGSGGGSGSGGGSGGSHSMRYFFTSVSRPGRGEPRFI

AVGYVDDTQFVRFDSDAASQRMEPRAPWIEQEGPEYWDGETRKVKAHSQTHRVDLGTLRGCYNQ

SEAGSHTVQRMYGCDVGSDWRFLRGYHQYAYDGKDYIALKEDLRSWTAADMAAQTTKHKWEAAH

VAEQLRAYLEGTCVEWLRRYLENGKETLQRTDAPKTHMTHHAVSDHEATLRCWALSFYPAEITL

TWQRDGEDQTQDTELVETRPAGDGTFQKWAAVVVPSGQEQRYTCHVQHEGLPKPLTLRWEPSSQ

PTIPIVGIIAGLVLFGAVITGAVVAAVMWRRKSS

>GL9 pMHC (GL9 peptide portion bolded), amino acid sequence
(SEQ ID NO: 41):
MSRSVALAVLALLSLSGLEAGILGFVFTLGGGASGGGGSGGGGSIQRTPKIQVYSRHPAENGKS

NFLNCYVSGFHPSDIEVDLLKNGERIEKVEHSDLSFSKDWSFYLLYYTEFTPTEKDEYACRVNH

VTLSQPKIVKWDRDMGGGGSGGGGSGGGGSGGGGSHSMRYFFTSVSRPGRGEPRFIAVGYVDDT

QFVRFDSDAASQRMEPRAPWIEQEGPEYWDGETRKVKAHSQTHRVDLGTLRGAYNQSEAGSHTV

QRMYGCDVGSDWRFLRGYHQYAYDGKDYIALKEDLRSWTAADMAAQTTKHKWEAAHVAEQLRAY

LEGTCVEWLRRYLENGKETLQRTDAPKTHMTHHAVSDHEATLRCWALSFYPAEITLTWQRDGED

QTQDTELVETRPAGDGTFQKWAAVVVPSGQEQRYTCHVQHEGLPKPLTLRWEPSSQPTIPIVGI

IAGLVLFGAVITGAVVAAVMWRRKSS

>CD80, amino acid sequence (SEQ ID NO: 43):
MGHTRRQGTSPSKCPYLNFFQLLVLAGLSHFCSGVIHVTKEVKEVATLSCGHNVSVEELAQTRI

YWQKEKKMVLTMMSGDMNIWPEYKNRTIFDITNNLSIVILALRPSDEGTYECVVLKYEKDAFKR

EHLAEVTLSVKADFPTPSISDFEIPTSNIRRIICSTSGGFPEPHLSWLENGEELNAINTTVSQD

PETELYAVSSKLDFNMTTNHSFMCLIKYGHLRVNQTFNWNTTKQEHFPDNLLPSWAITLISVNG

IFVICCLTYCFAPRCRE

>CD86, amino acid sequence (SEQ ID NO: 45):
MDPQCTMGLSNILFVMAFLLSGAAPLKIQAYFNETADLPCQFANSQNQSLSELVVFWQDQENLV

LNEVYLGKEKFDSVHSKYMGRTSFDSDSWTLRLHNLQIKDKGLYQCIIHHKKPTGMIRIHQMNS

ELSVLANFSQPEIVPISNITENVYINLTCSSIHGYPEPKKMSVLLRTKNSTIEYDGVMQKSQDN

VTELYDVSISLSVSFPDVTSNMTIFCILETDKTRLLSSPFSIELEDPQPPPDHIPWITAVLPTV

IICVMVFCLILWKWKKKKR

>mouse anti-TCR Beta Clone H57-597 Fab antibody
(light chain-P2A-heavy chain, PDGFR transmembrane domain),
amino acid sequence: (SEQ ID NO: 47):
METDTLLLWVLLLWVPGSTGADYKDDDDKDIQMTQSPSSLPASLGDRVTINCQASQDISNYLNW

YQQKPGKAPKLLIYYTNKLADGVPSRFSGSGSGRDSSFTISSLESEDIGSYYCQQYYNYPWTFG

PGTKLEIKRADAKPTVSIFPPSSEQLGTGSATLVCFVNNFYPKDINVKWKVDGSEKRDGVLQSV

TDQDSKDSTYSLSSTLSLTKADYERHNLYTCEVTHKTSTAAIVKTLNRNECGSGATNFSLLKQA

GDVEENPGPMVPCTLLLLLAAALAPTQTRAEVQLVESGGGLVQPGKSLKLSCEASGFTFSGYGM

HWVRQAPGRGLESVAYITSSSINIKYADAVKGRFTVSRDNAKNLLFLQMNILKSEDTAMYYCAR

FDWDKNYWGQGTMVTVSSAKTTAPSVYPLAPACDSTTSTTNTVTLGCLVKGYFPEPVTVIWNSG

-continued

ALTSGVHTFPSVLHSGLYSLSSSVTVPSSTWPSQTVTCNVAHPASSTTVDLKIEAVGQDTQEVI

VVPHSLPFKVVVISAILALVVLTIISLIILIMLWQKKPR

>mouse anti-CD3 Epsilon Clone 145-2C11 Fab antibody
(light chain-P2A-heavy chain, PDGFR transmembrane domain),
amino acid sequence (SEQ ID NO: 49):
METDTLLLWVLLLWVPGSTGADYKDDDDKYELIQPSSASVTVGETVKITCSGDQLPKNFAYWFQ

QKSDKNILLLIYMDNKRPSGIPERFSGSTSGTTATLTISGAQPEDEAAYYCLSSYGDNNDLVFG

SGTQLTVLRGPKSSPKVTVFPPPSPEELRTNKATLVCLVNDFYPGSATVTWKANGATINDGVKTT

KPSKQGQNYMTSSYLSLTADQWKSHNRVSCQVTHEGETVEKSLSPAECLGSGATNFSLLKQAGD

VEENPGPMVPCTLLLLLAAALAPTQTRAEVYLVESGGDLVQPGSSLKVSCAASGFTFSDFWMYW

VRQAPGKGLEWVGRIKNIPNNYATEYADSVRGRFTISRDDSRNSIYLQMNRLRVDDTAIYYCTR

AGRFDHFDYWGQGTMVTVSSATTTAPSVYPLAPACDSTTSTTDTVTLGCLVKGYFPEPVTVSWN

SGALTSGVHTFPSVLHSGLYSLSSSVTVPSSTWPKQPITCNVAHPASSTKVDKKIEPRAVGQDT

QEVIVVPHSLPFKVVVISAILALVVLTIISLIILIMLWQKKPR*

>Cocal Virus Glycoprotein, amino acid sequence: (SEQ ID NO: 51):
MNFLLLTFIVLPLCSHAKFSIVFPQSQKGNWKNVPSSYHYCPSSSDQNWHNDLLGITMKVKMPK

THKAIQADGWMCHAAKWITTCDFRWYGPKYITHSIHSIQPTSEQCKESIKQTKQGTWMSPGFPP

QNCGYATVTDSVAVVVQATPHHVLVDEYTGEWIDSQFPNGKCETEECETVHNSTVWYSDYKVTG

LCDATLVDTEITFFSEDGKKESIGKPNTGYRSNYFAYEKGDKVCKMNYCKHAGVRLPSGVWFEF

VDQDVYAAAKLPECPVGATISAPTQTSVDVSLILDVERILDYSLCQETWSKIRSKQPVSPVDLS

YLAPKNPGTGPAFTIINGTLKYFETRYIRIDIDNPIISKMVGKISGSQTERELWTEWFPYEGVE

IGPNGILKTPTGYKFPLFMIGHGMLDSDLHKTSQAEVFEHPHLAEAPKQLPEEETLFFGDTGIS

KNPVELIEGWFSSWKSTVVTFFFAIGVFILLYVVARIVIAVRYRYQGSNNKRIYNDIEMSRFRK*

>Cocal Virus Glycoprotein, DNA sequence: (SEQ ID NO: 52):
ATGAACTTTCTGCTGCTCACGTTTATCGTACTCCCGTTGTGCTCTCATGCGAAATTTTCAATAG

TCTTTCCTCAGTCCCAGAAAGGGAATTGGAAAAATGTTCCCTCCAGTTACCACTATTGTCCCTC

CTCCTCTGACCAAAACTGGCACAATGACTTGCTCGGGATTACAATGAAAGTAAAGATGCCGAAA

ACCCATAAAGCCATACAGGCGGATGGGTGGATGTGTCACGCTGCGAAGTGGATCACTACATGCG

ATTTCCGGTGGTATGGCCCTAAGTACATTACACACTCTATCCATAGCATACAGCCGACATCAGA

GCAATGCAAAGAGAGTATTAAACAGACCAAACAAGGGACATGGATGAGCCCTGGCTTTCCACCT

CAGAATTGTGGGTACGCGACCGTCACGGATAGTGTCGCTGTTGTGGTGCAGGCCACGCCACATC

ACGTACTCGTAGATGAATATACTGGTGAATGGATCGACTCCCAATTCCCGAATGGGAAATGTGA

GACGGAAGAGTGCGAAACAGTGCATAACTCAACCGTTTGGTATTCCGATTACAAGGTTACTGGT

CTTTGCGACGCCACCCTCGTGGATACCGAGATCACGTTTTTTAGTGAGGATGGCAAGAAAGAGT

CAATAGGCAAACCTAATACTGGCTACCGGAGTAACTATTTCGCTTACGAGAAGGGTGACAAGGT

ATGTAAAATGAACTATTGCAAGCATGCGGGAGTGCGACTCCCCAGTGGGGTATGGTTCGAATTT

GTTGACCAAGACGTATACGCCGCTGCGAAGTTGCCAGAATGCCCCGTAGGCGCGACCATTTCAG

CACCTACCCAAACGTCCGTTGACGTCTCCTTGATACTGGATGTAGAGCGAATCCTGGACTACAG

TCTCTGCCAGGAAACGTGGTCAAAAATAAGAAGTAAGCAGCCAGTTTCACCCGTGGATCTGTCT

TATCTGGCGCCAAAAAACCCGGGCACGGGCCCTGCTTTTACCATAATTAACGGAACGCTTAAAT

ACTTCGAAACCCGCTACATTAGAATCGATATAGACAATCCTATTATCAGCAAGATGGTAGGGAA

GATATCTGGGTCTCAAACGGAGCGAGAATTGTGGACGGAGTGGTTCCCTTATGAGGGAGTGGAA

ATTGGGCCCAACGGGATCCTCAAGACCCCAACGGGTTACAAGTTCCCTCTGTTTATGATCGGCC

-continued

ATGGCATGTTGGACAGTGACTTGCACAAAACATCTCAGGCAGAGGTTTTCGAACATCCACATTT

GGCGGAGGCGCCCAAGCAACTTCCAGAAGAAGAAACTCTCTTCTTTGGAGATACAGGCATTTCA

AAAAATCCTGTAGAACTGATAGAAGGGTGGTTCTCTTCCTGGAAATCAACGGTTGTCACGTTTT

TCTTTGCAATAGGCGTATTTATACTCCTGTACGTCGTAGCCCGCATTGTGATCGCAGTACGATA

CAGATACCAGGGCAGTAACAATAAACGCATATATAATGACATCGAAATGTCAAGGTTCCGAAAG tga

>Cocal-dead (mutations to ablate native tropism bolded in protein
sequence; these are K64Q and R371A, counting from the start codon),
amino acid sequence: (SEQ ID NO: 53):
MNFLLLTFIVLPLCSHAKFSIVFPQSQKGNWKNVPSSYHYCPSSSDQNWHNDLLGITMKVKMPQ

THKAIQADGWMCHAAKWITTCDFRWYGPKYITHSIHSIQPTSEQCKESIKQTKQGTWMSPGFPP

QNCGYATVTDSVAVVVQATPHHVLVDEYTGEWIDSQFPNGKCETEECETVHNSTVWYSDYKVTG

LCDATLVDTEITFFSEDGKKESIGKPNTGYRSNYFAYEKGDKVCKMNYCKHAGVRLPSGVWFEF

VDQDVYAAAKLPECPVGATISAPTQTSVDVSLILDVERILDYSLCQETWSKIRSKQPVSPVDLS

YLAPKNPGTGPAFTIINGTLKYFETRYIRIDIDNPIISKMVGKISGSQTEAELWTEWFPYEGVE

IGPNGILKTPTGYKFPLFMIGHGMLDSDLHKTSQAEVFEHPHLAEAPKQLPEEETLFFGDTGIS

KNPVELIEGWFSSWKSTVVTFFFAIGVFILLYVVARIVIAVRYRYQGSNNKRIYNDIEMSRFRK

>Cocal-dead (mutations to ablate native tropism), DNA sequence:
(SEQ ID NO: 54):
ATGAACTTTCTGCTGCTCACGTTTATCGTACTCCCGTTGTGCTCTCATGCGAAATTTTCAATAG

TCTTTCCTCAGTCCCAGAAAGGGAATTGGAAAAATGTTCCCTCCAGTTACCACTATTGTCCCTC

CTCCTCTGACCAAAACTGGCACAATGACTTGCTCGGGATTACAATGAAAGTAAAGATGCCGcag

ACCCATAAAGCCATACAGGCGGATGGGTGGATGTGTCACGCTGCGAAGTGGATCACTACATGCG

ATTTCCGGTGGTATGGCCCTAAGTACATTACACACTCTATCCATAGCATACAGCCGACATCAGA

GCAATGCAAAGAGAGTATTAAACAGACCAAACAAGGGACATGGATGAGCCCTGGCTTTCCACCT

CAGAATTGTGGGTACGCGACCGTCACGGATAGTGTCGCTGTTGTGGTGCAGGCCACGCCACATC

ACGTACTCGTAGATGAATATACTGGTGAATGGATCGACTCCCAATTCCCGAATGGGAAATGTGA

GACGGAAGAGTGCGAAACAGTGCATAACTCAACCGTTTGGTATTCCGATTACAAGGTTACTGGT

CTTTGCGACGCCACCCTCGTGGATACCGAGATCACGTTTTTTAGTGAGGATGGCAAGAAAGAGT

CAATAGGCAAACCTAATACTGGCTACCGGAGTAACTATTTCGCTTACGAGAAGGGTGACAAGGT

ATGTAAAATGAACTATTGCAAGCATGCGGGAGTGCGACTCCCCAGTGGGGTATGGTTCGAATTT

GTTGACCAAGACGTATACGCCGCTGCGAAGTTGCCAGAATGCCCCGTAGGCGCGACCATTTCAG

CACCTACCCAAACGTCCGTTGACGTCTCCTTGATACTGGATGTAGAGCGAATCCTGGACTACAG

TCTCTGCCAGGAAACGTGGTCAAAAATAAGAAGTAAGCAGCCAGTTTCACCCGTGGATCGTCT

TATCTGGCGCCAAAAAACCCGGGCACGGGCCCTGCTTTTACCATAATTAACGGAACGCTTAAAT

ACTTCGAAACCCGCTACATTAGAATCGATATAGACAATCCTATTATCAGCAAGATGGTAGGGAA

GATATCTGGGTCTCAAACGGAGgccGAATTGTGGACGGAGTGGTTCCCTTATGAGGGAGTGGAA

ATTGGGCCCAACGGGATCCTCAAGACCCCAACGGGTTACAAGTTCCCTCTGTTTATGATCGGCC

ATGGCATGTTGGACAGTGACTTGCACAAAACATCTCAGGCAGAGGTTTTCGAACATCCACATTT

GGCGGAGGCGCCCAAGCAACTTCCAGAAGAAGAAACTCTCTTCTTTGGAGATACAGGCATTTCA

AAAAATCCTGTAGAACTGATAGAAGGGTGGTTCTCTTCCTGGAAATCAACGGTTGTCACGTTTT

-continued

TCTTTGCAATAGGCGTATTTATACTCCTGTACGTCGTAGCCCGCATTGTGATCGCAGTACGATA

CAGATACCAGGGCAGTAACAATAAACGCATATATAATGACATCGAAATGTCAAGGTTCCGAAAG tga

---

What is claimed is:

1. A composition comprising a lentivirus, the lentivirus comprising:

(a) a nucleic acid;

(b) a viral envelope comprising (i) a vesicular stomatitis virus (VSV)-G envelope protein comprising an amino acid sequence at least 95% identical to SEQ ID NO: 13, wherein the VSV-G envelope protein comprises one or more amino acid mutations at position 47 (lysine, K) and/or position 354 (arginine, R), wherein the amino acid mutation(s) diminish the native viral tropism of the VSV-G envelope protein compared to the non-mutated VSV-G envelope protein; and (ii) a non-viral membrane-bound protein comprising a trans-membrane-domain and an extracellular targeting domain that binds to a ligand expressed on the surface of a T cell or a B cell.

2. The composition of claim 1, wherein the nucleic acid encodes an mRNA, a double-stranded DNA, an antisense RNA, a microRNA, a gene of interest, or a protein.

3. The composition of claim 1, wherein the one or more amino acid mutations comprise an amino acid mutation at position K47 or position R354.

4. The composition of claim 1, wherein the one or more amino acid mutations comprise an amino acid mutation at position K47 and position R354.

5. The composition of claim 1, wherein the one or more amino acid mutations comprise a K47A or K47Q amino acid substitution and/or an R354A or R354Q amino acid substitution.

6. The composition of claim 1, wherein the extracellular targeting domain comprises a protein, a peptide, or an antibody.

7. The composition of claim 6, wherein the extracellular targeting domain comprises an interleukin-13 protein domain, a CD80 protein domain, a full-length antibody, an antibody fragment, a nanobody, a single chain antibody (scFv), an anti-CD19 antibody, an anti-TCR antibody, or an anti-CD3 antibody.

8. The lentivirus of claim 1, wherein the ligand comprises a T cell receptor (TCR), a cytokine receptor, a cytokine, a T cell surface marker, CD3, CD19, or CD20.

9. A method of delivering a nucleic acid to a T cell or B cell, the method comprising:

(a) providing a composition comprising a lentivirus, the lentivirus comprising: a nucleic acid and a viral envelope comprising (i) a VSV-G envelope protein comprising an amino acid sequence at least 95% identical to SEQ ID NO: 13, wherein the VSV-G envelope protein comprises one or more amino acid mutations at position 47 (lysine, K) and/or position 354 (arginine, R), wherein the amino acid mutation(s) diminish the native viral tropism of the VSV-G envelope protein compared to the non-mutated VSV-G envelope protein; and (ii) a non-viral membrane-bound protein comprising a transmembrane-domain and an extracellular targeting domain that binds to a ligand expressed on the surface of a T cell or a B cell;

(b) contacting the composition with the T cell or B cell, thereby delivering the nucleic acid to the T cell or B cell.

10. The method of claim 9, wherein the nucleic acid encodes an mRNA, a double-stranded DNA, an antisense RNA, a microRNA, a gene of interest, or a protein.

11. The method of claim 9, wherein the one or more amino acid mutations comprise an amino acid mutation at position K47 or position R354.

12. The method of claim 9, wherein the one or more amino acid mutations comprise an amino acid mutation at position K47 and position R354.

13. The method of claim 9, wherein the one or more amino acid mutations comprise a K47A or K47Q amino acid substitution and/or an R354A or R354Q amino acid substitution.

14. The method of claim 9, wherein the extracellular targeting domain comprises a protein, a peptide, or an antibody.

15. The method of claim 14, wherein the extracellular targeting domain comprises an interleukin-13 protein domain, a CD80 protein domain, a full-length antibody, an antibody fragment, a nanobody, an scFv, an anti-CD19 antibody, an anti-TCR antibody, or an anti-CD3 antibody.

16. The method of claim 9, wherein the ligand comprises a T cell receptor (TCR), a cytokine receptor, a cytokine, a T cell surface marker, CD3, CD19, or CD20.

17. A composition comprising a lentivirus, the lentivirus comprising (a) a nucleic acid;

(b) a viral envelope comprising:

(i) a VSV-G envelope protein comprising an amino acid sequence at least 95% identical to SEQ ID NO: 13, wherein the VSV-G envelope protein comprises one or more amino acid mutations at position 47 (lysine, K) and/or position 354 (arginine, R), wherein the amino acid mutation(s) diminish the native viral tropism of the VSV-G envelope protein compared to the non-mutated VSV-G envelope protein; and (ii) a non-viral membrane-bound protein comprising a transmembrane domain and an extracellular targeting domain that comprises an anti-CD3 antibody.

18. The composition of claim 17, wherein the nucleic acid encodes an mRNA, a double- stranded DNA, an antisense RNA, a microRNA, a gene of interest, or a protein.

19. The composition of claim 17, wherein the one or more amino acid mutations comprise an amino acid mutation at position K47 or position R354.

20. The composition of claim 17, wherein the one or more amino acid mutations comprise an amino acid mutation at position K47 and position R354.

21. The composition of claim 17, wherein the one or more amino acid mutations comprise a K47A or K47Q amino acid substitution and/or an R354A or R354Q amino acid substitution.

22. The composition of claim 17, wherein the viral envelope further comprises a non-viral membrane-bound protein comprising a transmembrane domain and an extracellular targeting domain that comprises a full-length antibody, an antibody fragment, a nanobody, an scFv, or an anti-TCR antibody.

23. The composition of claim 17, wherein the viral envelope further comprises a non-viral membrane-bound protein that comprises a CD80 protein comprising a CD80 extracellular domain and a transmembrane domain.

24. A method of delivering a nucleic acid to a T cell, the method comprising:

(a) providing a composition comprising a lentivirus, the lentivirus comprising: a nucleic acid and a viral envelope comprising (i) a VSV-G envelope protein comprising an amino acid sequence at least 95% identical to SEQ ID NO: 13, wherein the VSV-G envelope protein comprises one or more amino acid mutations at position 47 (lysine, K) and/or position 354 (arginine, R), wherein the amino acid mutation(s) diminish the native viral tropism of the VSV-G envelope protein compared to the non-mutated VSV-G envelope protein; and (ii) a non-viral membrane-bound protein comprising a transmembrane domain and an extracellular targeting domain that comprises an anti-CD3 antibody;

(b) contacting the lentivirus with the T cell, thereby delivering the nucleic acid to the T cell.

25. The method of claim 24, wherein the nucleic acid encodes an mRNA, a double-stranded DNA, an antisense RNA, a microRNA, a gene of interest, or a protein.

26. The method of claim 24, wherein the one or more amino acid mutations comprise an amino acid mutation at position K47 or position R354.

27. The method of claim 24, wherein the one or more amino acid mutations comprise an amino acid mutation at position K47 and position R354.

28. The method of claim 24, wherein the one or more amino acid mutations comprise a K47A or K47Q amino acid substitution and/or an R354A or R354Q amino acid substitution.

29. The method of claim 24, wherein the viral envelope further comprises a non-viral membrane-bound protein comprising a transmembrane domain and an extracellular targeting domain that comprises a full-length antibody, an antibody fragment, a nanobody, an scFv, or an anti-TCR antibody.

30. The method of claim 24, wherein the viral envelope further comprises a non-viral membrane-bound protein that comprises a CD80 protein comprising a CD80 extracellular domain and a transmembrane domain.

\*  \*  \*  \*  \*